United States Patent
Jeong et al.

(10) Patent No.: US 10,227,306 B2
(45) Date of Patent: Mar. 12, 2019

(54) COMPOUNDS FOR INHIBITING C-MYC/MAX/DNA COMPLEX FORMATION

(71) Applicants: NATIONAL CANCER CENTER, Goyang-si, Gyeonggi-do (KR); KOREA RESEARCH INSTITUTE OF CHEMICAL TECHNOLOGY, Daejeon (KR)

(72) Inventors: Kyung Chae Jeong, Goyang-si (KR); Hwan Jung Lim, Daejeon (KR); Seong Jun Park, Daejeon (KR); Ho Kyung Seo, Paju-si (KR); Kyung Ohk Ahn, Gunpo-si (KR); Sang Jin Lee, Paju-si (KR); Eun Sook Lee, Gwacheon-si (KR)

(73) Assignees: NATIONAL CANCER CENTER, Goyang-si, Gyeonggi-do (KR); KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 0 days.

(21) Appl. No.: 15/909,088

(22) Filed: Mar. 1, 2018

(65) Prior Publication Data
US 2018/0186744 A1 Jul. 5, 2018

Related U.S. Application Data
(63) Continuation of application No. 15/663,179, filed on Jul. 28, 2017, now Pat. No. 9,951,021.

(30) Foreign Application Priority Data

Jul. 29, 2016 (KR) .................. 10-2016-0097429
Jul. 24, 2017 (KR) .................. 10-2017-0093661

(51) Int. Cl.
| | | |
|---|---|---|
| C07D 215/36 | (2006.01) | |
| C07D 215/58 | (2006.01) | |
| C07D 401/12 | (2006.01) | |
| C07D 401/14 | (2006.01) | |
| C07D 405/12 | (2006.01) | |
| C07D 409/12 | (2006.01) | |
| C07D 413/12 | (2006.01) | |
| C07D 471/04 | (2006.01) | |
| C07D 519/00 | (2006.01) | |
| C07D 215/233 | (2006.01) | |

(52) U.S. Cl.
CPC ....... *C07D 215/36* (2013.01); *C07D 215/233* (2013.01); *C07D 215/58* (2013.01); *C07D 401/12* (2013.01); *C07D 401/14* (2013.01); *C07D 405/12* (2013.01); *C07D 409/12* (2013.01); *C07D 413/12* (2013.01); *C07D 471/04* (2013.01); *C07D 519/00* (2013.01)

(58) Field of Classification Search
CPC ..................... C07D 215/36; C07D 215/233
See application file for complete search history.

(56) References Cited

U.S. PATENT DOCUMENTS 9,951,021 B2 * 4/2018 Jeong .................. C07D 215/36

OTHER PUBLICATIONS

Choi et al. "Isothiazole ring formation with substituted 2-alkylthio-3-acyl-4-quinolinone using O-(mesitylenesulfonyl)hydroxylamine (MSH)" Synlett, 2003, No. 2, pp. 166-172.*

* cited by examiner

*Primary Examiner* — Joseph R Kosack
(74) *Attorney, Agent, or Firm* — Vorys, Sater, Seymour and Pease LLP; Mih Suhn Koh

(57) ABSTRACT

Disclosed are novel compounds of specific chemical structures having inhibitory activity on c-Myc/Max/DNA complex formation or pharmaceutically acceptable salts thereof.

3 Claims, No Drawings

COMPOUNDS FOR INHIBITING C-MYC/MAX/DNA COMPLEX FORMATION

CROSS-REFERENCE TO RELATED APPLICATION

This application is a continuation application of U.S. patent application Ser. No. 15/663,179 filed on Jul. 28, 2017, which claiming the benefit under 35 U.S.C. § 119 of the Korean Patent Application No. 10-2016-0097429, filed on Jul. 29, 2016, and 10-2017-0093661 field on Jul. 24, 2017, the disclosure of which is incorporated herein by reference in its entirety.

STATEMENT REGARDING GOVERNMENT RIGHTS

The present invention was undertaken with the support of 1) Development of pre-clinical and clinical candidates of c-Myc inhibitor No. 1511220 grant funded by the National Cancer Center, 2) Development of c-Myc inhibitor for bladder cancer therapy No. 1510130 grant funded by the National Cancer Center, 3) (Action Project) Development of pre-clinical and clinical candidates of c-Myc inhibitor No. IK1506-H02 grant funded by the Korea Research Institute of Chemical Technology, 4) (Action Project) Development of pre-clinical and clinical candidates of c-Myc inhibitor No. IK1606-H02 grant funded by the Korea Research Institute of Chemical Technology and 5) (Action Project) Development of pre-clinical and clinical candidates of c-Myc inhibitor No. IK1706H02 grant funded by the Korea Research Institute of Chemical Technology.

BACKGROUND

1. Field of the Disclosure

The present disclosure relates to a group of novel compounds having inhibitory activity on c-Myc/Max/DNA complex formation.

2. Discussion of Related Art c-myc is a proto-oncogene encoding the c-Myc oncoprotein regulating cell transformation, growth, and differentiation, apoptosis, cell cycle progression and the like. Myc family proteins including c-Myc form a heterodimer with the basic/helix-loop-helix/leucine zipper (bHLHZip) domain of Max protein, and the Myc/Max heterodimer binds to a specific DNA sequence (i.e., E-box motif). Heterodimer formation with Max protein and subsequent DNA binding of the heterodimer are steps required for transcriptional activation of c-Myc target genes, and play important roles in promoting cell proliferation, malignant transformation, apoptosis and the like (see International Patent Publication No. WO2015/089180).

Abnormal expression of c-myc has been reported to be associated with a variety of cancers, including lung cancer, colorectal cancer, colon cancer, rectal cancer, breast cancer, bladder cancer, leukemia, myelogenous leukemia, lymphoma, small cell lung cancer, lung cancer, cervical carcinoma, osteosarcoma, glioblastoma, melanoma and the like (see Nature 1983 Nov. 10-16; 306(5939): 194-196; Cancer Res 1985 April; 45(4): 1823-1827; and Mol. BioSyst., 2010, 6: 1503-1509). In addition, it has been reported that c-myc expression is elevated or deregulated in various human cancers and is associated with tumors (Oncogene, 1999, 18(19), 3004-16). Therefore, there has been much effort to develop anti-cancer agents or anti-tumor agents by regulating c-myc expression.

However, in development of related drugs, development of substances that directly inhibit c-Myc function has not been technically feasible, and thus most attempts have been made to indirectly regulate c-Myc function. However, such indirect c-Myc inhibitors may cause many unexpected side effects. In particular, since c-Myc plays an important role in regulating cellular activity in the body, serious side effects may occur when c-Myc inhibitors are not highly selective for c-Myc. In fact, development of many substances was discontinued due to toxicity problems. For example, JQ1 has recently been reported to be useful for myeloma treatment by indirectly regulating c-Myc expression (see Cell. 2011, 146(6): 904-917 and Blood. 2012, 120(14): 2843-2852), but development of JQ1 was discontinued due to serious side effects thereof.

Specifically, a motif responsible for binding of Myc and Max is the leucine zipper motif commonly found in general protein structures. Thus, certain proteins that bind to the leucine zipper motif inhibit Myc/Max heterodimer formation, but have low selectivity.

In other words, when searching for a candidate substance, a substance that binds to a unique motif present in a Myc/Max heterodimer should be selected and selectivity thereof should be confirmed, or side effects may be caused. For example, certain c-Myc inhibitors exhibit low selectivity, inhibiting the activity of c-Jun/Fos transcription factors with similar structures. Therefore, it is important to develop an inhibitor capable of selectively acting on a Myc/Max heterodimer. In addition, a targeting substance that inhibits formation of a complex between a c-Myc/Max dimer and DNA may have higher selectivity than a targeting substance that inhibits c-Myc/Max dimer formation.

Accordingly, it is necessary to develop an inhibitor capable of directly inhibiting c-Myc action. Specifically, there is demand for the development of an inhibitor that has high selectivity for c-Myc and is capable of inhibiting c-Myc activity, thus reducing side effects.

PRIOR ART DOCUMENTS

Patent Documents

1. International Patent Publication No. WO 2014/071247 (disclosed on May 8, 2014)
2. International Patent Publication No. WO 2015/089180 (disclosed on Jun. 18, 2014)

Non-Patent Documents

1. Steven Fletcher et al., Small-Molecule Inhibitors of the Myc Oncoprotein, Biochimica et Biophysica Acta 1849 (2015) 525-543.
2. Bing-Jia Chen et al., Small Molecules Targeting c-Myc Oncogene: Promising Anti-Cancer Therapeutics, Int J Biol Sci 2014; 10(10):1084-1096.
3. Kyung-Chae Jeong et al., Small-Molecule Inhibitors of c-Myc Transcriptional Factor Suppress Proliferation and Induce Apoptosis of Promyelocytic Leukemia Cell via Cell Cycle Arrest, Mol. BioSyst., 2010, 6, 1503-1509.
4. Ho Kyung Seo et al., Antitumor Activity of the c-Myc Inhibitor KSI-3716 in Gemcitabine-Resistant Bladder Cancer, Oncotarget, 2014, Vol. 5, No. 2: 326-337.

SUMMARY OF THE DISCLOSURE

Therefore, the present disclosure has been made in view of the above problems, and it is an objective of the present disclosure to provide novel compounds having inhibitory activity on c-Myc/Max/DNA complex formation.

In accordance with the present disclosure, the above and other objectives can be accomplished by the provision of compounds having the structures corresponding to Formula 1a or 1b below or pharmaceutically acceptable salts thereof:

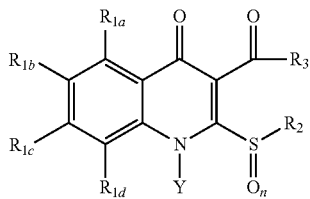

Formula 1a

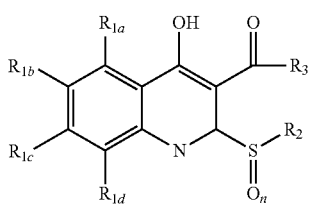

Formula 1b in Formula 1, $R_{1a}$ to $R_{1d}$ are each independently hydrogen, a halogen, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{2-10}$ alkenyl, $C_{2-10}$ haloalkenyl, $C_{2-10}$ alkynyl, $C_{2-10}$ haloalkynyl, a hydroxyl group, nitro, cyano, $C_{1-6}$ alkoxycarbonyl, amino, $C_{1-6}$ alkylamino, di($C_{1-6}$ alkyl)amino, amino($C_{1-6}$)alkyl, ($C_{1-6}$)alkylamino($C_{1-6}$)alkyl, $C_{1-6}$ alkanoyl, $C_{3-7}$ cycloalkyl, an aryl, a heterocycle, or a heteroaryl, wherein $R_{1a}$ to $R_{1d}$ may be each independently unsubstituted or one or more hydrogens may be optionally substituted;

$R_2$ is hydrogen, $C_{1-6}$ alkyl, ($C_{1-6}$)alkoxy($C_{1-6}$)alkyl, $C_{1-6}$ haloalkyl, $C_{1-6}$ hydroxyalkyl, $C_{1-6}$ alkoxy, $C_{1-6}$ haloalkoxy, $C_{2-10}$ alkenyl, $C_{2-10}$ alkenyl carboxy, $C_{2-10}$ haloalkenyl, $C_{2-10}$ alkynyl, $C_{2-10}$ haloalkynyl, a hydroxyl group, nitro, cyano, $C_{1-6}$ alkoxycarbonyl, amino, $C_{1-6}$ alkylamino, $C_{1-6}$ cyanoalkyl, di($C_{1-6}$ alkyl)amino, amino($C_{1-6}$)alkyl, ($C_{1-6}$)alkylamino($C_{1-6}$)alkyl, $C_{1-6}$ alkanoyl, $C_{3-7}$ cycloalkyl, ($C_{1-6}$)alkyl($C_{3-7}$)cycloalkyl, aryl, ($C_{1-6}$)alkylaryl, ($C_{1-6}$)haloalkylaryl, ($C_{2-6}$)alkenylamide($C_{1-6}$)alkylalkoxy, a heterocycle, ($C_{1-6}$)alkylheterocycle, a heteroaryl, or ($C_{1-6}$)alkylheteroaryl, wherein $R_2$ may be unsubstituted or optionally substituted;

$R_3$ is $C_{1-4}$ alkyl, isoalkyl, cycloalkyl, phenyl, or $C_{1-4}$ haloalkyl;

n is an integer from 0 to 2; and

Y is hydrogen, an alkyl, a haloalkyl, —C(O)alkyl, —C(O)aryl, a sulfonylalkyl, a sulfonylaryl, an aryl, or an alkylaryl, wherein the alkyl has 1 to 10 carbon atoms, preferably 1 to 4 carbon atoms, and the aryl may be unsubstituted or one or more hydrogens may be optionally substituted.

In one embodiment, the present disclosure provides compounds corresponding to Formula 2a or 2b below or pharmaceutically acceptable salts thereof:

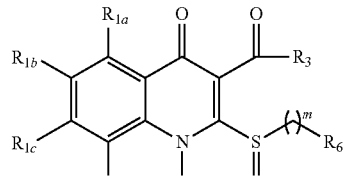

Formula 2a

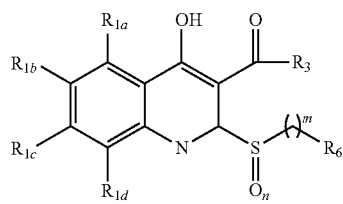

Formula 2b in Formula 2, $R_{1a}$ to $R_{1d}$, $R_3$, n and Y are as defined in Formula 1;

m is an integer from 0 to 4; and $R_6$ is phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, 1,2,5-oxadiazole, pyrrolo[2,3-b]pyridine, or benzothiophene, which may be unsubstituted or may be optionally substituted with one or more of hydrogen, $C_{1-6}$ alkyl, $C_{1-6}$ haloalkyl, $C_{1-6}$ alkoxy, halogen or may be optionally substituted with one or more of hydrogen, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene or may be substituted with unsubstituted phenyl.

In one embodiment, the present disclosure provides compounds corresponding to Formula 3a or 3b below or pharmaceutically acceptable salts thereof:

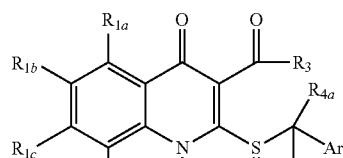

Formula 3a

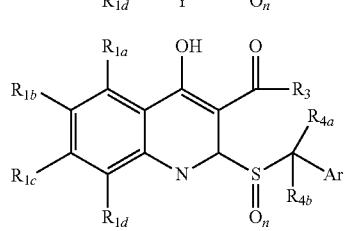

Formula 3b in Formula 3, $R_{1a}$ to $R_{1d}$, $R_3$, and n are as defined in Formula 1;

$R_{4a}$ and $R_{4b}$ are each independently hydrogen, a halogen, $C_{1-4}$ alkyl, $C_{1-4}$ haloalkyl, or $C_{1-4}$ alkyl in which one or more hydrogens are substituted with substituents other than halogen;

Ar is phenyl, heteroaryl being 5-6-membered and having heteroatoms selected independently from N, S, or O, or biheteroaryl being 8-12-membered and having heteroatoms selected independently from N, S, or O, wherein Ar may be unsubstituted or may be optionally substituted with one or more of a halogen, $C_{1-6}$ alkyl, $C_{1-6}$ alkylthio, $C_{1-6}$ haloalkyl, $C_{1-6}$ haloalkylthio, $C_{1-6}$ alkoxy, $C_{1-6}$ haloalkoxy, $C_{2-10}$ alkenyl, $C_{2-10}$ haloalkenyl, $C_{2-10}$ alkynyl, $C_{2-10}$ haloalkynyl, a hydroxyl group, COOH, nitro, cyano, $C_{1-6}$ alkoxycarbonyl, amino, $C_{1-6}$ alkylamino, di($C_{1-6}$ alkyl)amino, amino($C_{1-6}$)alkyl, ($C_{1-6}$)alkylamino($C_{1-6}$)alkyl, ($C_{1-6}$)alkoxy($C_{1-6}$)alkylamino, ($C_{1-6}$)alkylamino($C_{1-6}$)alkylamino, $C_{1-6}$ alkanoyl, $SF_5$, $S(O)CF_3$, $SCF_3$, NHC(=O)$CH_3$, C(=O)NH$CH_3$, NHSO2CH3, $C_{3-7}$ cycloalkyl, an aryl, benzoyl, a heterocycle, a heteroaryl, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene, wherein the substituents of Ar may be unsubstituted or may be optionally substituted with one or more of CF3, a halogen, ($C_{1-3}$)alkyl, ($C_{1-3}$)haloalkyl, hydrogen, COOH, nitro, cyano, amino, di(C1-3 alkyl)amino, NHC(=O)CH3, or C(=O)NHCH3.

In accordance with an aspect of the present disclosure, the above and other objectives can be accomplished by the provision of a (pharmaceutical) composition including compounds according to Formula 1, 2 or 3 or pharmaceutically acceptable salts thereof, and a pharmaceutically acceptable carrier or additive.

In accordance with various aspects, the (pharmaceutical) composition may further include one or more additional pharmaceutically active agents.

Novel compounds of the present disclosure having structures of Formula 1, 2 or 3 or pharmaceutically acceptable salts thereof are useful for inhibiting c-Myc/Max/DNA complex formation, and thus may be useful for treatment or prevention of cancers. Cancers, neoplasia, or tumors that can be treated by inhibiting c-Myc/Max/DNA complex formation include, for example, lung cancer (including small cell lung cancer and non-small cell lung cancer), colorectal cancer, colon cancer, rectal cancer, breast cancer, prostate cancer, bladder cancer, myeloma, leukemia, myelogenous leukemia, lymphoma, cervical carcinoma, osteosarcoma, glioblastoma, melanoma, pancreatic cancer, gastric cancer, liver cancer, kidney cancer, gallbladder cancer, biliary tract cancer, and esophageal cancer.

Novel compounds according to the present disclosure and a (pharmaceutical) composition including the compounds are described in detail as follows.

The following description is merely illustrative and is not intended to limit the present disclosure to specific application or uses.

As used herein, the following terms are defined as follows.

In the present specification, the terms "substituent", "radical", "group", "moiety", and "fragment" may be used interchangeably.

As used herein, the term "patient" refers to an animal (e.g., cow, horse, sheep, pig, chicken, turkey, quail, cat, dog, mouse, rat, rabbit or guinea pig), preferably a mammal such as a primate (e.g., monkey or human), and most preferably a human.

As used herein, the term "alkyl", when the number of carbon atoms is not particularly limited, refers to a saturated straight or branched non-cyclic hydrocarbon having 1 to 10 carbon atoms. The term "lower alkyl" refers to a straight or branched alkyl having 1 to 4 carbon atoms. Representative saturated straight alkyls include -methyl, -ethyl, -n-propyl, -n-butyl, -n-pentyl, -n-hexyl, -n-heptyl, -n-octyl, -n-nonyl and -n-decyl, whereas saturated branched alkyls include -isopropyl, -sec-butyl, -isobutyl, -tert-butyl, isopentyl, 2-methylbutyl, 3-methylbutyl, 2-methylpentyl, 3-methylpentyl, 4-methylpentyl, 2-methylhexyl, 3-methylhexyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl.

In the present specification, "$C_{1-6}$" means 1 to 6 carbon atoms. For example, $C_{1-6}$ alkyl means an alkyl having 1 to 6 carbon atoms.

As used herein, the term "alkenyl" refers to a saturated straight or branched non-cyclic hydrocarbon having 2 to 10 carbon atoms and including at least one carbon-carbon double bond. Representative straight and branched ($C_2$-$C_{10}$) alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, and -3-decenyl. These alkenyl groups may be optionally substituted. The term "cyclic alkylidene" is a ring having 3 to 8 carbon atoms and including at least one carbon-carbon double bond, and the ring may have 1 to 3 heteroatoms.

As used herein, the term "alkynyl" refers to a straight or branched non-cyclic hydrocarbon having 2 to 10 carbon atoms and including at least one carbon-carbon triple bond. Representative straight or branched ($C_2$-$C_{10}$) alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonylyl, -2-nonylyl, -8-nonylyl, -1-decynyl, -2-decynyl, and -9-decynyl. These alkynyl groups may be optionally substituted.

As used herein, the terms "halogen" and "halo" refer to fluorine, chlorine, bromine or iodine.

As used herein, the term "haloalkyl", "haloalkoxy", "haloalkenyl" or "haloalkynyl" refers to an alkyl, alkoxy, alkenyl or alkynyl group wherein one or more hydrogen atoms are substituted with halogen atoms, respectively. For example, haloalkyls include —$CF_3$, —$CHF_2$, —$CH_2F$, —$CBr_3$, —$CHBr_2$, —$CH_2Br$, —$CCl_3$, —$CHCl_2$, —$CH_2Cl$, —$CI_3$, —$CHI_2$, —$CH_2I$, —$CH_2$—$CF_3$, —$CH_2$—$CHF_2$, —$CH_2$—$CH_2F$, —$CH_2$—$CBr_3$, —$CH_2$—$CHBr_2$, —$CH_2$—$CH_2Br$, —$CH_2$—$CCl_3$, —$CH_2$—$CHCl_2$, —$CH_2$—$CH_2Cl$, —$CH_2$—$CI_3$, —$CH_2$—$CHI_2$, —$CH_2$—$CH_2I$, and the like. Here, the alkyl and the halogen are as defined above.

As used herein, the term "alkanoyl" or "acyl" refers to —C(O)alkyl groups including —C(O)$CH_3$, —C(O)$CH_2CH_3$, —C(O)$(CH_2)_2CH_3$, —C(O)$(CH_2)_3CH_3$, —C(O)$(CH_2)_4CH_3$, —C(O)$(CH_2)_5CH_3$, and the like, wherein the alkyl is as defined above.

As used herein, the term "alkanoyloxy" or "acyloxy" refers to —OC(O)alkyl groups including —OC(O)$CH_3$, —OC(O)$CH_2CH_3$, —OC(O)$(CH_2)_2CH_3$, —OC(O)$(CH_2)_3CH_3$, —OC(O)$(CH_2)_4CH_3$, —OC(O)$(CH_2)_5CH_3$, and the like, wherein the alkyl is as defined above.

As used herein, the term "alkoxy" refers to —O-(alkyl) including —OCH$_3$, —OCH$_2$CH$_3$, —O(CH$_2$)$_2$CH$_3$, —O(CH$_2$)$_3$CH$_3$, —O(CH$_2$)$_4$CH$_3$, —O(CH$_2$)$_5$CH$_3$, and the like, wherein the alkyl is as defined above.

As used herein, the term "lower alkoxy" refers to —O-(lower alkyl), wherein the lower alkyl is as defined above.

As used herein, the term "aryl" refers to a carbocyclic aromatic group containing 5 to 10 cyclic atoms. Representative examples include phenyl, tolyl, xylyl, naphthyl, tetrahydronaphthyl, anthracenyl, fluorenyl, indenyl, azulenyl, and the like, without being limited thereto. The carbocyclic aromatic group may be optionally substituted.

The term "aryloxy" is RO—, wherein R is aryl as defined above. The term "arylthio" is RS—, wherein R is the aryl as defined above.

As used herein, the term "cycloalkyl" refers to a monocyclic or polycyclic saturated ring having carbon and hydrogen atoms and no carbon-carbon multiple bonds. For example, the cycloalkyl group includes (C$_3$-C$_7$)cycloalkyl (e.g., cyclopropyl, cyclobutyl, cyclopentyl, cyclohexyl and cycloheptyl), without being limited thereto. The cycloalkyl group may be optionally substituted. In one embodiment, the cycloalkyl group is a monocyclic or bicyclic ring.

As used herein, the term "mono-alkylamino" refers to —NH(alkyl) including —NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, and the like, wherein the alkyl is as defined above.

As used herein, the term "di-alkylamino" refers to N(alkyl)(alkyl) including —N(CH$_3$)$_2$, —N(CH$_2$CH$_3$)$_2$, —N((CH$_2$)$_2$CH$_3$)$_2$, —N(CH$_3$)(CH$_2$CH$_3$), and the like, wherein each alkyl is alkyl as defined above.

As used herein, the term "alkylamino" is a concept that includes mono-alkylamino and di-alkylamino as defined above.

As used herein, the terms "carboxyl" and "carboxy" refer to —COOH.

As used herein, the term "aminoalkyl" refers to -(alkyl)-NH$_2$ including —CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$, and the like, wherein the alkyl is as defined above.

As used herein, the term "mono-alkylaminoalkyl" refers to -(alkyl)-NH(alkyl) including —CH$_2$—NH—CH$_3$, —CH$_2$—NHCH$_2$CH$_3$, —CH$_2$—NH(CH$_2$)$_2$CH$_3$, —CH$_2$—NH(CH$_2$)$_3$CH$_3$, —CH$_2$—NH(CH$_2$)$_4$CH$_3$, —CH$_2$—NH(CH$_2$)$_5$CH$_3$, —(CH$_2$)$_2$—NH—CH$_3$, and the like, wherein each alkyl is alkyl as defined above.

As used herein, "heteroaryl" is a 5- to 10-membered aromatic heterocyclic ring that has at least one heteroatom selected from the group consisting of nitrogen, oxygen, and sulfur and that includes a mono- or bicyclic ring system and at least one carbon atom. Representative heteroaryls include triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, tietanyl and oxazolyl.

As used herein, "heterocycle (heterorng)" refers to a saturated or unsaturated 5- to 7-membered monocyclic ring or a 7- to 10-membered bicyclic/heterocyclic ring containing 1 to 4 heteroatoms independently selected from nitrogen, oxygen and sulfur, wherein nitrogen and sulfur heteroatoms may be optionally oxidized, nitrogen heteroatoms may be optionally quaternized, and a bicyclic ring in which a part of the heterocycle is fused to a benzene ring is included. The heterocycle may be attached by heteroatoms or carbon atoms. The heterocycle includes the heteroaryl as defined above. Representative heterocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, and tetrahydrothiopyranyl.

"Heterocycle fused to phenyl" refers to a heterocycle attached to two adjacent carbon atoms of a phenyl ring, wherein the heterocycle is as defined above.

As used herein, the term "hydroxyalkyl" refers to an alkyl in which one or more hydrogen atoms are substituted with hydroxy and includes —CH$_2$OH, —CH$_2$CH$_2$OH, —(CH$_2$)$_2$CH$_2$OH, —(CH$_2$)$_3$CH$_2$OH, —(CH$_2$)$_4$CH$_2$OH, —(CH$_2$)$_5$CH$_2$OH, —CH(OH)—CH$_3$, —CH$_2$CH(OH)CH$_3$, and the like, wherein the alkyl is as defined above.

As used herein, the term "sulfonyl" refers to —SO$_3$H.

As used herein, the term "sulfonylalkyl" refers to —SO$_2$-(alkyl) including —SO$_2$—CH$_3$, —SO$_2$—CH$_2$CH$_3$, —SO$_2$—(CH$_2$)$_2$CH$_3$, —SO$_2$—(CH$_2$)$_3$CH$_3$, —SO$_2$—(CH$_2$)$_4$CH$_3$, and —SO$_2$—(CH$_2$)$_5$CH$_3$, wherein the alkyl is as defined above.

As used herein, the term "sulfinylalkyl" refers to —SO-(alkyl) including —SO—CH$_3$, —SO—CH$_2$CH$_3$, —SO—(CH$_2$)$_2$CH$_3$, —SO—(CH$_2$)$_3$CH$_3$, —SO—(CH$_2$)$_4$CH$_3$, —SO—(CH$_2$)$_5$CH$_3$, and the like, wherein the alkyl is as defined above.

"Thioalkyl" includes —S—CH$_3$, —S—CH$_2$CH$_3$, —S—(CH$_2$)$_2$CH$_3$, —S—(CH$_2$)$_3$CH$_3$, —S—(CH$_2$)$_4$CH$_3$, —S—(CH$_2$)$_5$CH$_3$, and the like, wherein the alkyl is as defined above.

As used herein, the term "substituted" indicates that the hydrogen atom of the moiety (e.g., alkyl, aryl, heteroaryl, heterocycle or cycloalkyl) to be replaced is replaced with a substituent. In one embodiment, each carbon atom of the substituted group is not substituted with two or more substituents. In another embodiment, each carbon atom of the substituted group is not substituted with one or more substituents. In the case of a keto substituent, two hydrogen atoms are substituted with oxygen attached to carbon by a double bond.

Unless otherwise specified with respect to a substituent, a halogen, hydroxyl, (lower) alkyl, haloalkyl, mono- or di-alkylamino, aryl, heterocycle, —NO$_2$, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —CN, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —NR$_a$SO$_2$R$_b$, —PO$_3$R$_a$, —PO(OR$_a$)(OR$_b$), —SO$_2$R$_a$, —S(O)R$_a$, —SO(NR$_a$)R$_b$ (e.g., sulfoximine), —S(NR$_a$)R$_b$ (e.g., sulfilimine) and —SR$_a$ may be used as substituents in the present disclosure, wherein R$_a$ and R$_b$ are the same or different and are each independently hydrogen, a halogen, amino, an alkyl, an alkoxyalkyl, a haloalkyl, aryl or a heterocycle, or may be in the form of a heterocycle containing attached nitrogen atoms. Here, R$_a$ and R$_b$ may be plural depending on the bonded atom.

As used herein, "basic structure of quinoline" refers to the following structure.

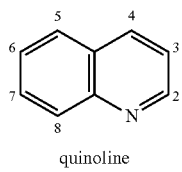
quinoline

According to the present disclosure, "pharmaceutically acceptable salts" include salts of active compounds prepared from relatively non-toxic acids and bases depending on particular substituents found in the compounds described herein. When the compounds of the present disclosure include relatively acidic functionality, base addition salts may be obtained by bringing the neutral forms of the compounds into contact with a sufficient amount of a desired base in a pure or suitable inert solvent. For example, pharmaceutically acceptable base addition salts include sodium, potassium, calcium, ammonium, organic amino or magnesium salts or similar salts. When the compounds of the present disclosure include relatively basic functionality, acid addition salts may be obtained by bringing the neutral forms of the compounds into contact with a sufficient amount of a desired acid in a pure or suitable inert solvent. For example, pharmaceutically acceptable acid addition salts include salts derived from relatively non-toxic organic acids including acetic acid, propionic acid, isobutylic acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and analogs thereof. In addition, the pharmaceutically acceptable acid addition salts include hydrogen chloride, hydrogen bromide, nitric acid, carbonic acid, monohydrogen carbonic acid, phosphoric acid, monohydrogen phosphoric acid, dihydrogen phosphoric acid, sulfuric acid, monohydrogensulfuric acid, hydrogen iodide or phosphorous acid and analogs thereof. In addition, the pharmaceutically acceptable acid addition salts include salts of amino acids such as arginate and analogs thereof and analogs of organic acids such as glucuronic or galacturonic acids and analogs thereof (e.g., Berge et al. (1977) J. Pharm. Sci. 66: 1-19). Certain compounds of the present disclosure have both basic and acidic functionalities to convert the compounds into base or acid addition salts. Other examples of salts are disclosed in documents (e.g., Remington's Pharmaceutical Sciences, 18$^{th}$ eds., Mack Publishing, Easton Pa. (1990) or Remington: The Science and Practice of Pharmacy, 19$^{th}$ eds., Mack Publishing, Easton Pa. (1995)) known in the art to which the present disclosure pertains.

As used herein, "effective dose" refers to an amount of the compounds of the present disclosure sufficient to destroy, modify, control or eliminate primary, localized or metastatic cancer cells or cancer tissues; to slow or minimize the spread of cancer; or to provide therapeutic benefits in treatment or management of cancer, neoplastic diseases, or tumors. In addition, "effective dose" refers to an amount of the compounds of the present disclosure sufficient to cause the death of neoplastic cells including cancer cells. In addition, "effective dose" refers to an amount of the compounds sufficient to inhibit or reduce c-Myc/Max/DNA complex formation either in vitro or in vivo.

As used herein, "inhibition of c-Myc/Max/DNA complex formation" indicates that, when compared to cells that are not exposed to the compounds of the present disclosure, the amount of c-Myc/Max/DNA complexes is decreased or the degree of binding of the c-Myc/Max heterodimer to DNA is suppressed or delayed in cells exposed to the compounds of the present disclosure.

As used herein, "preventive effective dose" refers to an amount of the compounds of the present disclosure sufficient to inhibit cancer development in patients susceptible to the recurrence, or spread of cancer, susceptible to cancer or patients previously exposed to a carcinogen. At this time, the type of patient is not limited thereto.

As used herein, the term "neoplastic" refers to an abnormal growth of cells or tissues (e.g., a boil) that may be benign or cancerous.

As used herein, "prevention" refers to preventing the recurrence, spread or onset of cancer in a patient.

As used herein, "treatment" includes eradication, removal, modification, or control of primary, localized or metastatic cancer tissues; and refers to minimizing or delaying the spread of cancer.

As used herein, the term "the compounds of the present disclosure" refers to compounds corresponding to each of Formula 1 (1a and 1b), Formula 2 (2a and 2b) and Formula 3 (3a and 3b), and also includes clathrates, hydrates, solvates, or polymorphs thereof. In addition, the term "the compounds of the present disclosure" also includes pharmaceutically acceptable salts of the compounds of the present disclosure, when pharmaceutically acceptable salts thereof are not mentioned. According to one embodiment, the compounds of the present disclosure may be present as stereomerically pure compounds (e.g., compounds that are substantially free of other stereoisomers (e.g., 85% ee or more, 90% ee or more, 95% ee or more, 97% ee or more, or 99% ee or more)). That is, in addition to the compounds corresponding to Formula 1, 2 or 3, when the salts of the compounds are tautomeric isomers and/or stereoisomers (e.g., geometrical isomers and conformational isomers), isolated isomers thereof and respective mixtures thereof are within the scope of the compounds of the present disclosure. When the compounds of the present disclosure or salts thereof have asymmetric carbons in the structure thereof, optically active compounds and racemic mixtures thereof are also within the scope of the compounds of the present disclosure. For example, as shown in the following scheme, when the compounds of the present disclosure have a sulfoxide (SOR) structure, the compounds may have chirality. The R and S forms of these isomers are included in the category of the compounds of the present disclosure, and the mixtures of the R and S forms are also included in the category of the compounds of the present disclosure.

Scheme 1

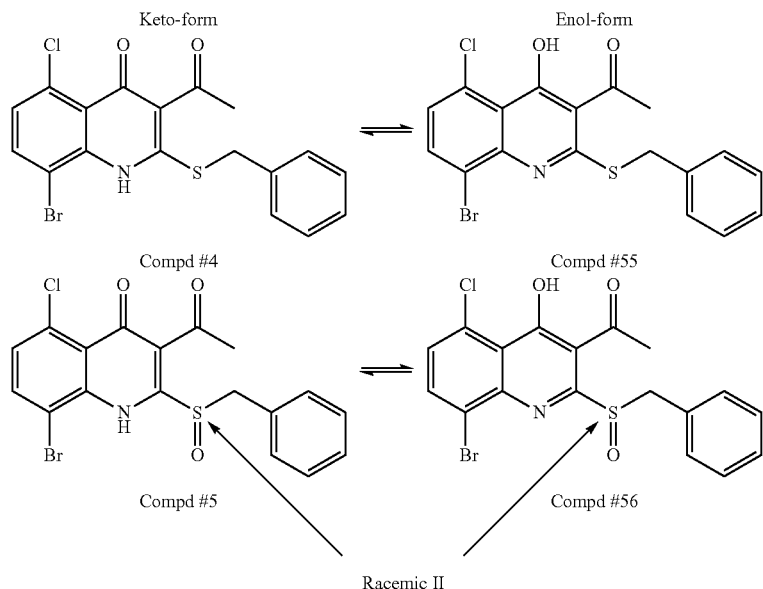

In addition, as shown in Scheme 1, the compounds of the present disclosure may exist in either keto or enol form, both of which are included in the category of the compounds of the present disclosure.

When used herein, the term "polymorph" refers to solid crystalline forms of the compounds of the present disclosure or complexes thereof. Different polymorphs of the same compound exhibit different physical, chemical and/or spectral characteristics. Differences in physical characteristics include stability (e.g., heat or light stability), compressibility and density (important for formulation and product production), and dissolution rate (which may affect bioavailability), without being limited thereto. Differences in stability cause changes in chemical reactivity (e.g., differential oxidation, as evidenced by more rapid color change when composed of one polymorph than when composed of another polymorph) or mechanical characteristics (e.g., as dynamically preferred polymorphs, stored tablet fragments are converted into more thermodynamically stable polymorphs), or both (tablets of one polymorph are more sensitive to degradation at high humidity). Other physical properties of polymorphs may affect processing thereof. For example, one polymorph may be more likely to form solvent compounds than another polymorph, e.g., due to a shape or particle size distribution thereof, or may be more difficult to filter or wash than another polymorph As used herein, the term "solvent compounds" refers to the compounds of the present disclosure or pharmaceutically acceptable salts thereof, including a stoichiometric or non-stoichiometric amount of a solvent bound by force between non-covalent molecules. Preferred solvents are volatile and non-toxic, and may be administered to humans in very small doses.

As used herein, the term "hydrates" refers to the compounds of the present disclosure or pharmaceutically acceptable salts thereof, including a stoichiometric or non-stoichiometric amount of water bound by force between non-covalent molecules.

As used herein, the term "clathrates" refers to the compounds of the present disclosure or salts thereof in the form of a crystal lattice including a space (e.g., channel) in which guest molecules (e.g., solvent or water) are confined.

When any compounds (prodrugs) isolated from the body are capable of producing the compounds of the present disclosure or salts thereof, such compounds are also within the scope of the present disclosure. As used herein, and unless otherwise indicated, the term "prodrugs" refer to the compounds of the present disclosure that are capable of undergoing hydrolysis, oxidation, or other reactions under biological conditions (in vitro or in vivo) to provide active compounds, particularly the compounds of the present disclosure. For example, prodrugs include biohydrolyzable compounds that are biodegraded to yield the compounds of the present disclosure, including biohydrolyzable portions such as biohydrolyzable amides, biohydrolyzable esters, biohydrolyzable carbamates, biohydrolyzable carbonates, biohydrolyzable ureides, and biohydrolyzable phosphate analogs, without being limited thereto. Preferably, prodrugs of compounds having a carboxyl group are lower alkyl esters of carboxylic acids. Carboxylic esters are typically formed by esterifying a portion of carboxylic acids present in the molecule. Prodrugs may be readily prepared using well known methods as described in the following documents: *Burger's Medicinal Chemistry and Drug Discovery* 6th ed. (Donald J. Abrahamed., 2001, Wiley) and *Design and Application of Prodrugs* (H. Bundgaard ed., 1985, Harwood Academic Publishers Gmfh).

As used herein, the term "purified" indicates that when a substance is separated, the purity of the substance is at least 90%. The purity of the substance may be at least 95% in one embodiment, 99% in another embodiment, and 99.9% in still another embodiment.

The term "hydrido" refers to a single —H atom (H), and may be interchanged with the symbol "H" or the term "hydrogen".

When substituents are described as being "optionally substituted", the substituents may be unsubstituted (1) or may be substituted with at least one of substituents as defined (2). When a substitutable position is not substituted, a default substituent is a hydrido radical.

As used herein, the singular forms "a" and "an" may include the plural forms unless context clearly dictates otherwise.

The term "pharmaceutically acceptable" means suitable for use as a pharmaceutical preparation and is generally considered to be safe for such use. In addition, pharmaceutically acceptable substances refer to substances which have been formally approved by the governing body of the State for such use or which are on the list of Korean Pharmacopoeia or US Pharmacopoeia.

Compounds of the Present Disclosure

The present disclosure provides compounds having the structures corresponding to Formula 1 (1a or 1b) below or pharmaceutically acceptable salts thereof:

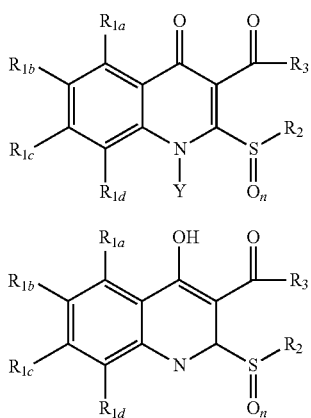

Formula 1a

Formula 1b in Formula 1, $R_{1a}$ to $R_{1d}$ are each independently hydrogen, a halogen, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{2-10}$ alkenyl, $C_{2-10}$ haloalkenyl, $C_{2-10}$ alkynyl, $C_{2-10}$ haloalkynyl, a hydroxyl group, nitro, cyano, $C_{1-6}$ alkoxycarbonyl, amino, $C_{1-6}$ alkylamino, di($C_{1-6}$ alkyl)amino, amino($C_{1-6}$)alkyl, ($C_{1-6}$)alkylamino($C_{1-6}$)alkyl, $C_{1-6}$ alkanoyl, $C_{3-7}$ cycloalkyl, an aryl, a heterocycle, or a heteroaryl, wherein $R_{1a}$ to $R_{1d}$ may be each independently unsubstituted or optionally substituted;

$R_2$ is hydrogen, $C_{1-6}$ alkyl, ($C_{1-6}$)alkoxy($C_{1-6}$)alkyl, $C_{1-6}$ haloalkyl, $C_{1-6}$ hydroxyalkyl, $C_{1-6}$ alkoxy, $C_{1-6}$ haloalkoxy, $C_{2-10}$ alkenyl, $C_{2-10}$ alkenyl carboxy, $C_{2-10}$ haloalkenyl, $C_{2-10}$ alkynyl, $C_{2-10}$ haloalkynyl, a hydroxyl group, nitro, cyano, $C_{1-6}$ alkoxycarbonyl, amino, $C_{1-6}$ alkylamino, $C_{1-6}$ cyanoalkyl, di($C_{1-6}$ alkyl)amino, amino($C_{1-6}$)alkyl, ($C_{1-6}$)alkylamino($C_{1-6}$)alkyl, $C_{1-6}$ alkanoyl, $C_{3-7}$ cycloalkyl, ($C_{1-6}$)alkyl($C_{3-7}$)cycloalkyl, an aryl, ($C_{1-6}$)alkylaryl, ($C_{1-6}$) haloalkylaryl, ($C_{2-6}$)alkenylamide($C_{1-6}$)alkylalkoxy, a heterocycle, ($C_{1-6}$)alkylheterocycle, a heteroaryl, or ($C_{1-6}$)alkylheteroaryl, wherein $R_2$ may be unsubstituted or optionally substituted;

$R_3$ is $C_{1-4}$ alkyl, isoalkyl, cycloalkyl, phenyl, or $C_{1-4}$ haloalkyl;

n is an integer from 0 to 2; and

Y is hydrogen, an alkyl, a haloalkyl, —C(O)alkyl, —C(O)aryl, a sulfonylalkyl, a sulfonylaryl, an aryl, or an alkylaryl, wherein an alkyl has 1 to 10 carbon atoms, preferably 1 to 4 carbon atoms, and an aryl may be unsubstituted or optionally substituted.

In another embodiment, the present disclosure provides compounds having the structures of Formula 2 (2a or 2b) or pharmaceutically acceptable salts thereof:

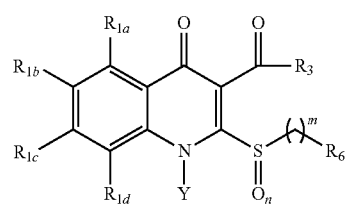

Formula 2a

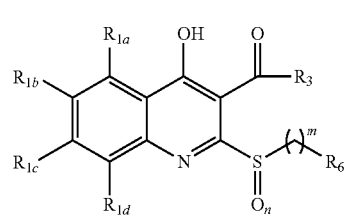

Formula 2b in Formula 2, $R_{1a}$ to $R_{1d}$, $R_3$, n and Y are as defined in Formula 1;

m is an integer from 0 to 4; and $R_6$ is phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, 1,2,5-oxadiazole, pyrrolo[2,3-b]pyridine, or benzothiophene, which may be unsubstituted or may be optionally substituted with one or more of hydrogen, $C_{1-6}$ alkyl, $C_{1-6}$ haloalkyl, $C_{1-6}$ alkoxy, a halogen or may be optionally substituted with one or more of hydrogen, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene or may be substituted with unsubstituted phenyl.

In another embodiment, the present disclosure provides compounds having the structures corresponding to Formula 3a or 3b or pharmaceutically acceptable salts thereof:

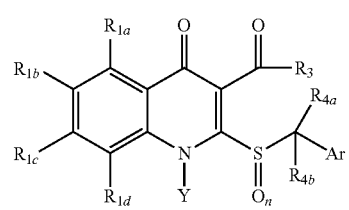

Formula 3a

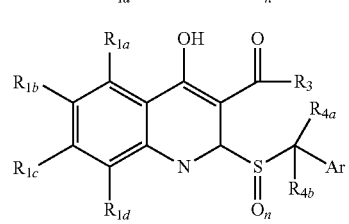

Formula 3b in Formula 3, $R_{1a}$ to $R_{1d}$, $R_3$, and n are as defined in Formula 1;

$R_{4a}$ and $R_{4b}$ are each independently hydrogen, a halogen, $C_{1-4}$ alkyl, $C_{1-4}$ haloalkyl, or $C_{1-4}$ alkyl in which one or more hydrogens are substituted with substituents other than halogen;

Ar is phenyl, heteroaryl being 5-6-membered and having heteroatoms selected independently from N, S, or O, or biheteroaryl being 8-12-membered and having heteroatoms selected independently from N, S, or O, wherein Ar may be unsubstituted or may be optionally substituted with one or more of a halogen, $C_{1-6}$ alkyl, $C_{1-6}$ alkylthio, $C_{1-6}$ haloalkyl, $C_{1-6}$ haloalkylthio, $C_{1-6}$ alkoxy, $C_{1-6}$ haloalkoxy, $C_{2-10}$ alkenyl, $C_{2-10}$ haloalkenyl, $C_{2-10}$ alkynyl, $C_{2-10}$ haloalkynyl, a hydroxyl group, COOH, nitro, cyano, $C_{1-6}$ alkoxycarbonyl, amino, $C_{1-6}$alkylamino, di($C_{1-6}$ alkyl)amino, amino($C_{1-6}$)alkyl, ($C_{1-6}$)alkylamino($C_{1-6}$) alkyl, ($C_{1-6}$)alkoxy($C_{1-6}$)alkylamino, ($C_{1-6}$)alkylamino ($C_{1-6}$) alkylamino, $C_{1-6}$ alkanoyl, $SF_5$, $S(O)CF_3$, $SCF_3$, NHC(=O)$CH_3$, C(=O)$NHCH_3$, $NHSO2CH3$, $C_{3-7}$ cycloalkyl, an aryl, benzoyl, a heterocycle, a heteroaryl, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, or benzothiophene, wherein the substituents of Ar may be unsubstituted or may be optionally substituted with one or more of CF3, a halogen, $(C_{1-3})$alkyl, $(C_{1-3})$haloalkyl, hydrogen, COOH, nitro, cyano, amino, di(C1-3 alkyl)amino, NHC(=O)CH3, or C(=O)NHCH3.

To obtain novel compounds having high inhibitory activity on c-Myc/Max/DNA complex formation, having high selectivity to c-Myc/Max/DNA complexes, and consequently having an inhibitory effect on cancer cells while having minimal side effects, the present inventors synthesized various compounds and performed various experiments to evaluate the compounds. As a result, the present inventors completed the present disclosure by confirming that the novel compounds of the present disclosure were suitable for the above-described various objects.

For example, a compound having a substituent linked to —S— at the 2-position of the basic structure of quinoline is superior in safety to a compound having a substituent linked to —NH—. Specifically, in the case of the compound having a substituent linked to —NH—, the compound is somewhat superior but has very severe cardiotoxicity. For example, in the case of a mouse xenograft model experiment using compound KSI-3716 of the following Formula 4, all of the experimental group (30 mpk, intraperitoneal administration (IP)) died. On the other hand, when the compounds of the present disclosure (e.g., Compound 4) were subjected to IV and IP single toxicity tests using 40 mpk, there were no deaths, no significant weight changes, and no abnormal symptoms in terms of general symptoms such as feed intake and drinking water intake.

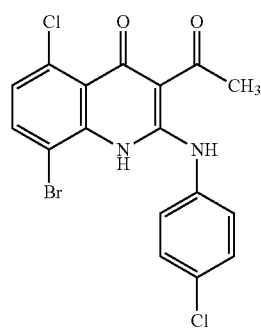

Formula 4

KSI-3716

TABLE 1

Single toxicity evaluation results of Compound 4 according to the present disclosure

| Species | Sex | Dose | Percentage |
| --- | --- | --- | --- |
| Mouse | Male | IV 40 mg/kg | 0 (0/2) |
| Mouse | Male | IP 40 mg/kg | 0 (0/2) |
| Mouse | Female | IV 40 mg/kg | 0 (0/2) |
| Mouse | Female | IP 40 mg/kg | 0 (0/2) |

No deaths were observed in single-dose administration of 40 mpk.

General symptoms: Feeding and drinking were good, and no other abnormal symptoms were observed.

Weight changes: In general, weight gain was observed, but weight gain was slightly reduced in certain individuals.

In the case of KSI-3716, all animals died at 30 mpk (IP).

In addition, in cardiotoxicity experiments using zebrafish, all zebrafish (n=10) died when 5 μM of a compound (e.g., KSI-3716 of Formula 4) having a substituent linked to —NH— was used. On the other hand, when the compounds of the present disclosure were used, lethality was very low and the compounds did not cause changes in heart rate. The experimental results of representative compounds are shown in the following Table 2.

TABLE 2

Changes in heart rate depending on treatment of compounds in zebrafish (mean, n = 10)

| Compounds | Changes in heart rate (%) | Lethality | Note |
| --- | --- | --- | --- |
| 10 μM Astemizole | 46.2 | 0/10 | |
| 5 μM of KSI-3716 | — | 10/10 | Not measurable by death of all zebrafish |
| 5 μM of Compound 4 | 88.5 | 1/10 | |
| 5 μM of Compound 33 | 97.3 | 0/10 | No significant heart rate inhibition |

In another example, $R_2$ linked to S at the 2-position of the basic structure of quinoline is preferably a phenyl structure in view of the various objects of the present disclosure. In addition, from the viewpoint of activity, it is preferable that the phenyl group is linked via —$CH_2$—, —$CH_2CH_2$—, —$CH_2CH_2CH_2$—, or —$CH_2CH_2CH_2CH_2$— as a bridge rather than directly linked to S. More preferably, —$CH_2$— or —$CH_2CH_2$— is used as a bridge.

For example, in view of activity, one or more of $R_{1a}$ to $R_{1d}$ are preferably substituted with substituents, more preferably halogens. In particular, when $R_{1a}$ and $R_{1d}$ were simultaneously substituted with halogens, even better activity was observed.

In the case of $R_3$, $C_{1-4}$ alkyl, isoalkyl, cycloalkyl, phenyl, or $C_{1-4}$ haloalkyl exhibited excellent activity. In particular, groups such as methyl or halomethyl exhibited better activity. In addition, when $R_3$ was —$CF_3$, metabolic stability was increased. On the other hand, when $R_3$ was heteroatoms of O or N, the activity desired in the present disclosure was weak.

In view of the various objects of the present disclosure, Y is preferably hydrogen.

$R_4$ ($R_{4a}$ and/or $R_{4b}$) is an important site for metabolic stability, and is preferably a lower alkyl or halogen for various objects of the present disclosure.

Non-limiting examples of the compounds according to the present disclosure include the compounds of Table 3 below and pharmaceutically acceptable salts thereof.

TABLE 3

| Compound Number | Structure | IUPAC Name |
|---|---|---|
| 1 | 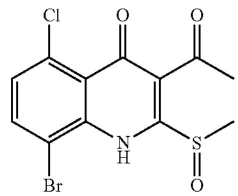 [SMILES: CC(=O)c1c(S(C)=O)[nH]c2c(Br)ccc(Cl)c2c1=O] | 3-acetyl-8-bromo-5-chloro-2-(methylsulfinyl)quinolin-4(1H)-one |
| 2 | 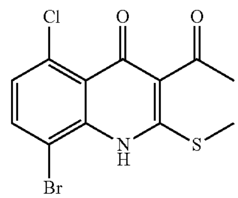 [SMILES: CSc1[nH]c2c(Br)ccc(Cl)c2c(=O)c1C(C)=O] | 3-acetyl-8-bromo-5-chloro-2-(methylthio)quinolin-4(1H)-one |
| 3 | 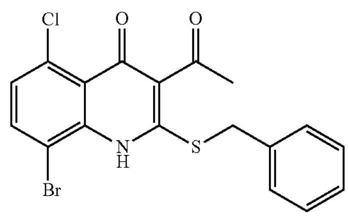 [SMILES: CC(=O)c1c(SCc2ccccc2)[nH]c2c(Br)ccc(Cl)c2c1=O] | 3-acetyl-2-(benzylthio)-8-bromo-5-chloroquinolin-4(1H)-one |
| 4 | 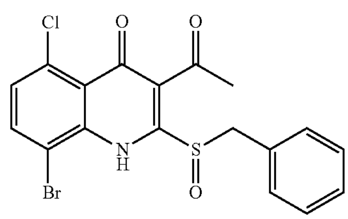 [SMILES: CC(=O)c1c(S(=O)Cc2ccccc2)[nH]c2c(Br)ccc(Cl)c2c1=O] | 3-acetyl-2-(benzylsulfinyl)-8-bromo-5-chloroquinolin-4(1H)-one |
| 5 | 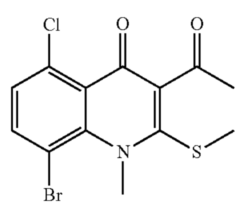 [SMILES: CSc1c(C(C)=O)c(=O)c2c(Cl)ccc(Br)c2n1C] | 3-acetyl-8-bromo-5-chloro-1-methyl-2-(methylthio)quinolin-4(1H)-one |
| 6 | 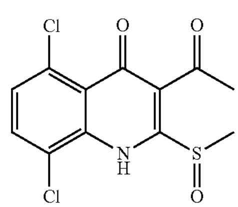 [SMILES: CC(=O)c1c(S(C)=O)[nH]c2c(Cl)ccc(Cl)c2c1=O] | 3-acetyl-5,8-dichloro-2-(methylsulfinyl)quinolin-4(1H)-one |
| 7 | 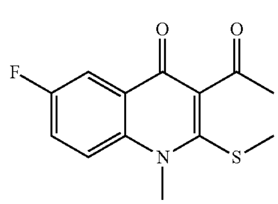 [SMILES: CSc1c(C(C)=O)c(=O)c2cc(F)ccc2n1C] | 3-acetyl-6-fluoro-1-methyl-2-(methylthio)quinolin-4(1H)-one |

TABLE 3-continued

| Compound Number | Structure | IUPAC Name |
| --- | --- | --- |
| 8 | 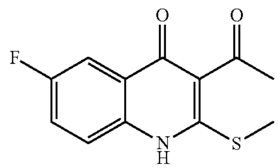 [SMILES: CSc1[nH]c2ccc(F)cc2c(=O)c1C(C)=O] | 1-(6-fluoro-4-hydroxy-2-(methylthio)quinolin-3-yl)ethan-1-one |
| 9 | 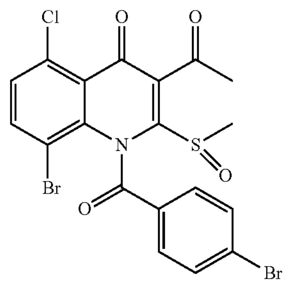 [SMILES: CC(=O)c1c(S(C)=O)n(C(=O)c2ccc(Br)cc2)c2c(Br)ccc(Cl)c2c1=O] | 3-acetyl-8-bromo-1-(4-bromobenzoyl)-5-chloro-2-(methylsulfinyl)quinolin-4(1H)-one |
| 10 | 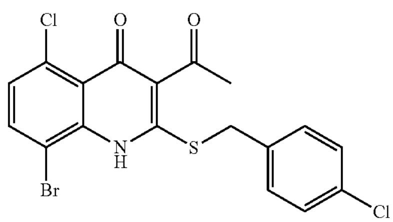 [SMILES: CC(=O)c1c(SCc2ccc(Cl)cc2)[nH]c2c(Br)ccc(Cl)c2c1=O] | 3-acetyl-8-bromo-5-chloro-2-((4-chlorobenzyl)thio)quinolin-4(1H)-one |
| 11 | 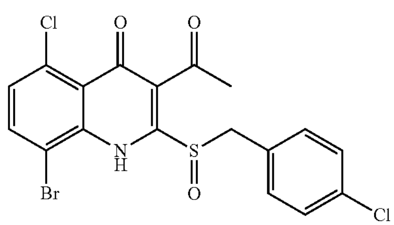 [SMILES: CC(=O)c1c(S(=O)Cc2ccc(Cl)cc2)[nH]c2c(Br)ccc(Cl)c2c1=O] | 3-acetyl-8-bromo-5-chloro-2-((4-chlorobenzyl)sulfinyl)quinolin-4(1H)-one |
| 12 | 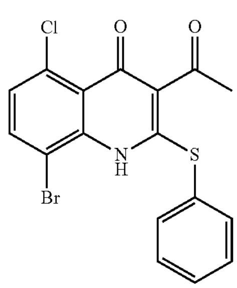 [SMILES: CC(=O)c1c(Sc2ccccc2)[nH]c2c(Br)ccc(Cl)c2c1=O] | 3-acetyl-8-bromo-5-chloro-2-(phenylthio)quinolin-4(1H)-one |
| 13 | 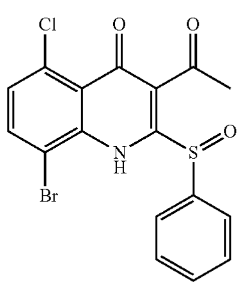 [SMILES: CC(=O)c1c(S(=O)c2ccccc2)[nH]c2c(Br)ccc(Cl)c2c1=O] | 3-acetyl-8-bromo-5-chloro-2-(phenylsulfinyl)quinolin-4(1H)-one |

TABLE 3-continued

| Compound Number | Structure | IUPAC Name |
|---|---|---|
| 14 | 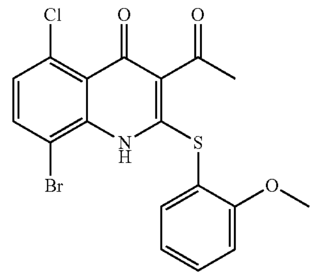 [SMILES: COc1ccccc1Sc1[nH]c2c(Br)ccc(Cl)c2c(=O)c1C(C)=O] | 3-acetyl-8-bromo-5-chloro-2-((2-methoxyphenyl)thio)quinolin-4(1H)-one |
| 15 | 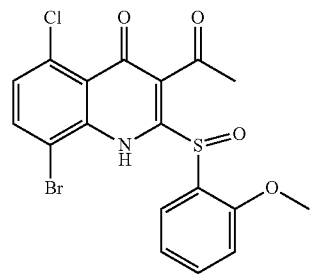 [SMILES: COc1ccccc1S(=O)c1[nH]c2c(Br)ccc(Cl)c2c(=O)c1C(C)=O] | 3-acetyl-8-bromo-5-chloro-2-((2-methoxyphenyl)sulfinyl)quinolin-4(1H)-one |
| 16 | 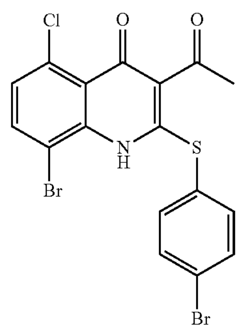 [SMILES: CC(=O)c1c(Sc2ccc(Br)cc2)[nH]c2c(Br)ccc(Cl)c2c1=O] | 3-acetyl-8-bromo-2-((4-bromophenyl)thio)-5-chloroquinolin-4(1H)-one |
| 17 | 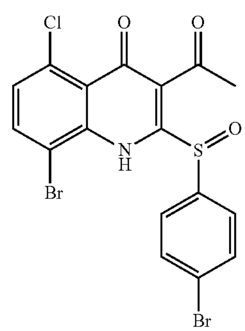 [SMILES: CC(=O)c1c(S(=O)c2ccc(Br)cc2)[nH]c2c(Br)ccc(Cl)c2c1=O] | 3-acetyl-8-bromo-2-((4-bromophenyl)sulfinyl)-5-chloroquinolin-4(1H)-one |
| 18 | 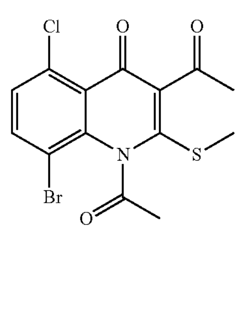 [SMILES: CSc1c(C(C)=O)c(=O)c2c(Cl)ccc(Br)c2n1C(C)=O] | 1,1'-(8-bromo-5-chloro-2-(methylthio)-4-oxoquinoline-1,3(4H)-diyl)bis(ethan-1-one) |

TABLE 3-continued

| Compound Number | Structure | IUPAC Name |
|---|---|---|
| 19 | 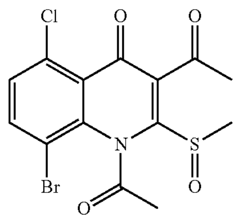 [SMILES: CC(=O)c1c(S(C)=O)n(C(C)=O)c2c(Br)ccc(Cl)c2c1=O] | 1,1'-(8-bromo-5-chloro-2-(methylsulfinyl)-4-oxoquinoline-1,3(4H)-diyl)bis(ethan-1-one) |
| 20 | 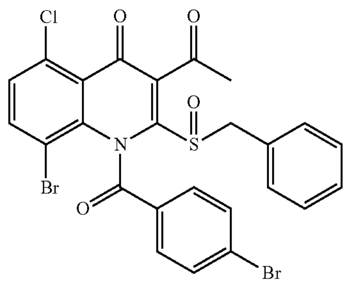 [SMILES: CC(=O)c1c(S(=O)Cc2ccccc2)n(C(=O)c2ccc(Br)cc2)c2c(Br)ccc(Cl)c2c1=O] | 3-acetyl-2-(benzylsulfinyl)-8-bromo-1-(4-bromobenzoyl)-5-chloroquinolin-4(1H)-one |
| 21 | 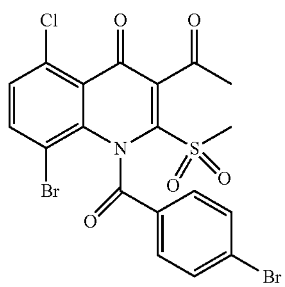 [SMILES: CC(=O)c1c(S(C)(=O)=O)n(C(=O)c2ccc(Br)cc2)c2c(Br)ccc(Cl)c2c1=O] | 3-acetyl-8-bromo-1-(4-bromobenzoyl)-5-chloro-2-(methylsulfonyl)quinolin-4(1H)-one |
| 22 | 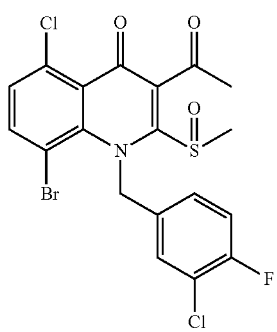 [SMILES: CC(=O)c1c(S(C)=O)n(Cc2ccc(F)c(Cl)c2)c2c(Br)ccc(Cl)c2c1=O] | 3-acetyl-8-bromo-5-chloro-1-(3-chloro-4-fluorobenzyl)-2-(methylsulfinyl)quinolin-4(1H)-one |
| 23 | 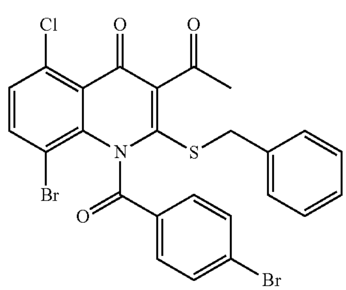 [SMILES: CC(=O)c1c(SCc2ccccc2)n(C(=O)c2ccc(Br)cc2)c2c(Br)ccc(Cl)c2c1=O] | 3-acetyl-2-(benzylthio)-8-bromo-1-(4-bromobenzoyl)-5-chloroquinolin-4(1H)-one |

TABLE 3-continued

| Compound Number | Structure | IUPAC Name |
|---|---|---|
| 24 | 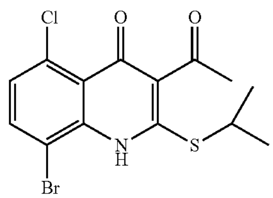 [SMILES: CC(=O)c1c(SC(C)C)[nH]c2c(Br)ccc(Cl)c2c1=O] | 3-acetyl-8-bromo-5-chloro-2-(isopropylthio)quinolin-4(1H)-one |
| 25 | 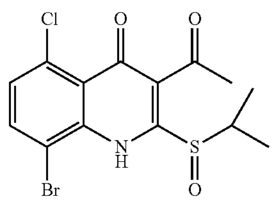 [SMILES: CC(=O)c1c(S(=O)C(C)C)[nH]c2c(Br)ccc(Cl)c2c1=O] | 3-acetyl-8-bromo-5-chloro-2-(isopropylsulfinyl)quinolin-4(1H)-one |
| 26 | 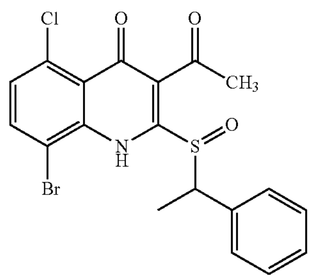 [SMILES: CC(=O)c1c(S(=O)C(C)c2ccccc2)[nH]c2c(Br)ccc(Cl)c2c1=O] | 3-acetyl-8-bromo-5-chloro-2-((1-phenylethyl)sulfinyl)quinolin-4(1H)-one |
| 27 | 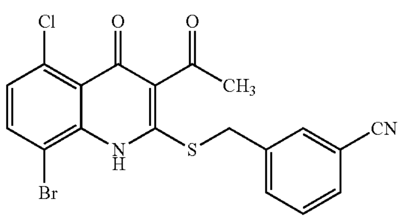 [SMILES: CC(=O)c1c(SCc2cccc(C#N)c2)[nH]c2c(Br)ccc(Cl)c2c1=O] | 3-(((3-acetyl-8-bromo-5-chloro-4-oxo-1,4-dihydroquinolin-2-yl)thio)methyl)benzonitrile |
| 28 | 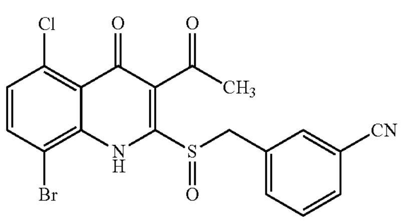 [SMILES: CC(=O)c1c(S(=O)Cc2cccc(C#N)c2)[nH]c2c(Br)ccc(Cl)c2c1=O] | 3-(((3-acetyl-8-bromo-5-chloro-4-oxo-1,4-dihydroquinolin-2-yl)sulfinyl)methyl)benzonitrile |
| 29 | 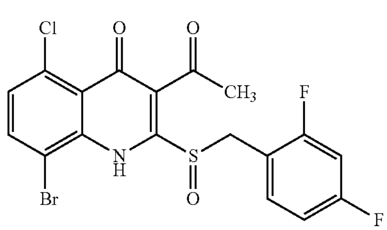 [SMILES: CC(=O)c1c(S(=O)Cc2ccc(F)cc2F)[nH]c2c(Br)ccc(Cl)c2c1=O] | 3-acetyl-8-bromo-5-chloro-2-((2,4-difluorobenzyl)sulfinyl)quinolin-4(1H)-one |
| 30 | 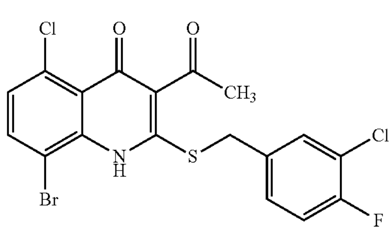 [SMILES: CC(=O)c1c(SCc2ccc(F)c(Cl)c2)[nH]c2c(Br)ccc(Cl)c2c1=O] | 3-acetyl-8-bromo-5-chloro-2-((3-chloro-4-fluorobenzyl)thio)quinolin-4(1H)-one |

TABLE 3-continued

| Compound Number | Structure | IUPAC Name |
|---|---|---|
| 31 | 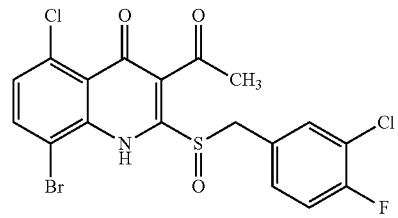 [SMILES: CC(=O)c1c(S(=O)Cc2ccc(F)c(Cl)c2)[nH]c2c(Br)ccc(Cl)c2c1=O] | 3-acetyl-8-bromo-5-chloro-2-((3-chloro-4-fluorobenzyl)sulfinyl)quinolin-4(1H)-one |
| 32 | 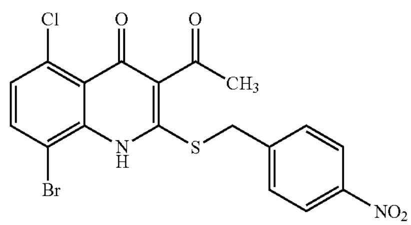 [SMILES: CC(=O)c1c(SCc2ccc([N+](=O)[O-])cc2)[nH]c2c(Br)ccc(Cl)c2c1=O] | 3-acetyl-8-bromo-5-chloro-2-((4-nitrobenzyl)thio)quinolin-4(1H)-one |
| 33 | 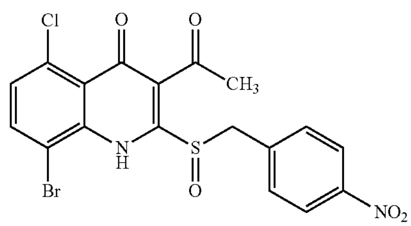 [SMILES: CC(=O)c1c(S(=O)Cc2ccc([N+](=O)[O-])cc2)[nH]c2c(Br)ccc(Cl)c2c1=O] | 3-acetyl-8-bromo-5-chloro-2-((4-nitrobenzyl)sulfinyl)quinolin-4(1H)-one |
| 34 | 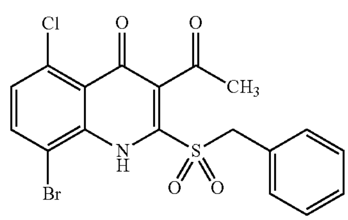 [SMILES: CC(=O)c1c(S(=O)(=O)Cc2ccccc2)[nH]c2c(Br)ccc(Cl)c2c1=O] | 3-acetyl-2-(benzylsulfonyl)-8-bromo-5-chloroquinolin-4(1H)-one |
| 35 | 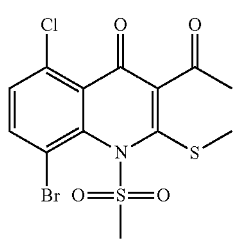 [SMILES: CSc1c(C(C)=O)c(=O)c2c(Cl)ccc(Br)c2n1S(C)(=O)=O] | 3-acetyl-8-bromo-5-chloro-1-(methylsulfonyl)-2-(methylthio)quinolin-4(1H)-one |
| 36 | 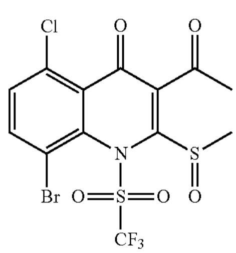 [SMILES: CC(=O)c1c(S(C)=O)n(S(=O)(=O)C(F)(F)F)c2c(Br)ccc(Cl)c2c1=O] | 3-acetyl-8-bromo-5-chloro-2-(methylsulfinyl)-1-((trifluoromethyl)sulfonyl)quinolin-4(1H)-one |

TABLE 3-continued

| Compound Number | Structure | IUPAC Name |
|---|---|---|
| 37 | 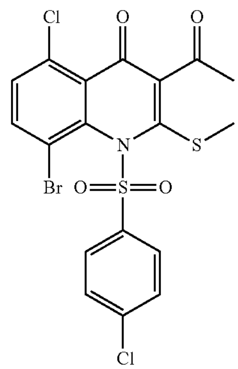 [SMILES: CSc1c(C(C)=O)c(=O)c2c(Cl)ccc(Br)c2n1S(=O)(=O)c1ccc(Cl)cc1] | 3-acetyl-8-bromo-5-chloro-1-((4-chlorophenyl)sulfonyl)-2-(methylthio)quinolin-4(1H)-one |
| 38 | 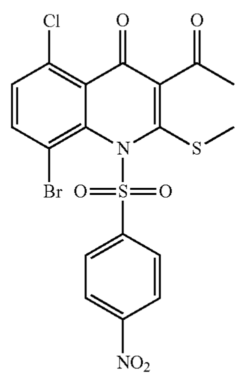 [SMILES: CSc1c(C(C)=O)c(=O)c2c(Cl)ccc(Br)c2n1S(=O)(=O)c1ccc([N+](=O)[O-])cc1] | 3-acetyl-8-bromo-5-chloro-2-(methylthio)-1-((4-nitrophenyl)sulfonyl)quinolin-4(1H)-one |
| 39 | 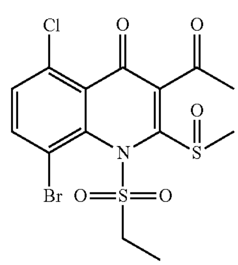 [SMILES: CCS(=O)(=O)n1c(S(C)=O)c(C(C)=O)c(=O)c2c(Cl)ccc(Br)c21] | 3-acetyl-8-bromo-5-chloro-1-(ethylsulfonyl)-2-(methylsulfinyl)quinolin-4(1H)-one |
| 40 | 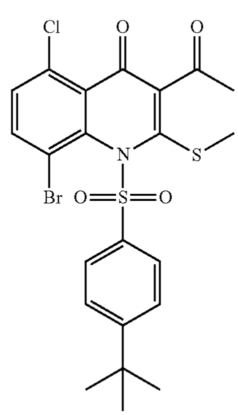 [SMILES: CSc1c(C(C)=O)c(=O)c2c(Cl)ccc(Br)c2n1S(=O)(=O)c1ccc(C(C)(C)C)cc1] | 3-acetyl-8-bromo-1-((4-(tert-butyl)phenyl)sulfonyl)-5-chloro-2-(methylthio)quinolin-4(1H)-one |

TABLE 3-continued
| Compound Number | Structure | IUPAC Name |
|---|---|---|
| 41 | 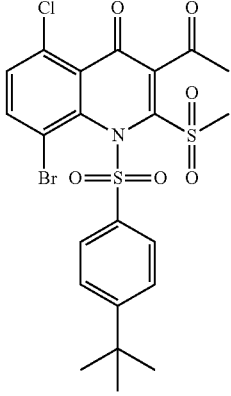 [SMILES: CC(=O)c1c(S(C)(=O)=O)n(S(=O)(=O)c2ccc(C(C)(C)C)cc2)c2c(Br)ccc(Cl)c2c1=O] | 3-acetyl-8-bromo-1-((4-(tert-butyl)phenyl)sulfonyl)-5-chloro-2-(methylsulfonyl)quinolin-4(1H)-one |
| 42 | 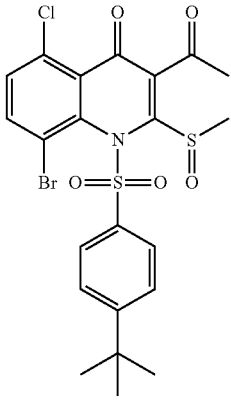 [SMILES: CC(=O)c1c(S(C)=O)n(S(=O)(=O)c2ccc(C(C)(C)C)cc2)c2c(Br)ccc(Cl)c2c1=O] | 3-acetyl-8-bromo-1-((4-(tert-butyl)phenyl)sulfonyl)-5-chloro-2-(methylsulfinyl)quinolin-4(1H)-one |
| 43 | 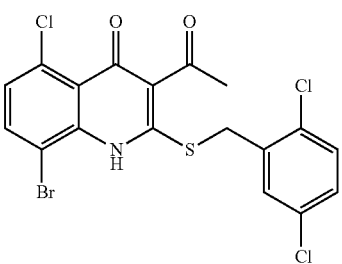 [SMILES: CC(=O)c1c(SCc2cc(Cl)ccc2Cl)[nH]c2c(Br)ccc(Cl)c2c1=O] | 3-acetyl-8-bromo-5-chloro-2-((2,5-dichlorobenzyl)thio)quinolin-4(1H)-one |
| 44 | 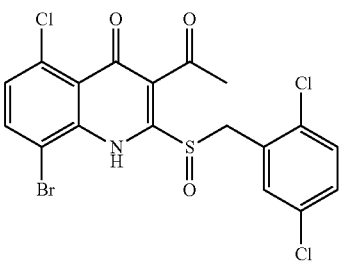 [SMILES: CC(=O)c1c(S(=O)Cc2cc(Cl)ccc2Cl)[nH]c2c(Br)ccc(Cl)c2c1=O] | 3-acetyl-8-bromo-5-chloro-2-((2,5-dichlorobenzyl)sulfinyl)quinolin-4(1H)-one |

TABLE 3-continued

| Compound Number | Structure | IUPAC Name |
|---|---|---|
| 45 | 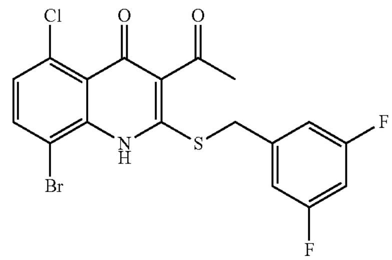 [SMILES: CC(=O)c1c(SCc2cc(F)cc(F)c2)[nH]c2c(Br)ccc(Cl)c2c1=O] | 3-acetyl-8-bromo-5-chloro-2-((3,5-difluorobenzyl)thio)quinolin-4(1H)-one |
| 46 | 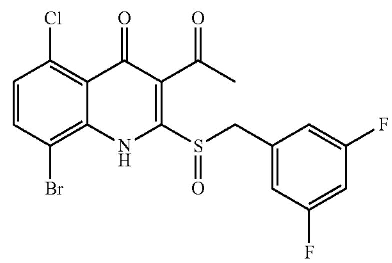 [SMILES: CC(=O)c1c(S(=O)Cc2cc(F)cc(F)c2)[nH]c2c(Br)ccc(Cl)c2c1=O] | 3-acetyl-8-bromo-5-chloro-2-((3,5-difluorobenzyl)sulfinyl)quinolin-4(1H)-one |
| 47 | 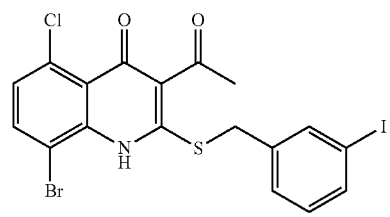 [SMILES: CC(=O)c1c(SCc2cccc(I)c2)[nH]c2c(Br)ccc(Cl)c2c1=O] | 3-acetyl-8-bromo-5-chloro-2-((3-iodobenzyl)thio)quinolin-4(1H)-one |
| 48 | 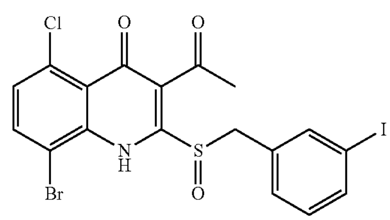 [SMILES: CC(=O)c1c(S(=O)Cc2cccc(I)c2)[nH]c2c(Br)ccc(Cl)c2c1=O] | 3-acetyl-8-bromo-5-chloro-2-((3-iodobenzyl)sulfinyl)quinolin-4(1H)-one |
| 49 | 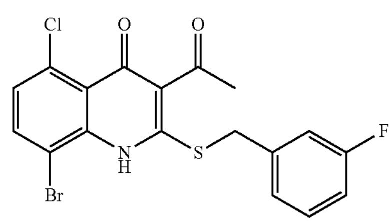 [SMILES: CC(=O)c1c(SCc2cccc(F)c2)[nH]c2c(Br)ccc(Cl)c2c1=O] | 3-acetyl-8-bromo-5-chloro-2-((3-fluorobenzyl)thio)quinolin-4(1H)-one |
| 50 | 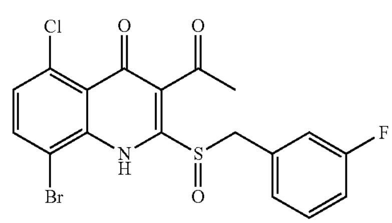 [SMILES: CC(=O)c1c(S(=O)Cc2cccc(F)c2)[nH]c2c(Br)ccc(Cl)c2c1=O] | 3-acetyl-8-bromo-5-chloro-2-((3-fluorobenzyl)sulfinyl)quinolin-4(1H)-one |

TABLE 3-continued

| Compound Number | Structure | IUPAC Name |
|---|---|---|
| 51 | 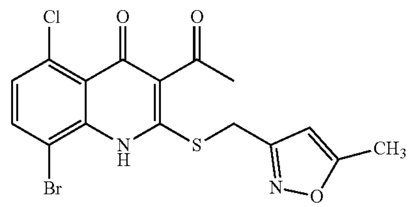 [SMILES: CC(=O)c1c(SCc2cc(C)on2)[nH]c2c(Br)ccc(Cl)c2c1=O] | 3-acetyl-8-bromo-5-chloro-2-(((5-methylisoxazol-3-yl)methyl)sulfinyl)quinolin-4(1H)-one |
| 52 | 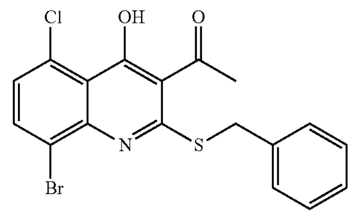 [SMILES: CC(=O)c1c(SCc2ccccc2)nc2c(Br)ccc(Cl)c2c1O] | 1-(2-(benzylthio)-8-bromo-5-chloro-4-hydroxyquinolin-3-yl)ethan-1-one |
| 53 | 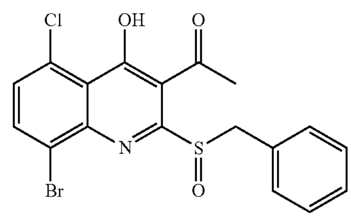 [SMILES: CC(=O)c1c(S(=O)Cc2ccccc2)nc2c(Br)ccc(Cl)c2c1O] | 1-(2-(benzylsulfinyl)-8-bromo-5-chloro-4-hydroxyquinolin-3-yl)ethan-1-one |
| 54 | 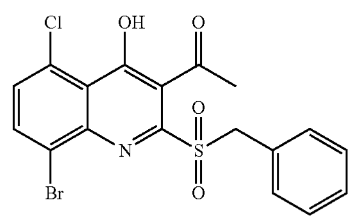 [SMILES: CC(=O)c1c(S(=O)(=O)Cc2ccccc2)nc2c(Br)ccc(Cl)c2c1O] | 1-(2-(benzylsulfonyl)-8-bromo-5-chloro-4-hydroxyquinolin-3-yl)ethan-1-one |
| 55 | 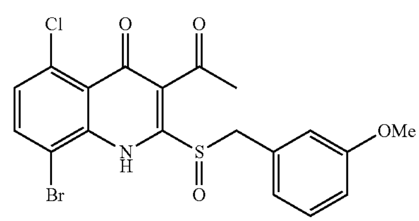 [SMILES: COc1cccc(CS(=O)c2[nH]c3c(Br)ccc(Cl)c3c(=O)c2C(C)=O)c1] | 3-acetyl-8-bromo-5-chloro-2-((3-methoxybenzyl)sulfinyl)quinolin-4(1H)-one |
| 56 | 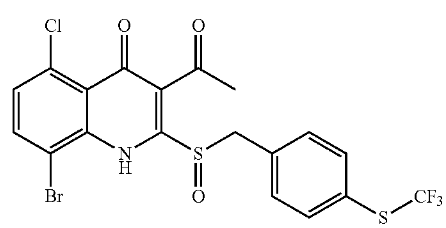 [SMILES: CC(=O)c1c(S(=O)Cc2ccc(SC(F)(F)F)cc2)[nH]c2c(Br)ccc(Cl)c2c1=O] | 3-acetyl-8-bromo-5-chloro-2-(((4-((trifluoromethyl)thio)benzyl)sulfinyl)quinolin-4(1H)-one |
| 57 | 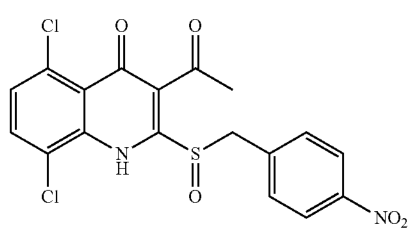 [SMILES: CC(=O)c1c(S(=O)Cc2ccc([N+](=O)[O-])cc2)[nH]c2c(Cl)ccc(Cl)c2c1=O] | 3-acetyl-5,8-dichloro-2-((4-nitrobenzyl)sulfinyl)quinolin-4(1H)-one |

TABLE 3-continued

| Compound Number | Structure | IUPAC Name |
|---|---|---|
| 58 | 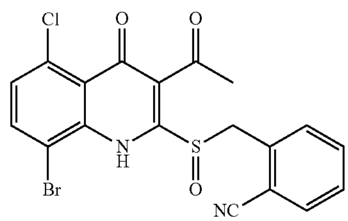 [SMILES: CC(=O)c1c(S(=O)Cc2ccccc2C#N)[nH]c2c(Br)ccc(Cl)c2c1=O] | 2-(((3-acetyl-8-bromo-5-chloro-4-oxo-1,4-dihydroquinolin-2-yl)sulfinyl)methyl)benzonitrile |
| 59 | 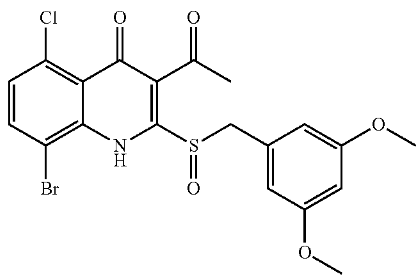 [SMILES: COc1cc(CS(=O)c2[nH]c3c(Br)ccc(Cl)c3c(=O)c2C(C)=O)cc(OC)c1] | 3-acetyl-8-bromo-5-chloro-2-((3,5-dimethoxybenzyl)sulfinyl)quinolin-4(1H)-one |
| 60 | 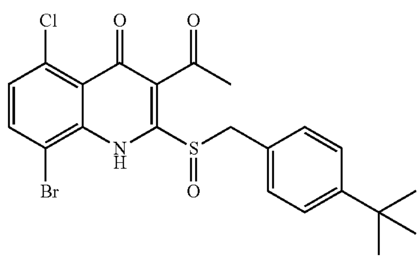 [SMILES: CC(=O)c1c(S(=O)Cc2ccc(C(C)(C)C)cc2)[nH]c2c(Br)ccc(Cl)c2c1=O] | 3-acetyl-8-bromo-2-((4-(tert-butyl)benzyl)sulfinyl)-5-chloroquinolin-4(1H)-one |
| 61 | 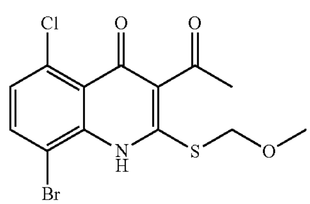 [SMILES: COCSc1[nH]c2c(Br)ccc(Cl)c2c(=O)c1C(C)=O] | 3-acetyl-8-bromo-5-chloro-2-((methoxymethyl)thio)quinolin-4(1H)-one |
| 62 | 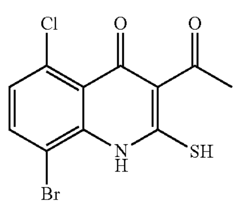 [SMILES: CC(=O)c1c(S)[nH]c2c(Br)ccc(Cl)c2c1=O] | 3-acetyl-8-bromo-5-chloro-2-mercaptoquinolin-4(1H)-one |
| 63 | 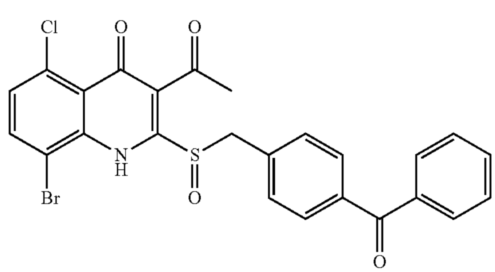 [SMILES: CC(=O)c1c(S(=O)Cc2ccc(C(=O)c3ccccc3)cc2)[nH]c2c(Br)ccc(Cl)c2c1=O] | 3-acetyl-2-((4-benzoylbenzyl)sulfinyl)-8-bromo-5-chloroquinolin-4(1H)-one |

TABLE 3-continued

| Compound Number | Structure | IUPAC Name |
|---|---|---|
| 64 | 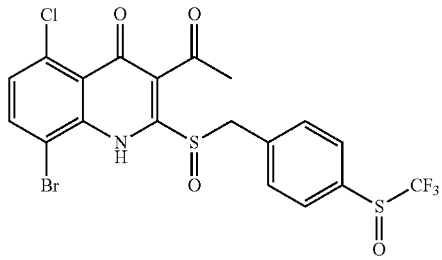 [SMILES: CC(=O)c1c(S(=O)Cc2ccc(S(=O)C(F)(F)F)cc2)[nH]c2c(Br)ccc(Cl)c2c1=O] | 3-acetyl-8-bromo-5-chloro-2-((4-((trifluoromethyl)sulfinyl)benzyl)sulfinyl)quinolin-4(1H)-one |
| 65 | 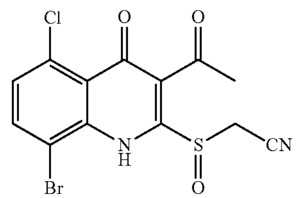 [SMILES: CC(=O)c1c(S(=O)CC#N)[nH]c2c(Br)ccc(Cl)c2c1=O] | 2-((3-acetyl-8-bromo-5-chloro-4-oxo-1,4-dihydroquinolin-2-yl)sulfinyl)acetonitrile |
| 66 | 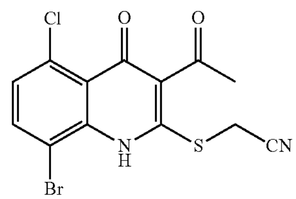 [SMILES: CC(=O)c1c(SCC#N)[nH]c2c(Br)ccc(Cl)c2c1=O] | 2-((3-acetyl-8-bromo-5-chloro-4-oxo-1,4-dihydroquinolin-2-yl)thio)acetonitrile |
| 67 | 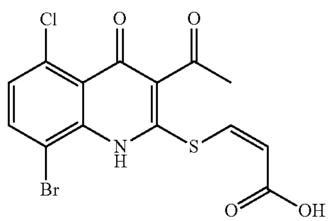 [SMILES: CC(=O)c1c(S/C=C\C(=O)O)[nH]c2c(Br)ccc(Cl)c2c1=O] | (Z)-3-((3-acetyl-8-bromo-5-chloro-4-oxo-1,4-dihydroquinolin-2-yl)thio)acrylic acid |
| 68 | 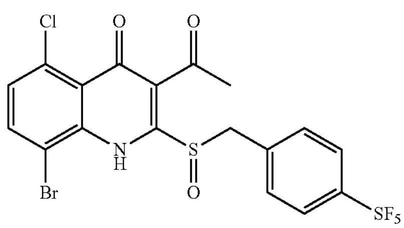 | 3-acetyl-8-bromo-5-chloro-2-((4-(pentafluoro-l6-sulfanyl)benzyl)sulfinyl)quinolin-4(1H)-one |
| 69 | 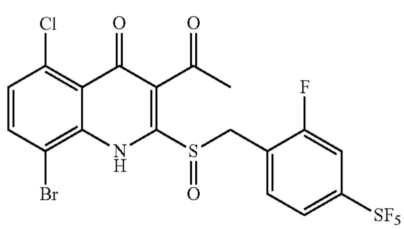 | 3-acetyl-8-bromo-5-chloro-2-((2-fluoro-4-(pentafluoro-l6-sulfanyl)benzyl)sulfinyl)quinolin-4(1H)-one |
| 70 | 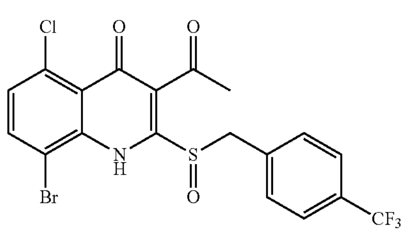 [SMILES: CC(=O)c1c(S(=O)Cc2ccc(C(F)(F)F)cc2)[nH]c2c(Br)ccc(Cl)c2c1=O] | 3-acetyl-8-bromo-5-chloro-2-((4-(trifluoromethyl)benzyl)sulfinyl)quinolin-4(1H)-one |

TABLE 3-continued

| Compound Number | Structure | IUPAC Name |
|---|---|---|
| 71 | 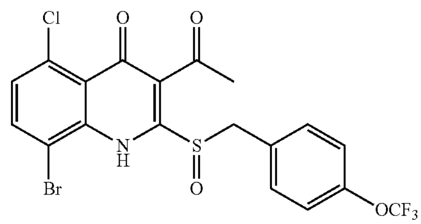 [SMILES: CC(=O)c1c(S(=O)Cc2ccc(OC(F)(F)F)cc2)[nH]c2c(Br)ccc(Cl)c2c1=O] | 3-acetyl-8-bromo-5-chloro-2-((4-(trifluoromethoxy)benzyl)sulfinyl)quinolin-4(1H)-one |
| 72 | 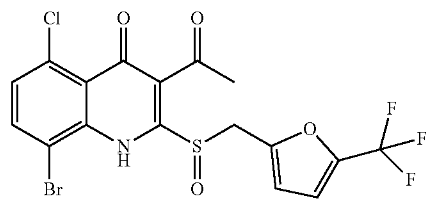 [SMILES: CC(=O)c1c(S(=O)Cc2ccc(C(F)(F)F)o2)[nH]c2c(Br)ccc(Cl)c2c1=O] | 3-acetyl-8-bromo-5-chloro-2-(((5-(trifluoromethyl)furan-2-yl)methyl)sulfinyl)quinolin-4(1H)-one |
| 73 | 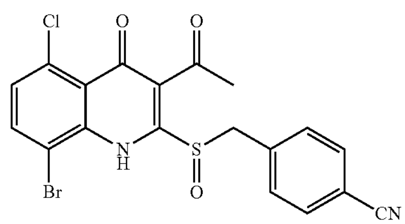 [SMILES: CC(=O)c1c(S(=O)Cc2ccc(C#N)cc2)[nH]c2c(Br)ccc(Cl)c2c1=O] | 4-(((3-acetyl-8-bromo-5-chloro-4-oxo-1,4-dihydroquinolin-2-yl)sulfinyl)methyl)benzonitrile |
| 74 | 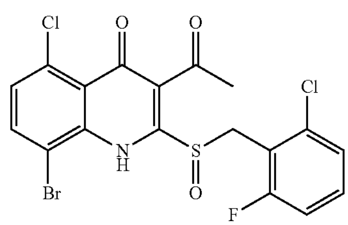 [SMILES: CC(=O)c1c(S(=O)Cc2c(F)cccc2Cl)[nH]c2c(Br)ccc(Cl)c2c1=O] | 3-acetyl-8-bromo-5-chloro-2-((2-chloro-6-fluorobenzyl)sulfinyl)quinolin-4(1H)-one |
| 75 | 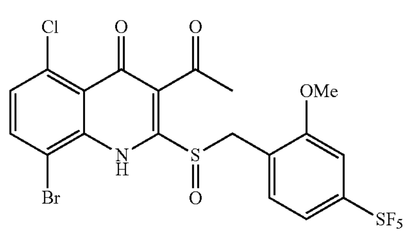 | 3-acetyl-8-bromo-5-chloro-2-((2-methoxy-4-(pentafluoro-λ6-sulfanyl)benzyl)sulfinyl)quinolin-4(1H)-one |
| 76 | 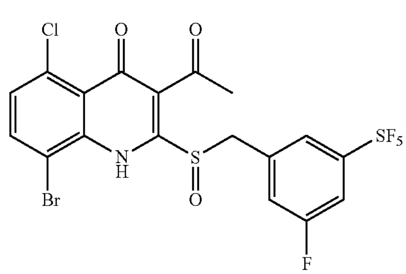 | 3-acetyl-8-bromo-5-chloro-2-((3-fluoro-5-(pentafluoro-λ6-sulfanyl)benzyl)sulfinyl)quinolin-4(1H)-one |

TABLE 3-continued

| Compound Number | Structure | IUPAC Name |
|---|---|---|
| 77 | 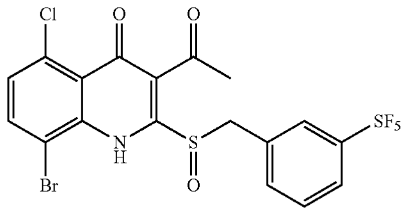 | 3-acetyl-8-bromo-5-chloro-2-((3-(pentafluoro-λ6-sulfanyl)benzyl)sulfinyl)quinolin-4(1H)-one |
| 78 | 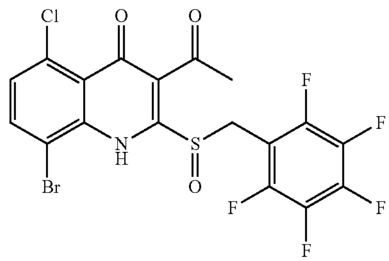 [SMILES: CC(=O)c1c(S(=O)Cc2c(F)c(F)c(F)c(F)c2F)[nH]c2c(Br)ccc(Cl)c2c1=O] | 3-acetyl-8-bromo-5-chloro-2-(((perfluorophenyl)methyl)sulfinyl)quinolin-4(1H)-one |
| 79 | 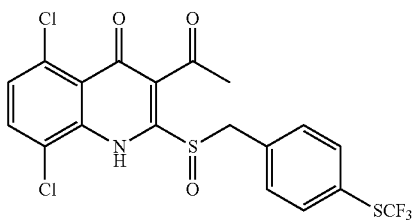 | 3-acetyl-5,8-dichloro-2-((4-((trifluoromethyl)thio)benzyl)sulfinyl)quinolin-4(1H)-one |
| 80 | 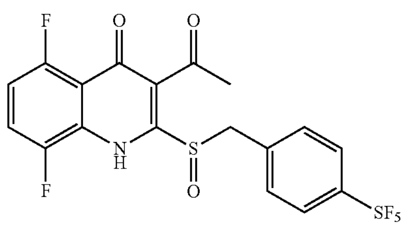 | 3-acetyl-5,8-difluoro-2-((4-(pentafluoro-λ6-sulfanyl)benzyl)sulfinyl)quinolin-4(1H)-one |
| 81 | 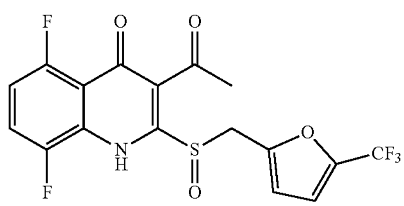 [SMILES: CC(=O)c1c(S(=O)Cc2ccc(C(F)(F)F)o2)[nH]c2c(F)ccc(F)c2c1=O] | 3-acetyl-5,8-difluoro-2-(((5-(trifluoromethyl)furan-2-yl)methyl)sulfinyl)quinolin-4(1H)-one |
| 82 | 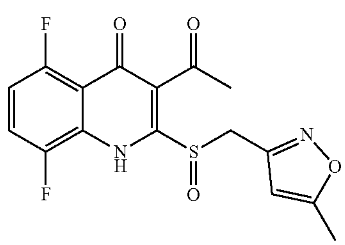 [SMILES: CC(=O)c1c(S(=O)Cc2cc(C)on2)[nH]c2c(F)ccc(F)c2c1=O] | 3-acetyl-5,8-difluoro-2-(((5-methylisoxazol-3-yl)methyl)sulfinyl)quinolin-4(1H)-one |

TABLE 3-continued

| Compound Number | Structure | IUPAC Name |
|---|---|---|
| 83 | 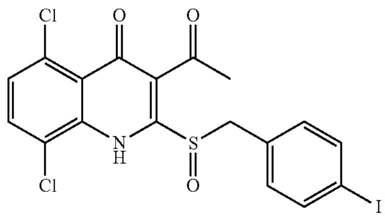 [SMILES: CC(=O)c1c(S(=O)Cc2ccc(I)cc2)[nH]c2c(Cl)ccc(Cl)c2c1=O] | 3-acetyl-5,8-dichloro-2-((4-iodobenzyl)sulfinyl)quinolin-4(1H)-one |
| 84 | 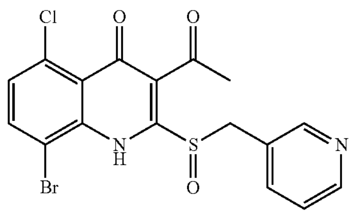 [SMILES: CC(=O)c1c(S(=O)Cc2cccnc2)[nH]c2c(Br)ccc(Cl)c2c1=O] | 3-acetyl-8-bromo-5-chloro-2-((pyridin-3-ylmethyl)sulfinyl)quinolin-4(1H)-one |
| 85 | 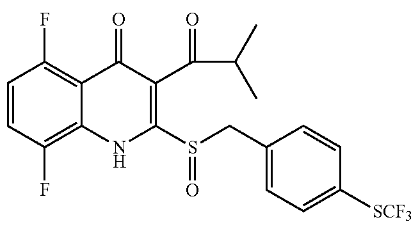 | 5,8-difluoro-3-isobutyryl-2-((4-((trifluoromethyl)thio)benzyl)sulfinyl)quinolin-4(1H)-one |
| 86 | 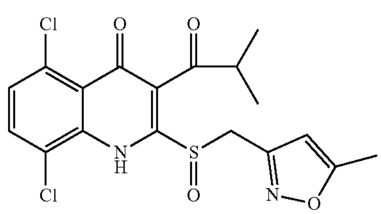 [SMILES: Cc1cc(CS(=O)c2[nH]c3c(Cl)ccc(Cl)c3c(=O)c2C(=O)C(C)C)no1] | 5,8-dichloro-3-isobutyryl-2-(((5-methylisoxazol-3-yl)methyl)sulfinyl)quinolin-4(1H)-one |
| 87 | 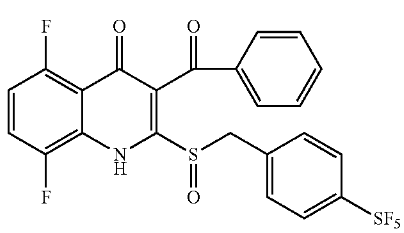 | 3-benzoyl-5,8-difluoro-2-((4-(pentafluoro-λ6-sulfanyl)benzyl)sulfinyl)quinolin-4(1H)-one |
| 88 | 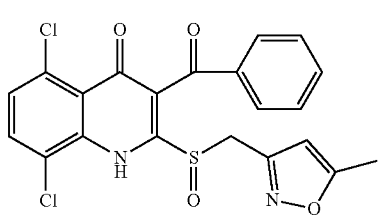 [SMILES: Cc1cc(CS(=O)c2[nH]c3c(Cl)ccc(Cl)c3c(=O)c2C(=O)c2ccccc2)no1] | 3-benzoyl-5,8-dichloro-2-(((5-methylisoxazol-3-yl)methyl)sulfinyl)quinolin-4(1H)-one |

TABLE 3-continued

| Compound Number | Structure | IUPAC Name |
|---|---|---|
| 89 | 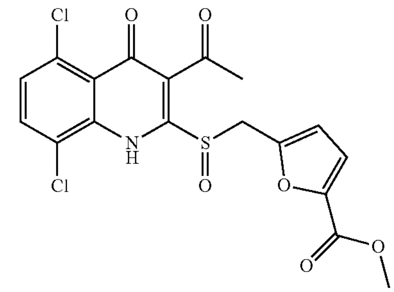 [SMILES: COC(=O)c1ccc(CS(=O)c2[nH]c3c(Cl)ccc(Cl)c3c(=O)c2C(C)=O)o1] | methyl 5-(((3-acetyl-5,8-dichloro-4-oxo-1,4-dihydroquinolin-2-yl)sulfinyl)methyl)furan-2-carboxylate |
| 90 | 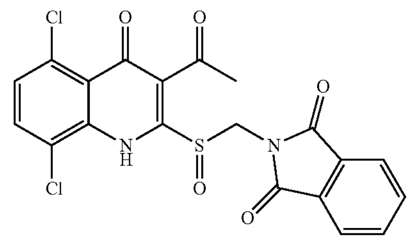 [SMILES: CC(=O)c1c(S(=O)CN2C(=O)c3ccccc3C2=O)[nH]c2c(Cl)ccc(Cl)c2c1=O] | 2-(((3-acetyl-5,8-dichloro-4-oxo-1,4-dihydroquinolin-2-yl)sulfinyl)methyl)isoindoline-1,3-dione |
| 91 | 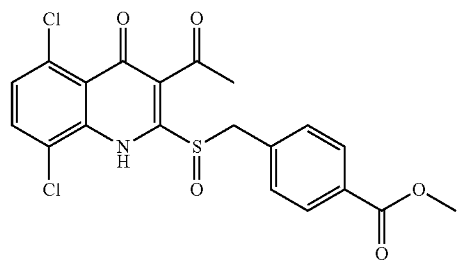 [SMILES: COC(=O)c1ccc(CS(=O)c2[nH]c3c(Cl)ccc(Cl)c3c(=O)c2C(C)=O)cc1] | methyl 4-(((3-acetyl-5,8-dichloro-4-oxo-1,4-dihydroquinolin-2-yl)sulfinyl)methyl)benzoate |
| 92 | 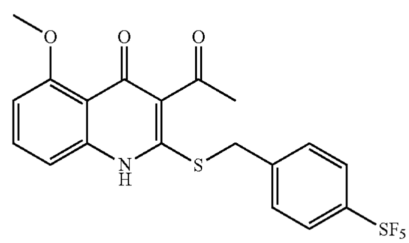 | 3-acetyl-5-methoxy-2-((4-(pentafluoro-λ6-sulfanyl)benzyl)thio)quinolin-4(1H)-one |
| 93 | 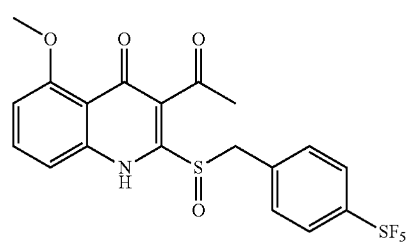 | 3-acetyl-5-methoxy-2-((4-(pentafluoro-λ6-sulfanyl)benzyl)sulfinyl)quinolin-4(1H)-one |
| 94 | 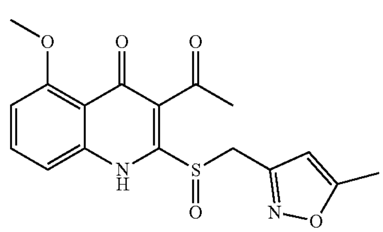 [SMILES: COc1cccc2[nH]c(S(=O)Cc3cc(C)on3)c(C(C)=O)c(=O)c12] | 3-acetyl-5-methoxy-2-(((5-methylisoxazol-3-yl)methyl)sulfinyl)quinolin-4(1H)-one |

TABLE 3-continued

| Compound Number | Structure | IUPAC Name |
| --- | --- | --- |
| 95 | 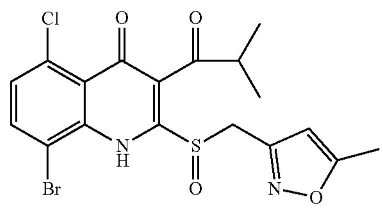 | 8-bromo-5-chloro-3-isobutyryl-2-(((5-methylisoxazol-3-yl)methyl)sulfinyl)quinolin-4(1H)-one |
| 96 | 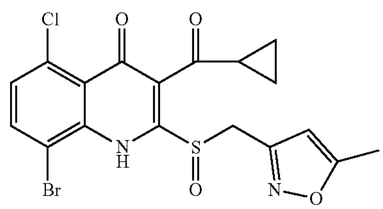 [SMILES: Cc1cc(CS(=O)c2[nH]c3c(Br)ccc(Cl)c3c(=O)c2C(=O)C2CC2)no1] | 8-bromo-5-chloro-3-(cyclopropanecarbonyl)-2-(((5-methylisoxazol-3-yl)methyl)sulfinyl)quinolin-4(1H)-one |
| 97 | 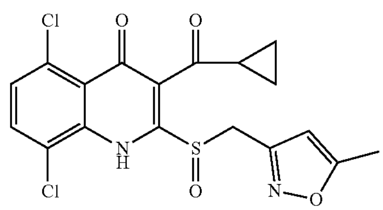 [SMILES: Cc1cc(CS(=O)c2[nH]c3c(Cl)ccc(Cl)c3c(=O)c2C(=O)C2CC2)no1] | 5,8-dichloro-3-(cyclopropanecarbonyl)-2-(((5-methylisoxazol-3-yl)methyl)sulfinyl)quinolin-4(1H)-one |
| 98 | 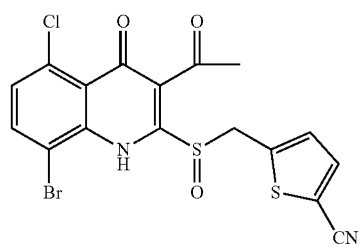 [SMILES: CC(=O)c1c(S(=O)Cc2ccc(C#N)s2)[nH]c2c(Br)ccc(Cl)c2c1=O] | 5-(((3-acetyl-8-bromo-5-chloro-4-oxo-1,4-dihydroquinolin-2-yl)sulfinyl)methyl)thiophene-2-carbonitrile |
| 99 | 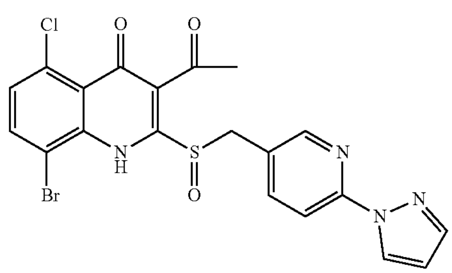 [SMILES: CC(=O)c1c(S(=O)Cc2ccc(-n3cccn3)nc2)[nH]c2c(Br)ccc(Cl)c2c1=O] | 2-(((6-(1H-pyrazol-1-yl)pyridin-3-yl)methyl)sulfinyl)-3-acetyl-8-bromo-5-chloroquinolin-4(1H)-one |
| 100 | 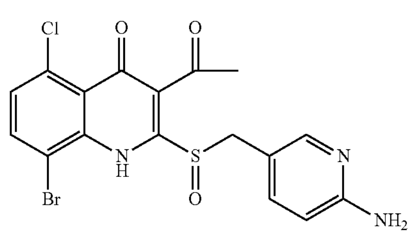 [SMILES: CC(=O)c1c(S(=O)Cc2ccc(N)nc2)[nH]c2c(Br)ccc(Cl)c2c1=O] | 3-acetyl-2-(((6-aminopyridin-3-yl)methyl)sulfinyl)-8-bromo-5-chloroquinolin-4(1H)-one |

TABLE 3-continued

| Compound Number | Structure | IUPAC Name |
| --- | --- | --- |
| 101 | 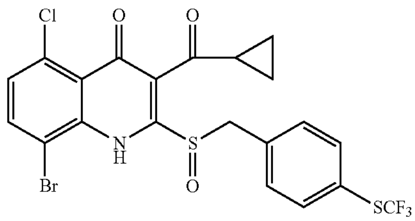 | 8-bromo-5-chloro-3-(cyclopropanecarbonyl)-2-((4-((trifluoromethyl)thio)benzyl)sulfinyl)quinolin-4(1H)-one |
| 102 | 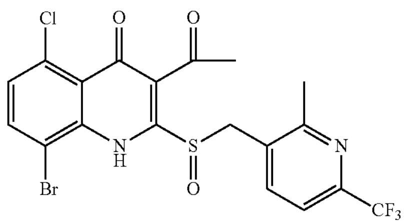 [SMILES: CC(=O)c1c(S(=O)Cc2ccc(C(F)(F)F)nc2C)[nH]c2c(Br)ccc(Cl)c2c1=O] | 3-acetyl-8-bromo-5-chloro-2-(((2-methyl-6-(trifluoromethyl)pyridin-3-yl)methyl)sulfinyl)quinolin-4(1H)-one |
| 103 | 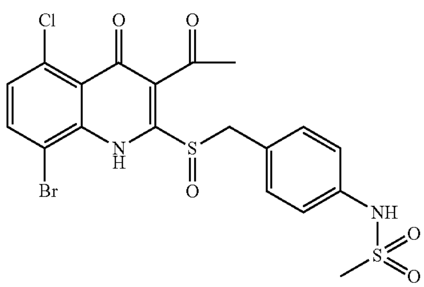 [SMILES: CC(=O)c1c(S(=O)Cc2ccc(NS(C)(=O)=O)cc2)[nH]c2c(Br)ccc(Cl)c2c1=O] | N-(4-(((3-acetyl-8-bromo-5-chloro-4-oxo-1,4-dihydroquinolin-2-yl)sulfinyl)methyl)phenyl)methanesulfonamide |
| 104 | 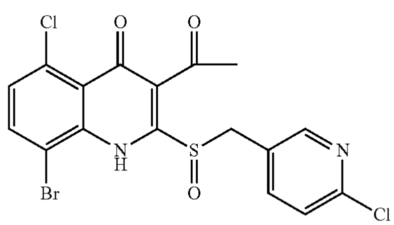 [SMILES: CC(=O)c1c(S(=O)Cc2ccc(Cl)nc2)[nH]c2c(Br)ccc(Cl)c2c1=O] | 3-acetyl-8-bromo-5-chloro-2-(((6-chloropyridin-3-yl)methyl)sulfinyl)quinolin-4(1H)-one |
| 105 | 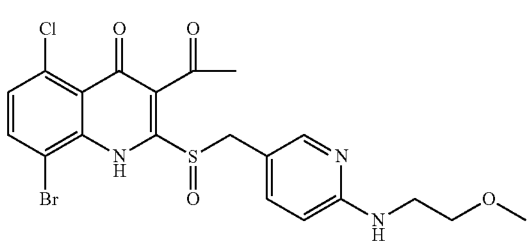 [SMILES: COCCNc1ccc(CS(=O)c2[nH]c3c(Br)ccc(Cl)c3c(=O)c2C(C)=O)cn1] | 3-acetyl-8-bromo-5-chloro-2-(((6-((2-methoxyethyl)amino)pyridin-3-yl)methyl)sulfinyl)quinolin-4(1H)-one |

TABLE 3-continued

| Compound Number | Structure | IUPAC Name |
|---|---|---|
| 106 | 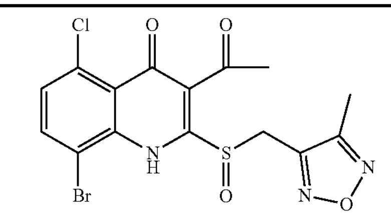 | 3-acetyl-8-bromo-5-chloro-2-(((4-methyl-1,2,5-oxadiazol-3-yl)methyl)sulfinyl)quinolin-4(1H)-one |
| 107 | 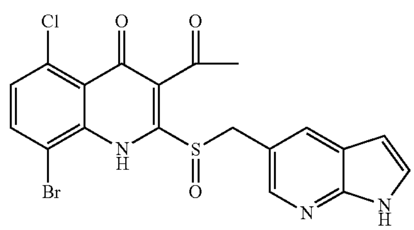 [SMILES: CC(=O)c1c(S(=O)Cc2cnc3[nH]ccc3c2)[nH]c2c(Br)ccc(Cl)c2c1=O] | 2-(((1H-pyrrolo[2,3-b]pyridin-5-yl)methyl)sulfinyl)-3-acetyl-8-bromo-5-chloroquinolin-4(1H)-one |

In another embodiment, the present disclosure provides therapeutically effective amounts of the compounds of Formula 1, 2 or 3 or pharmaceutically acceptable salts thereof, and a (pharmaceutical) composition including a pharmaceutically acceptable carrier.

In another embodiment, the present disclosure provides therapeutically effective amounts of the compounds of Formula 1, 2 or 3 or pharmaceutically acceptable salts thereof and a pharmaceutically acceptable carrier, and provides a (pharmaceutical) composition including a therapeutically effective amount of an active pharmaceutical ingredient selected from the group consisting of other anti-cancer agents other than the compounds of the present disclosure, cytostatic drugs, angiogenesis inhibitors, kinase inhibitors, cytokine blockers and cell adhesion molecule inhibitors.

When the novel compounds according to the present disclosure are used as anti-cancer agents, the dose is as follows. Any suitable route for administration of the compounds of the present disclosure may be selected, the type of pharmaceutical composition suitable for such route may be determined, and for the intended treatment, the compound may be administered in an effective dose. The effective dose is generally from about 0.001 to about 100 mg/kg body weight/day, preferably from about 0.01 to about 30 mg/kg/day, in a single or divided dose. Depending on the age, species, and diseases or conditions to be treated, a dose below the lower limit of this range may be appropriate. In other cases, higher doses may be used without harmful side effects. Higher doses may be divided into smaller doses and administered daily. Methods of determining an appropriate dose are well known in the art to which the present disclosure pertains. For example, a document, such as Remington: The Science and Practice of Pharmacy, Mack Publishing Co., 20th ed., 2000, may be used.

References for Preparing (Pharmaceutical) Composition

Methods for the preparation of pharmaceutical compositions for the treatment or prevention of diseases or conditions are well known to those of ordinary skill in the art. For example, as described in references such as Handbook of Pharmaceutical Excipients (7$^{th}$ ed.), Remington: The Science and Practice of Pharmacy (20$^{th}$ ed.), Encyclopedia of Pharmaceutical Technology (3$^{rd}$ ed.) Sustained and Controlled Release Drug Delivery Systems (1978), a pharmaceutically acceptable carrier, additives and the like may be suitably mixed with the compounds according to the present disclosure to prepare a pharmaceutical composition for the object of the present disclosure.

DETAILED DESCRIPTION OF EXEMPLARY EMBODIMENTS

Hereinafter, the present disclosure is described in detail with reference to the following examples. However, the examples according to the present disclosure can be modified into various other forms, and the scope of the present disclosure should not be construed as being limited to the following examples. The examples are provided to more fully explain the present disclosure to those skilled in the art to which the present disclosure pertains.

Preparation of Compounds of the Present Disclosure

The reagents and solvents used in the experiments described below can be purchased from Aldrich Chemical Co. (Milwaukee, Wis., USA). A $^1$H-NMR spectrum was measured using a Varian Gemini 400 MHz NMR spectrometer.

Preparation of Compounds 3-acetyl-8-bromo-5-chloro-2-(methylthio)quinolin-4(1H)-one (4a), 3-acetyl-2-(benzylthio)-8-bromo-5-chloroquinolin-4(1H)-one (4b), 3-acetyl-8-bromo-5-chloro-2-(methylsulfinyl)quinolin-4(1H)-one (5a), and 3-acetyl-2-(benzylsulfinyl)-8-bromo-5-chloroquinolin-4(1H)-one (5b)

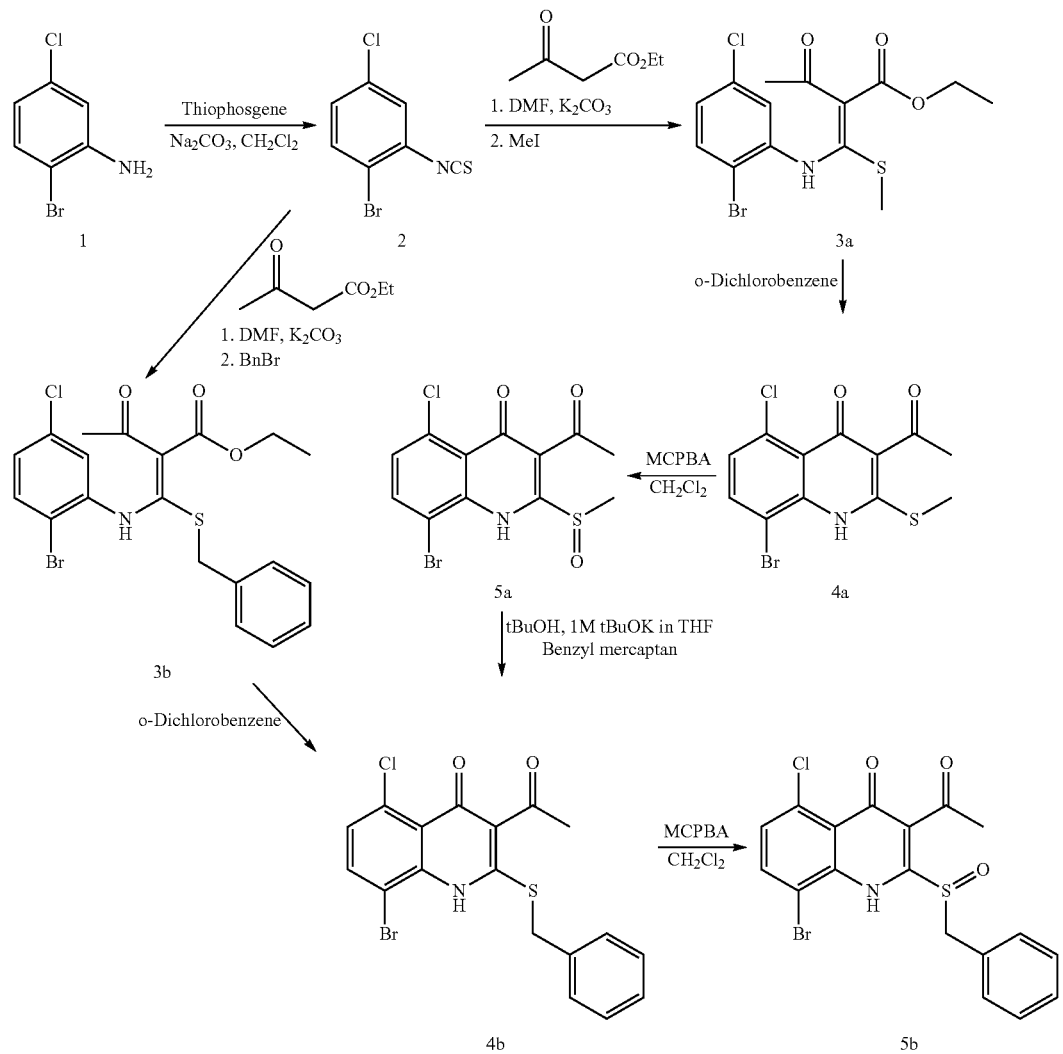

Synthesis of 2-bromo-5-chlorophenyl isothiocyanate (2) (isothiocyanate Formation)

2-Bromo-5-chloroaniline (1) (10 g, 48.5 mmol) was dissolved in anhydrous dichloroethane (CH$_2$Cl$_2$, 250 mL) and sodium carbonate (Na$_2$CO$_3$, 11 g, 97 mmol) was added thereto. The solution was cooled to 5° C. with ice water under nitrogen gas, and thiophosgene (5.5 mL, 72.7 mmol) was added very slowly to the solution in that state. The reaction solution was stirred at room temperature for 12 hours and then filtered to remove inorganic matter. After removing the solvent by distillation under reduced pressure, nucleic acid (n-Hexane, 50 mL) was added to the resulting solid, and then the mixture was stirred for 10 minutes and subjected to filtering to quantitatively obtain a title compound as a yellow solid.

$^1$H NMR (300 MHz, CDCl$_3$) δ 7.51-7.49 (d, J=8.61 Hz, 1H), 7.26-7.25 (d, J=2.4 Hz, 1H), 7.13-7.09 (dd, J=2.46, 6.18 Hz, 1H).

LC/MS data: 249.52 g/mol

Synthesis of Ethyl (Z)-2-(((2-bromo-5-chlorophenyl)amino)(methylthio)methylene)-3-oxobutanoate, Compound 3a (C=C Bond Formation)

Isothiothianate (2) (10 g, 40 mmol) synthesized in step 1 was dissolved in anhydrous DMF (20 mL), and the mixed solution was slowly added to a solution of ethyl oxobutanoate (5.2 g, 40 mmol) and K$_2$CO$_3$ (5.6 g, 40 mmol) dissolved in DMF (100 mL) at room temperature. The mixture was stirred for 12 hours at room temperature, and then iodomethane (5.7 g, 40 mmol) was slowly added thereto at room temperature. The solution was then stirred at room temperature for one day. After completion of the reaction was confirmed by TLC, water and ethyl acetate were added and the desired compound was extracted as an organic layer. Water was removed from the extracted organic layer using MgSO$_4$, and the extracted organic layer was subjected to distillation under reduced pressure, and then purification was performed using a column to obtain title Compound 3a.

$^1$H NMR (300 MHz, CDCl$_3$) δ 12.90 (s, 1H), 7.45-7.42 (d, J=8.41 Hz, 1H), 6.90-6.86 (d, J=7.74 Hz, 1H), 6.68 (s, 1H), 4.36-4.29 (m, 2H), 2.54 (s, 3H), 2.04 (s, 3H), 1.37-1.33 (t, J=7.26 Hz, 3H).

LC/MS data: 393.69 g/mol

Synthesis of 3-acetyl-8-bromo-5-chloro-2-(methylthio)quinolin-4(1H)-one, Compound 4a (Cyclization)

Compound 3a synthesized in step 2 was dissolved in o-dichlorobenzene and stirred for 12 hours while heated at 180° C. After the reaction was completed, the reaction mixture was cooled to room temperature and was subjected to distillation under reduced pressure. A nucleic acid was added to the resulting solid, and the mixture was stirred for 10 minutes and was subjected to filtering to obtain Compound 4a.

$^1$H NMR (300 MHz, CDCl$_3$) δ 8.67 (s, 1H), 7.91-7.88 (d, J=8.19 Hz, 1H), 7.71-7.68 (d, J=8.49 Hz, 1H), 2.97 (s, 3H), 2.79 (s, 3H).

LC/MS data: 347.62 g/mol

Synthesis of 3-acetyl-8-bromo-5-chloro-2-(methylsulfinyl)quinolin-4(1H)-one, Compound 5a (Oxidation)

The quinolone compound 4a obtained in step 3 was oxidized with MCPBA (1.5 eq.) in anhydrous dichloroethane (CH$_2$Cl$_2$, 10 mL) to obtain title Compound 5a.

$^1$H NMR (300 MHz, CDCl$_3$) δ 11.13 (s, 1H), 7.82-7.79 (d, J=8.43 Hz, 1H), 7.38-7.36 (d, J=8.46 Hz, 1H), 3.02 (s, 3H), 2.78 (s, 3H).

LC/MS data: 363.62 g/mol

Synthesis of Ethyl (Z)-2-((benzylthio)((2-bromo-5-chlorophenyl)amino)methylene)-3-oxobutanoate, Compound 3b Title Compound 3b was synthesized using benzyl bromide instead of MeI in a similar manner to the synthesis of Compound 3a.

$^1$H NMR (300 MHz, CDCl$_3$) δ 12.90 (s, 1H), 7.46-7.44 (m, 2H), 7.35-7.24 (m, 4H), 6.91-6.89 (d, J=7.95 Hz, 1H), 6.70 (s, 1H), 4.49-4.19 (m, 4H), 2.05 (s, 3H), 1.36-1.31 (t, J=7.11 Hz, 3H).

LC/MS data: 469.79 g/mol

Synthesis of 3-acetyl-2-(benzylthio)-8-bromo-5-chloroquinolin-4(1H)-one, Compound 4b Title Compound 4b was synthesized in a similar manner to the synthesis of Compound 4a.

$^1$H NMR (300 MHz, CDCl$_3$) δ 8.59 (s, 1H), 7.93-7.90 (d, J=8.25 Hz, 1H), 7.52-7.47 (m, 2H), 7.42-7.21 (m, 4H), 4.80 (s, 2H), 2.93 (s, 3H).

LC/MS data: 423.72 g/mol

Synthesis of 3-acetyl-2-(benzylsulfinyl)-8-bromo-5-chloroquinolin-4(1H)-one, Compound 5b Title Compound 5b was synthesized in a similar manner to the synthesis of Compound 5a.

Using the above-mentioned methods, the following compounds according to the present disclosure were synthesized by modifying reactants and/or starting materials appropriately. LC/MS and $^1$H NMR measurement results are summarized in Table 4. In Table 4 below, MW refers to an average molecular weight, and MS is the value obtained by analyzing the actually prepared compounds.

TABLE 4

| Compound Number | Formula Name | MW (Molecular Weight) | LC/MS data | $^1$H NMR |
| --- | --- | --- | --- | --- |
| 1 | 3-acetyl-8-bromo-5-chloro-2-(methylsulfinyl)quinolin-4(1H)-one | 362.62 | 363 | $^1$H NMR (300 MHz, CDCl$_3$)δ11.13 (br, 1H), 7.81 (d, J = 8.4 Hz, 1H), 7.37 (d, J = 8.4 Hz, 1H), 3.02 (s, 3H), 2.78 (s, 3H). |
| 2 | 3-acetyl-8-bromo-5-chloro-2-(methylthio)quinolin-4(1H)-one | 346.63 | 348 | $^1$H NMR (300 MHz, CDCl$_3$)δ8.67(s, 1H), 7.91-7.88(d, J = 8.19 Hz, 1H), 7.71-7.68(d, J = 8.49 Hz, 1H), 2.97(s, 3H), 2.79(s, 3H). |
| 3 | 3-acetyl-2-(benzylthio)-8-bromo-5-chloroquinolin-4(1H)-one | 422.72 | 423 | $^1$H NMR (300 MHz, CDCl$_3$)δ16.43 (s, 0.5H), 8.59 (br, 0.5H), 7.91 (d, J = 8.3 Hz, 1H), 7.62 (d, J = 8.4 Hz, 0.5H), 7.48-7.52 (m, 3H), 7.27-7.43 (m, 5H), 7.22 (d, J = 8.4 Hz, 0.5H), 4.80 (s, 2H), 4.32 (s, 1H), 2.93 (s, 3H), 2.69 (s, 1.5H). |
| 4 | 3-acetyl-2-(benzylsulfinyl)-8-bromo-5-chloroquinolin-4(1H)-one | 438.72 | 439 | $^1$H NMR (300 MHz, CDCl$_3$)δ10.24 (br, 1H), 7.67 (d, J = 8.4 Hz, 1H), 7.29 (d, J = 8.4 Hz, 1H), 7.13-7.22 (m, 3H), 7.08-7.11 (m, 2H), 4.59-4.25 (m, 2H), 2.84 (s, 3H). |
| 5 | 3-acetyl-8-bromo-5-chloro-1-methyl-2-(methylthio)quinolin-4(1H)-one | 360.65 | 360 | $^1$H NMR (300 MHz, CDCl$_3$)δ7.92-7.89(d, J = 8.22 Hz, 1H), 7.36-7.33(d, J = 8.13 Hz, 1H), 3.89(s, 3H), 2.74(s, 3H), 2.65(s, 3H). |

TABLE 4-continued

| Compound Number | Formula Name | MW (Molecular Weight) | LC/MS data | $^1$H NMR |
|---|---|---|---|---|
| 6 | 3-acetyl-5, 8-dichloro-2-(methylsulfinyl)quinolin-4(1H)-one | 318.17 | 318 | $^1$H NMR (300 MHz, CDCl$_3$)δ11.07(s, 1H), 7.67-7.64(d, J = 8.46 Hz, 1H), 7.44-7.41(d, J = 8.46 Hz, 1H), 3.02(s, 3H), 2.78(s, 3H). |
| 7 | 3-acetyl-6-fluoro-2-methyl-2-(methylthio)quinolin-4(1H)-one | 265.30 | 266 | $^1$H NMR (300 MHz, CDCl$_3$)δ7.92-7.87(q, J = 5.1, 3.99 Hz, 1H), 7.69-7.65(q, J = 2.88, 6.45 Hz, 1H), 7.48-7.39(m, 1H), 4.53-4.46(q, J = 7.14, 7.14 Hz, 2H), 4.08(s, 3H), 3.66(s, 3H), 1.48-1.44(t, J = 7.14 Hz, 3H). |
| 8 | 1-(6-fluoro-4-hydroxy-2-(methylthio)quinolin-3-yl)ethan-1-one | 251.28 | 252 | $^1$H NMR (300 MHz, CDCl$_3$)δ7.83-7.78(m, 2H), 7.49-7.42(m, 1H), 4.59-4.52(q, J = 7.14 Hz, 2H), 2.58(s, 3H), 1.56-1.51(t, J = 7.14 Hz, 3H). |
| 9 | 3-acetyl-8-bromo-1-(4-bromobenzoyl)-5-chloro-2-(methylsulfinyl)quinolin-4(1H)-one | 545.63 | 544 | $^1$H NMR (300 MHz, CDCl$_3$)δ8.09-8.07(d, J = 5.73 Hz, 1H), 8.06-8.04(d, J = 6.15 Hz, 2H), 7.73-7.70(d, J = 8.58 Hz, 2H), 7.56-7.54(d, J = 8.22 Hz, 1H), 3.15(s, 3H), 2.63(s, 3H). |
| 10 | 3-acetyl-8-bromo-5-chloro-2-((4-chlorobenzyl)thio)quinolin-4(1H)-one | 457.16 | 456 | $^1$H NMR (300 MHz, DMSO) δ 7.65-7.62(d, J = 8.13 Hz, 1H), 7.45-7.42(d, J = 6.69 Hz, 2H), 7.29-7.26(d, J = 8.34 Hz, 2H), 6.91-6.88(d, J = 8.19 Hz, 1H), 4.44(s, 2H), 2.40(s, 3H). |
| 11 | 3-acetyl-8-bromo-5-chloro-2-((4-chlorobenzyl)sulfinyl)quinolin-4(1H)-one | 473.16 | 472 | $^1$H NMR (300 MHz, CDCl$_3$)δ10.21(s, 1H), 7.73-7.71(d, J = 8.43 Hz, 1H), 7.33-7.31(d, J = 8.37 Hz, 1H), 7.18-7.15(d, J = 9 Hz, 2H), 7.05-7.03(d, J = 8.25 Hz, 2H), 4.37(s, 2H), 2.84(s, 3H). |
| 12 | 3-acetyl-8-bromo-5-chloro-2-(phenylthio)quinolin-4(1H)-one | 408.69 | 408 | $^1$H NMR (300 MHz, MeOD) δ 7.51-7.48(m, 2H), 7.46-7.43(d, J = 8.11 Hz, 1H), 7.31-7.28(d, J = 7.71 Hz, 3H), 6.81-6.78(d, J = 8.19 Hz, 1H). |
| 13 | 3-acetyl-8-bromo-5-chloro-2-(phenylsulfinyl)quinolin-4(1H)-one | 424.69 | 424 | $^1$H NMR (300 MHz, CDCl$_3$)δ7.84-7.75(m, 2H), 7.68-7.64(m, 2H), 7.52-7.50(d, J = 8.43 Hz, 1H), 7.48-7.45(m, 1H), 7.38-7.35(d, J = 8.43 Hz, 1H), 2.78(s, 3H). |
| 14 | 3-acetyl-8-bromo-5-chloro-2-((2-methoxyphenyl)thio)quinolin-4(1H)-one | 438.72 | 438 | $^1$H NMR (300 MHz, CDCl$_3$)δ8.55(s, 1H), 7.709(m, 1H), 7.633(m, 1H), 7.511(d, 1H, J = 8.43 Hz), 7.158(m, 3H), 3.861(s, 3H), 2.781(s, 3H). |
| 15 | 3-acetyl-8-bromo-5-chloro-2-((2-methoxyphenyl)sulfinyl)quinolin-4(1H)-one | 454.72 | 454 | $^1$H NMR (300 MHz, CDCl$_3$)δ7.84(d, J = 8.4 Hz, 1H), 7.383 (d, J = 8.4 Hz, 1H), 7.53 (m, 1H), 7.415 (m, 1H), 6.949 (s, 1H), 6.956 (s, 1H), 3.86 (s, 3H), 2.634 (s, 3H) |
| 16 | 3-acetyl-8-bromo-2-((4-bromophenyl)thio)-5-chloroquinolin-4(1H)-one | 487.59 | 486 | $^1$H NMR (300 MHz, CDCl$_3$)δ8.30(s, 1H), 7.779(d, J = 8.4 Hz, 2H), 7.614(d, J = 8.46 Hz, 2H), 7.541(d, J = 8.4 Hz, 1H), 7.183(d, J = 8.46 Hz, 1H), 2.77(s, 3H). |
| 17 | 3-acetyl-8-bromo-2-((4-bromophenyl)sulfinyl)-5-chloroquinolin-4(1H)-one | 503.59 | 502 | $^1$H NMR (300 MHz, CDCl$_3$)δ11.37(s, 1H), 7.84-7.81(d, J = 8.46 Hz, 1H), 7.73-7.70(d, J = 8.73 Hz, 2H), 7.60-7.57(d, J = 8.67 Hz, 2H), 7.39-7.38(d, J = 8.43 Hz, 1H), 2.70(s, 3H). |
| 18 | 1,1'-(8-bromo-5-chloro-2-(methylthio)-4-oxoquinoline-1,3(4H)-diyl)bis(ethan-1-one) | 388.66 | 388 | $^1$H NMR (300 MHz, MeOD) δ 7.84 (d, J = 8.25 Hz, 1H), 7.19(d, J = 8.25 Hz, 1H), 2.72(s, dH), 2.57(s, 3H), 2.18(s, 3H). |
| 19 | 1,1'-(8-bromo-5-chloro-2-(methylsulfinyl)-4-oxoquinoline-1,3(4H)-diyl)bis(ethan-1-one) | 404.66 | 404 | $^1$H NMR (300 MHz, CDCl$_3$)δ8.07(m, 1H), 7.60(m, 1H), 3.03(s, 3H), 3.02(s, 3H), 2.78(s, 3H). |
| 20 | 3-acetyl-2-(benzylsulfinyl)-8-bromo-1-(4-bromobenzoyl)-5-chloroquinolin-4(1H)-one | 621.72 | 620 | $^1$H NMR (300 MHz, (CD$_3$)$_2$CO)δ7.96-7.93(d, J = 8.22 Hz, 1H), 7.73-7.60(m, 7H), 7.45-7.42(d, J = 8.25 Hz, 2H), 7.16-7.13(d, J = 8.19 Hz, 1H), 2.86(s, 3H). |

TABLE 4-continued

| Compound Number | Formula Name | MW (Molecular Weight) | LC/MS data | ¹H NMR |
|---|---|---|---|---|
| 21 | 3-acetyl-8-bromo-1-(4-bromobenzoyl)-5-chloro-2-(methylsulfonyl)quinolin-4(1H)-one | 561.63 | 560 | ¹H NMR (300 MHz, CDCl$_3$)δ8.10(d, J = 8.22 Hz, 1H), 8.03-7.67 (dd, J = 8.61, 88.8 Hz, 4H), 7.60(J = 8.22 Hz, 1H), 3.53(s, 3H), 2.67(s, 3H). |
| 22 | 3-acetyl-8-bromo-5-chloro-1-(3-chloro-4-fluorobenzyl)-2-(methylsulfinyl)quinolin-4(1H)-one | 505.18 | 504 | ¹H NMR (300 MHz, CDCl$_3$)δ7.42-7.37(m, 2H), 7.24-7.09(m, 3H), 4.49(s, 2H), 3.44(s, 3H), 2.14(s, 3H). |
| 23 | 3-acetyl-2-(benzylthio)-8-bromo-1-(4-bromobenzoyl)-5-chloroquinolin-4(1H)-one | 605.73 | 604 | ¹H NMR (300 MHz, CDCl$_3$)δ8.06-8.03(d, J = 8.28 Hz, 1H), 7.93-7.91(d, J = 8.64 Hz, 2H), 7.71-7.68(d, 8.64 Hz, 2H), 7.54-7.51(d, J = 7.02 Hz, 2H), 7.49-7.46(d, J = 8.25 Hz, 1H), 7.30-7.27(d, J = 7.33 Hz, 2H), 6.97(s, 1H), 4.71(s, 2H). |
| 24 | 3-acetyl-8-bromo-5-chloro-2-(isopropylthio)quinolin-4(1H)-one | 374.68 | 374 | ¹H NMR(300 MHz, CDCl$_3$)δ16.32(s, 1H), 7.77-7.86(d, J = 8.13 Hz, 1H), 7.26-7.23(d, J = 8.61 HZ, 1H), 4.54-4.45(m, 1H), 2.94(s, 3H), 1.54-1.51(m, 6H). |
| 25 | 3-acetyl-8-bromo-5-chloro-2-(isopropylsulfinyl)quinolin-4(1H)-one | 390.68 | 390 | ¹H NMR(300 MHz, CDCl$_3$)δ10.99(s, 1H), 7.80-7.77(d, J = 8.37 Hz, 1H), 7.36-7.34(d, J = 8.4 Hz, 1H), 3.61-3.51(m, 1H), 2.77(s, 3H), 1.63-1.61(d, J = 7.12 Hz, 3H), 1.01-0.99(d, J = 6.78 Hz, 3H). |
| 26 | 3-acetyl-8-bromo-5-chloro-2-((1-phenylethyl)sulfinyl)quinolin-4(1H)-one | 452.75 | 452 | ¹H NMR(300 MHz, CDCl$_3$)δ11.06(br, 1H), 7.82(d, J = 8.4 Hz, 1H), 7.60-7.65 (m, 2H), 7.41-7.50 (m, 3H), 7.38 (d, J = 8.5 Hz, 1H), 4.72 (q, J = 7.3 Hz, 1H), 2.84 (s, 3H), 1.42 (d, J = 7.1 Hz, 3H). |
| 27 | 3-(((3-acetyl-8-bromo-5-chloro-4-oxo-1,4-dihydroquinolin-2-yl)thio)methyl)benzonitrile | 447.73 | 447 | ¹H NMR (300 MHz, CDCl$_3$)δ7.92(d, J = 8.3 Hz, 1H), 7.83 (s, 1H), 7.76 (d, J = 7.9 Hz, 1H), 7.55 (d, J = 7.7 Hz, 1H), 7.42 (t, J = 7.8 Hz, 1H), 7.32 (d, J = 8.3 Hz, 1H), 4.82 (s, 2H), 2.94 (s, 3H). |
| 28 | 3-(((3-acetyl-8-bromo-5-chloro-4-oxo-1,4-dihydroquinolin-2-yl)sulfinyl)methyl)benzonitrile | 463.73 | 463 | ¹H NMR (300 MHz, CDCl$_3$)δ10.27(br, 1H), 7.72(d, J = 8.5 Hz, 1H), 7.53-7.57 (m, 1H), 7.27-7.40 (m, 2H), 4.59-4.22 (m, 2H), 2.85 (s, 3H). |
| 29 | 3-acetyl-8-bromo-5-chloro-2-((2,4-difluorobenzyl)sulfinyl)quinolin-4(1H)-one | 474.70 | 474 | ¹H NMR (300 MHz, CDCl$_3$)δ10.34(br, 1H), 7.74(d, J = 8.4 Hz, 1H), 7.35 (d, J = 8.4 Hz, 1H), 7.20-7.28 (m, 1H), 6.81-6.87 (m, 1H), 6.60-6.75 (m, 1H), 4.53 (dd, J = 48.9, 13.2 Hz, 2H), 2.85 (s, 3H). |
| 30 | 3-acetyl-8-bromo-5-chloro-2-((3-chloro-4-fluorobenzyl)thio)quinolin-4(1H)-one | 475.15 | 474 | ¹H NMR (300 MHz, CDCl$_3$)δ7.92(d, J = 8.3 Hz, 1H), 7.83 (s, 1H), 7.76 (d, J = 7.9 Hz, 1H), 7.55 (d, J = 7.7 Hz, 1H), 7.42 (t, J = 7.8 Hz, 1H), 7.32 (d, J = 8.3 Hz, 1H), 4.82 (s, 2H), 2.94 (s, 3H). |
| 31 | 3-acetyl-8-bromo-5-chloro-2-((3-chloro-4-fluorobenzyl)sulfinyl)quinolin-4(1H)-one | 491.15 | 490 | ¹H NMR (300 MHz, CDCl$_3$)δ10.27(br, 1H), 7.73(d, J = 8.4 Hz, 1H), 7.33 (d, J = 8.4 Hz, 1H), 7.22-7.24 (m, 1H), 6.95-6.98 (m, 2H), 4.33 (q, J = 12.8 Hz, 2H), 2.84 (s, 3H). |
| 32 | 3-acetyl-8-bromo-5-chloro-2-((4-nitrobenzyl)thio)quinolin-4(1H)-one | 467.72 | 467 | ¹H NMR (300 MHz, CDCl$_3$)δ8.16(d, J = 8.6 Hz, 2H), 7.92 (d, J = 8.3 Hz, 1H), 7.69 (d, J = 8.6 Hz, 2H), 7.32 (d, J = 8.2 Hz, 1H), 4.90 (s, 2H), 2.94 (s, 3H). |
| 33 | 3-acetyl-8-bromo-5-chloro-2-((4-nitrobenzyl)sulfinyl)quinolin-4(1H)-one | 483.72 | 483 | ¹H NMR (300 MHz, CDCl$_3$)δ10.23(br, 1H), 8.08(d, J = 8.7 Hz, 2H), 7.70 (d, J = 8.4 Hz, 1H), 7.34 (dd, J = 8.5, 3.9 Hz, 3H), 4.49 (dd, J = 27.8, 12.6 Hz, 2H), 2.85 (s, 3H). |
| 34 | 3-acetyl-2-(benzylsulfonyl)-8-bromo-5-chloroquinolin-4(1H)-one | 454.72 | 454 | ¹H NMR(300 MHz, CDCl$_3$)δ10.25(s, 1H), 7.66(d, J = 8.46 Hz, 1H), 7.28(d, J = 8.43 Hz, 1H), 7.20-7.08(m, 5H), 4.41(d, J = 3, 2H), 2.84(s, 3H). |

TABLE 4-continued

| Compound Number | Formula Name | MW (Molecular Weight) | LC/MS data | ¹H NMR |
|---|---|---|---|---|
| 35 | 3-acetyl-8-bromo-5-chloro-1-(methylsulfonyl)-2-(methylthio)quinolin-4(1H)-one | 424.71 | 424 | ¹H NMR (300 MHz, CDCl₃)δ7.96(d, J = 8.25 Hz, 1H), 7.42(d, J = 8.28 Hz, 1H), 3.30(s, 3H), 2.76(s, 3H), 2.73(s, 3H). |
| 36 | 3-acetyl-8-bromo-5-chloro-2-(methylsulfinyl)-1-((trifluoromethyl)sulfonyl)quinolin-4(1H)-one | 494.68 | 494 | ¹H NMR (300 MHz, CDCl₃)δ8.08-8.05(d, J = 8.22 Hz, 1H), 7.69-7.65(d, J = 8.25 Hz, 1H), 3.11(s, 3H), 2.78(s, 3H). |
| 37 | 3-acetyl-8-bromo-5-chloro-1-((4-chlorophenyl)sulfonyl)-2-(methylthio)quinolin-4(1H)-one | 521.22 | 520 | ¹H NMR (300 MHz, CDCl₃)δ7.93-7.91(d, J = 8.22 Hz, 1H), 7.74-7.71(d, J = 8.7 Hz, 2H), 7.50-7.47(d, J = 8.61 Hz, 2H), 7.32-7.30(d, J = 8.25 Hz, 1H), 2.71(s, 3H), 2.62(s, 3H). |
| 38 | 3-acetyl-8-bromo-5-chloro-2-(methylthio)-1-((4-nitrophenyl)sulfonyl)quinolin-4(1H)-one | 531.78 | 531 | ¹H NMR (300 MHz, CDCl₃)δ8.39-8.36(d, J = 8.85 Hz, 2H), 8.03-8.00(d, J = 8.85 Hz, 2H), 7.96-9.93 (d, J = 8.22 Hz, 1H), 7.35-7.32(d, J = 8.22 Hz, 1H), 2.74(s, 3H), 2.62(s, 3H). |
| 39 | 3-acetyl-8-bromo-5-chloro-1-(ethylsulfonyl)-2-(methylsulfinyl)quinolin-4(1H)-one | 454.73 | 454 | ¹H NMR (300 MHz, CDCl₃)δ7.96-7.93(d, J = 8.23 Hz, 1H), 7.42-7.39(d, J = 8.16 Hz, 1H), 3.54-3.46(q, J = 7.41, 7.5 Hz, 2H), 2.76(s, 3H), 2.73(s, 3H), 1.58-1.53(t, J = 7.38, 7.44 3H). |
| 40 | 3-acetyl-8-bromo-1-((4-(tert-butyl)phenyl)sulfonyl)-5-chloro-2-(methylthio)quinolin-4(1H)-one | 542.89 | 542 | ¹H NMR (300 MHz, CDCl₃)δ7.88-7.85(d, J = 8.16 Hz, 1H), 7.69-7.66(d, J = 8.67 Hz, 2H), 7.47-7.44(d, J = 8.7 Hz, 2H), 7.25-7.23(d, J = 8.13 Hz, 1H), 2.71(s, 3H), 2.63(s, 3H), 1.33 (s, 9H). |
| 41 | 3-acetyl-8-bromo-1-((4-(tert-butyl)phenyl)sulfonyl)-5-chloro-2-(methylsulfonyl)quinolin-4(1H)-one | 574.89 | 574 | ¹H NMR (300 MHz, CDCl₃)δ8.10-8.07(d, J = 8.22 Hz, 1H), 7.80-7.78(d, J = 8.64 Hz, 2H), 7.62-7.59(d, J = 8.25 Hz, 1H), 7.58-7.55(d, J = 8.64 Hz, 2H), 3.48(s, 3H), 2.71(s, 3H), 1.37(s, 9H). |
| 42 | 3-acetyl-8-bromo-1-((4-(tert-butyl)phenyl)sulfonyl)-5-chloro-2-(methylsulfinyl)quinolin-4(1H)-one | 558.89 | 558 | ¹H NMR (300 MHz, CDCl₃)δ8.05-8.03(d, J = 8.16 Hz, 1H), 7.71-7.68(d, J = 8.64 Hz, 2H), 7.52-7.49(d, J = 8.28 Hz, 3H), 3.13(s, 3H), 2.69(s, 3H), 1.35(s, 9H). |
| 43 | 3-acetyl-8-bromo-5-chloro-2-((2,5-dichlorobenzyl)thio)quinolin-4(1H)-one | 491.61 | 490 | ¹H NMR (300 MHz, DMSO) δ 7.93-7.90(d, J = 8.25 Hz, 1H), 7.84 (s, 1H), 7.52-7.49(d, J = 8.52 Hz, 1H), 7.37-7.33(m, 1H), 7.25-7.22(d, J = 8.34 Hz, 1H), 4.65(s, 2H). |
| 44 | 3-acetyl-8-bromo-5-chloro-2-((2,5-dichlorobenzyl)sulfinyl)quinolin-4(1H)-one | 507.60 | 506 | ¹H NMR (300 MHz, CDCl₃)δ10.35(s, 1H), 7.73-7.72(d, J = 10.86 Hz, 1H), 7.32(s, 2H), 7.17(s, 2H), 4.81-4.49(dd, J = 13.33, 69.53 Hz, 2H), 2.81(s, 3H). |
| 45 | 3-acetyl-8-bromo-5-chloro-2-((3,5-difluorobenzyl)thio)quinolin-4(1H)-one | 458.70 | 458 | ¹H NMR (300 MHz, CDCl₃)δ7.93-7.91(d, J = 8.28 Hz, 1H), 7.33-7.30(d, J = 8.28 Hz, 1H), 7.06-7.04(m, 3H), 4.78(s, 2H), 2.94(s, 3H). |
| 46 | 3-acetyl-8-bromo-5-chloro-2-((3,5-difluorobenzyl)sulfinyl)quinolin-4(1H)-one | 474.70 | 474 | ¹H NMR (300 MHz, CDCl₃)δ10.43(s, 1H), 7.75-7.72(d, J = 8.4 Hz, 1H), 7.35-7.32(d. J = 8.46 Hz, 1H), 6.80-6.68(m, 3H), 4.44-4.23(q, J = 12.63, 36.84 Hz, 2H), 2.84(s, 3H). |
| 47 | 3-acetyl-8-bromo-5-chloro-2-((3-iodobenzyl)thio)quinolin-4(1H)-one | 548.62 | 548 | ¹H NMR (300 MHz, DMSO) δ 7.97-7.94(d, J = 5.55 Hz, 1H), 7.89(s, 1H), 7.61-7.58(d, J = 8.16 Hz, 1H), 7.49-7.46(d, J = 7.11 Hz, 1H), 7.31-7.29(m, 1H), 7.13-7.80(t, J = 7.76 Hz, 1H), 4.55(s, 2H). |
| 48 | 3-acetyl-8-bromo-5-chloro-2-((3-iodobenzyl)sulfinyl)quinolin-4(1H)-one | 564.62 | 564 | ¹H NMR (300 MHz, CDCl₃)δ10.19(s, 1H), 7.74-7.71(d, J = 8.46 Hz, 1H), 7.56-7.54(d, J = 8.07 Hz, 1H), 7.39(s, 1H), 7.35-7.32(d, J = 8.46 Hz, 1H), 7.09-7.07(d, J = 8.01 Hz, 1H), 6.97-6.92(t, J = 7.74 Hz, 1H), 4.40-4.30(q, J = 12.71, 6.06 Hz, 2H), 2.87(s, 3H). |

TABLE 4-continued

| Compound Number | Formula Name | MW (Molecular Weight) | LC/MS data | $^1$H NMR |
|---|---|---|---|---|
| 49 | 3-acetyl-8-bromo-5-chloro-2-((3-fluorobenzyl)thio)quinolin-4(1H)-one | 440.71 | 440 | $^1$H NMR (300 MHz, CDCl$_3$)δ7.93-7.91(d, J = 8.25 Hz, 1H), 7.32-7.30(d, J = 8.19 Hz, 2H), 7.28-7.27(m, 2H), 6.97(s, 1H), 4.79(s, 2H), 2.94(s, 3H). |
| 50 | 3-acetyl-8-bromo-5-chloro-2-((3-fluorobenzyl)sulfinyl)quinolin-4(1H)-one | 456.71 | 456 | $^1$H NMR (300 MHz, CDCl$_3$)δ10.30(s, 1H), 7.70-7.67(d, J = 8.56 Hz, 1H), 7.30-7.27(d, J = 8.43 Hz, 1H), 7.15-7.07(m, 1H), 6.98-6.88(m, 2H), 6.83-6.81(d, J = 7.68 Hz, 1H), 4.42-4.32(q, J = 12.66, 3.33 Hz, 2H), 2.82(s, 3H). |
| 51 | 3-acetyl-8-bromo-5-chloro-2-(((5-methylisoxazol-3-yl)methyl)sulfinyl)quinolin-4(1H)-one | 443.70 | 442 | $^1$H NMR (300 MHz, CDCl$_3$)δ10.50(br, 1H), 7.77(d, J = 8.4 Hz, 1H), 7.36 (d, J = 8.4 Hz, 1H), 6.17 (s, 1H), 4.33-4.67 (m, 2H), 2.83 (s, 3H), 2.39 (s, 3H). |
| 52 | 1-(2-(benzylthio)-8-bromo-5-chloro-4-hydroxyquinolin-3-yl)ethan-1-one | 422.72 | 422 | $^1$H NMR (300 MHz, CDCl$_3$)δ7.82(d, J = 8.2 Hz, 1H), 7.53 (d, J = 6.8 Hz, 2H), 7.32-7.48 (m, 3H), 7.26 (d, J = 8.4 Hz, 1H), 6.77 (s, 2H), 5.24 (s, 3H). |
| 53 | 1-(2-(benzylsulfinyl)-8-bromo-5-chloro-4-hydroxyquinolin-3-yl)ethan-1-one | 438.72 | 438 | $^1$H NMR (300 MHz, CDCl$_3$)δ7.99(d, J = 8.2 Hz, 1H), 7.60 (s, 1H), 7.54-7.57 (m, 2H), 7.51 (d, J = 8.2 Hz, 1H), 7.37-7.48 (m, 3H), 5.39 (s, 2H), 3.48(s, 3H). |
| 54 | 1-(2-(benzylsulfonyl)-8-bromo-5-chloro-4-hydroxyquinolin-3-yl)ethan-1-one | 454.72 | 454 | $^1$H NMR (300 MHz, CDCl$_3$)δ7.94(d, J = 8.2 Hz, 1H), 7.73 (s, 1H), 7.54-7.58 (m, 2H), 7.45 (d, J = 8.1 Hz, 2H), 7.38-7.41 (m, 2H), 5.42 (s, 2H), 3.01 (s, 3H). |
| 55 | 3-acetyl-8-bromo-5-chloro-2-((3-methoxybenzyl)sulfinyl)quinolin-4(1H)-one | 468.75 | 468 | $^1$H NMR (300 MHz, CDCl$_3$)δ10.32(s, 1H), 7.71-7.69(d, J = 8.4 Hz, 1H), 7.33-7.30(d, J = 8.43, 1H), 7.09-7.04(t, J = 7.8 Hz, 1H), 6.76-6.70(m, 2H), 6.65-6.63(d, J = 7.47 Hz, 1H), 4.44-4.34(q, J = 12.7, 4.86 Hz, 2H), 3.70(s, 3H), 2.86(s, 3H). |
| 56 | 3-acetyl-8-bromo-5-chloro-2-((4-((trifluoromethyl)thio)benzyl)sulfinyl)quinolin-4(1H)-one | 538.78 | 538 | $^1$H NMR (300 MHz, CDCl$_3$)δ10.27(s, 1H), 7.69-7.66(d, J = 8.40 Hz, 1H), 7.49-7.46(d, J = 8.01 Hz, 2H), 7.31-7.28(d, J = 8.40 Hz, 1H), 7.18-7.15(d, J = 8.16 Hz, 2H), 4.52-4.37(q, J = 12.7, 17.1 Hz, 2H), 2.84(s, 3H). |
| 57 | 3-acetyl-5,8-dichloro-2-((4-nitrobenzyl)sulfinyl)quinolin-4(1H)-one | 439.26 | 439 | $^1$H NMR (300 MHz, MeOD) δ9.95(s, 1H), 8.22-8.20(d, J = 8.6 Hz, 2H), 7.73-7.70(d, J = 8.31 Hz, 2H), 7.63-7.60(d, J = 8.22 Hz, 1H), 7.29-7.26(d, J = 8.13 Hz, 1H), 4.59-4.10(q, J = 12.3, 122 Hz, 2H), 2.72(s, 3H). |
| 58 | 2-(((3-acetyl-8-bromo-5-chloro-4-oxo-1,4-dihydroquinolin-2-yl)sulfinyl)methyl)benzonitrile | 463.73 | 463 | $^1$H NMR (300 MHz, CDCl$_3$)δ10.30(br, 1H), 7.69(d, J = 8.4 Hz, 1H), 7.47-7.61 (m, 2H), 7.34-7.45 (m, 2H), 7.31 (d, J = 8.4 Hz, 1H), 4.71 (q, J = 13.1 Hz, 2H), 2.85 (s, 3H). |
| 59 | 3-acetyl-8-bromo-5-chloro-2-((3,5-dimethoxybenzyl)sulfinyl)quinolin-4(1H)-one | 498.77 | 498 | $^1$H NMR (300 MHz, CDCl$_3$)δ10.36(s, 1H), 7.69(d, J = 8.4 Hz, 1H), 7.30 (d, J = 8.4 Hz, 1H), 6.23 (s, 3H), 4.25-4.39 (m, 2H), 3.62 (s, 6H), 2.83 (s, 3H). |
| 60 | 3-acetyl-8-bromo-2-((4-(tert-butyl)benzyl)sulfinyl)-5-chloroquinolin-4(1H)-one | 494.83 | 494 | $^1$H NMR (300 MHz, CDCl$_3$)δ10.15(br, 1H), 7.62 (d, J = 8.4 Hz, 1H), 7.25 (d, J = 8.4 Hz, 1H), 7.13 (d, J = 8.3 Hz, 2H), 6.96 (d, J = 8.3 Hz, 2H), 4.40 (dd, J = 53.3, 12.7 Hz, 2H), 2.83 (s, 3H), 1.11 (s, 9H). |
| 61 | 3-acetyl-8-bromo-5-chloro-2-((methoxymethyl)thio)quinolin-4(1H)-one | 376.65 | 376 | $^1$H NMR (300 MHz, CDCl$_3$)δ10.62(br, 1H), 7.69(d, J = 8.4 Hz, 1H), 7.24 (d, J = 8.4 Hz, 1H), 5.07 (s, 2H), 3.66 (s, 3H), 2.69 (s, 3H). |
| 62 | 3-acetyl-8-bromo-5-chloro-2-mercaptoquinolin-4(1H)-one | 332.60 | 332 | $^1$H NMR (300 MHz, CDCl$_3$)δ10.11(br, 1H), 7.74(d, J = 8.5 Hz, 1H), 7.21 (d, J = 8.5 Hz, 1H), 3.15 (s, 3H). |

TABLE 4-continued

| Compound Number | Formula Name | MW (Molecular Weight) | LC/MS data | ¹H NMR |
|---|---|---|---|---|
| 63 | 3-acetyl-2-((4-benzoylbenzyl)sulfinyl)-8-bromo-5-chloroquinolin-4(1H)-one | 542.83 | 542 | ¹H NMR (300 MHz, CDCl₃)δ10.29(br, 1H), 7.67(d, J = 8.4 Hz, 1H), 7.61 (d, J = 8.2 Hz, 2H), 7.37-7.59 (m, 5H), 7.31 (d, J = 8.4 Hz, 1H), 7.23 (d, J = 8.2 Hz, 2H), 4.51 (q, J = 12.6 Hz, 2H), 2.85 (s, 3H). |
| 64 | 3-acetyl-8-bromo-5-chloro-2-((4-((trifluoromethyl)sulfinyl)benzyl)sulfinyl)quinolin-4(1H)-one | 554.78 | 554 | ¹H NMR (300 mhz, CDCl₃)δ10.30 (br s, 1H), 7.70-7.62(m, 3H), 7.41-7.26(m, 3H), 4.55-4.45(q, J = 16.3 Hz, 2H), 2.84 (s, 3H). |
| 65 | 2-((3-acetyl-8-bromo-5-chloro-4-oxo-1,4-dihydroquinolin-2-yl)sulfinyl)acetonitrile | 387.63 | 387 | ¹H NMR (300 MHz, CDCl₃)δ10.97(br, 1H), 7.87(d, J = 8.4 Hz, 1H), 7.43 (d, J = 8.5 Hz, 1H), 4.27 (q, J = 16.3 Hz, 2H), 2.84 (s, 3H). |
| 66 | 2-((3-acetyl-8-bromo-5-chloro-4-oxo-1,4-dihydroquinolin-2-yl)thio)acetonitrile | 371.63 | 371 | ¹H NMR (300 MHz, CDCl₃)δ7.96(d, J = 8.3 Hz, 1H), 7.36 (d, J = 8.3 Hz, 1H), 4.30 (s, 2H), 2.94 (s, 3H). |
| 67 | (Z)-3-((3-acetyl-8-bromo-5-chloro-4-oxo-1,4-dihydroquinolin-2-yl)thio)acrylic acid | 402.64 | 402 | ¹H NMR (300 MHz, MeOD) δ9.03 (br, 0.5H), 8.84 (br, 1H), 7.97 (d, J = 8.2 Hz, 1H), 7.91 (d, J = 8.3 Hz, 0.5H), 7.37 (d, J = 8.4 Hz, 1H), 7.31 (d, J = 8.3 Hz, 0.5H), 6.34 (d, J = 10.8 Hz, 0.5H), 6.22 (d, J = 10.3 Hz, 1H), 2.78 (s, 3H), 2.72 (s, 1.5H). |
| 68 | 3-acetyl-8-bromo-5-chloro-2-((4-(pentafluoro-16-sulfanyl)benzyl)sulfinyl)quinolin-4(1H)-one | 564.76 | 564 | ¹H NMR (300 MHz, CDCl₃)δ10.14 (s, 1H), 7.71 (d, J = 8.4 Hz, 1H), 7.57 (d, J = 8.7 Hz, 2H), 7.33 (d, J = 8.5 Hz, 1H), 7.20 (d, J = 8.3 Hz, 2H), 4.47 (dd, J = 30.2, 12.6 Hz, 2H), 2.87 (s, 3H). |
| 69 | 3-acetyl-8-bromo-5-chloro-2-((-fluoro-4-(pentafluoro-16-sulfanyl)benzyl)sulfinyl)quinolin-4(1H)-one | 582.75 | 582 | ¹H NMR (300 MHz, CDCl₃)δ10.19(s, 1H), 7.71-7.68(d, J = 8.43 Hz, 1H), 7.33-7.30(d, J = 8.31 Hz, 1H), 4.73-4.40(q, J = 13.0, 72.1 Hz, 2H), 2.83(s, 3H). |
| 70 | 3-acetyl-8-bromo-5-chloro-2-((4-(trifluoromethyl)benzyl)sulfinyl)quinolin-4(1H)-one | 506.72 | 506 | ¹H NMR (300 MHz, CDCl₃)δ10.16 (s, 1H), 7.71 (d, J = 8.4 Hz, 1H), 7.46 (d, J = 8.1 Hz, 2H), 7.33 (d, J = 8.4 Hz, 1H), 7.25 (d, J = 8.0 Hz, 2H), 4.60-4.34 (m, 2H), 2.87 (s, 3H). |
| 71 | 3-acetyl-8-bromo-5-chloro-2-((4-(trifluoromethoxy)benzyl)sulfinyl)quinolin-4(1H)-one | 522.72 | 522 | ¹H NMR (300 MHz, CDCl₃)δ10.24(br, 1H), 7.69(d, J = 8.5 Hz, 1H), 7.30 (d, J = 8.4 Hz, 1H), 7.14 (d, J = 8.7 Hz, 2H), 7.04 (d, J = 8.1 Hz, 2H), 4.42 (q, J = 12.8 Hz, 2H), 2.84 (s, 3H). |
| 72 | 3-acetyl-8-bromo-5-chloro-2-(((5-(trifluoromethyl)furan-2-yl)methyl)sulfinyl)quinolin-4(1H)-one | 496.68 | 496 | ¹H NMR (300 MHz, CDCl₃)δ10.34 (s, 1H), 7.75 (d, J = 8.5 Hz, 1H), 7.36 (d, J = 8.4 Hz, 1H), 6.71 (s, 1H), 6.59 (d, J = 3.1 Hz, 1H), 4.58 (dd, J = 71.0, 14.1 Hz, 2H), 2.87 (s, 3H). |
| 73 | 4-(((3-acetyl-8-bromo-5-chloro-4-oxo-1,4-dihydroquinolin-2-yl)sulfinyl)methyl)benzonitrile | 463.73 | 463 | ¹H NMR (300 MHz, CDCl₃)δ10.21(s, 1H), 775-7.72(d, J = 8.4 Hz, 1H), 7.52-7.50(d, J = 8.04 Hz, 2H), 7.36-7.33(d, J = 8.43 Hz, 1H), 7.27-7.25(d, J = 8.1 Hz, 2H), 4.50-4.39(q, J = 12.4, 6.33 Hz, 2H), 2.84(s, 3H). |
| 74 | 3-acetyl-8-bromo-5-chloro-2-((2-chloro-6-fluorobenzyl)sulfinyl)quinolin-4(1H)-one | 491.15 | 491 | ¹H NMR (300 MHz, CDCl₃)δ10.6(s, 1H), 7.75-7.72(d, J = 8.4 Hz, 1H), 7.35-7.33(d, J = 8.4 Hz, 1H), 7.31-7.28(m, 1H), 7.24-7.18(t, J = 8.8 Hz, 1H), 7.01-6.96(t, J = 8.0 Hz, 1H), 5.08-5.05(q, J = 1.9, 11, 120 Hz, 2H), 2.82(s, 3H). |
| 75 | 3-acetyl-8-bromo-5-chloro-2-((2-methoxy-4-(pentafluoro-16-sulfanyl)benzyl)sulfinyl)quinolin-4(1H)-one | 594.79 | 594 | ¹H NMR (300 MHz, CDCl₃)δ10.26(s, 1H), 7.69-7.67(d, J = 8.40 Hz, 1H), 7.31-7.28(d, J = 8.43 Hz, 1H), 4.80-4.40(q, J = 13.0, 95.7 Hz, 2H), 2.82(s, 3H). |
| 76 | 3-acetyl-8-bromo-5-chloro-2-((3-fluoro-5-(pentafluoro-16-sulfanyl)benzyl)sulfinyl)quinolin-4(1H)-one | 582.75 | 582 | ¹H NMR (300 MHz, CDCl₃)δ10.13 (s, 1H), 7.70 (d, J = 8.5 Hz, 1H), 7.38 (s, 1H), 7.33 (d, J = 8.6 Hz, 1H), 7.21 (d, J = 8.1 Hz, 1H), 7.09 (s, 1H), 4.44 (s, 2H), 2.84 (s, 3H). |

TABLE 4-continued

| Compound Number | Formula Name | MW (Molecular Weight) | LC/MS data | $^1$H NMR |
|---|---|---|---|---|
| 77 | 3-acetyl-8-bromo-5-chloro-2-((3-(pentafluoro-16-sulfanyl)benzyl)sulfinyl)quinolin-4(1H)-one | 564.76 | 564 | $^1$H NMR (300 MHz, CDCl$_3$)δ10.06 (s, 1H), 7.59-7.68 (m, 2H), 7.29-7.38 (m, 4H), 4.47 (q, J = 12.8 Hz, 2H), 2.85 (s, 3H). |
| 78 | 3-acetyl-8-bromo-5-chloro-2-(((perfluorophenyl)methyl)sulfinyl)quinolin-4(1H)-one | 528.67 | 528 | $^1$H NMR (300 MHz, CDCl$_3$)δ10.48(s, 1H), 7.79-7.77(d, J = 8.43 Hz, 1H), 7.38-7.36(d, J = 8.31 Hz, 1H), 4.49-4.40(q, J = 13.0, 128 Hz, 1H), 2.83(s, 3H). |
| 79 | 3-acetyl-5, 8-dichloro-2-((4-((trifluoromethyl)thio)benzyl)sulfinyl)quinolin-4(1H)-one | 494.32 | 494 | $^1$H NMR (300 MHz, CDCl$_3$)δ10.24(br s, 1H), 7.56-7.49 (m, 4H), 7.39-7.37(d, J = 8.52 Hz, 2H), 7.21-7.18(d, J = 7.68 Hz, 2H), 4.52-4.40(q, J = 13.4 Hz, 2H), 2.87(s, 3H). |
| 80 | 3-acetyl-5,8-difluoro-2-((4-(pentafluoro-16-sulfanyl)benzyl)sulfinyl)quinolin-4(1H)-one | 487.40 | 487 | $^1$H NMR (300 MHz, CDCl$_3$)δ9.78(br s, 1H), 7.59-7.58 (d, J = 8.49 Hz, 1H), 7.37-7.22(m, 3H), 7.06-6.98(m, 1H), 4.41(s, 2H), 2.84(s, 3H). |
| 81 | 3-acetyl-5,8-difluoro-2-(((5-(trifluoromethyl)furan-2-yl)methyl)sulfinyl)quinolin-4(1H)-one | 419.32 | 419 | $^1$H NMR (300 MHz, CDCl$_3$)δ9.93(br s, 1H), 7.41-7.33(m, 1H), 7.08-7.00 (m, 1H), 6.71-6.69(m, 1H), 6.56-6.55(m, 1H), 4.66(d, J = 14.1 Hz, 1H), 4.48-4.44(d, J = 14.07 Hz, 1H), 2.83(s, 3H). |
| 82 | 3-acetyl-5,8-difluoro-2-(((5-methylisoxazol-3-yl)methyl)sulfinyl)quinolin-4(1H)-one | 366.34 | 366 | $^1$H NMR (300 MHz, CDCl$_3$)δ 10.45(br s, 1H), 7.61-7.59(d, J = 8.49 Hz, 2H), 7.41-7.38 (d, J = 8.46 Hz, 1H), 6.16(s, 1H), 4.51-4.39(q, J = 13.5, 21.8 Hz, 2H), 2.81(s, 3H), 2.37(s, 3H). |
| 83 | 3-acetyl-5, 8-dichloro-2-((4-iodobenzyl)sulfinyl)quinolin-4(1H)-one | 520.16 | 520 | $^1$H NMR (300 MHz, CDCl$_3$)δ10.11(br s, 1H), 7.60-7.57(d, J = 8.46 Hz, 1H), 7.51-7.49 (d, J = 8.22 Hz, 2H), 7.40-7.37(d, J = 8.43 Hz, 1H), 6.83-6.81(d, J = 8.22 Hz, 2H), 4.32(s, 2H), 2.83(s, 3H). |
| 84 | 3-acetyl-8-bromo-5-chloro-2-((pyridin-3-ylmethyl)sulfinyl)quinolin-4(1H)-one | 439.71 | 439 | $^1$H NMR (300 MHz, DMSO) δ8.41 (d, J = 4.6 Hz, 1H), 8.21 (s, 1H), 7.99 (d, J = 8.5 Hz, 1H), 7.52 (d, J = 7.9 Hz, 1H), 7.44 (d, J = 8.5 Hz, 1H), 7.25 (dd, J = 7.6, 4.6 Hz, 1H), 4.71 (d, J = 13.1 Hz, 1H), 4.37 (d, J = 13.0 Hz, 1H), 2.68 (s, 3H). |
| 85 | 5,8-difluoro-3-isobutyryl-2-((4-((trifluoromethyl)thio)benzyl)sulfinyl)quinolin-4(1H)-one | 489.48 | 489 | $^1$H NMR (300 MHz, CDCl$_3$+ MeOD)δ7.60-6.92(m, 6H), 4.45-4.41(m, 1H), 4.35-4.31(m, 1H), 4.09-4.00 (m, 1H), 1.19-1.17(d, J = 6 Hz, 3H), 1.11-1.08(d, J = 7.17 Hz, 3H). |
| 86 | 5,8-dichloro-3-isobutyryl-2-(((5-methylisoxazol-3-yl)methyl)sulfinyl)quinolin-4(1H)-one | 427.30 | 427 | $^1$H NMR (300 MHz, CDCl$_3$)δ10.43(br s, 1H), 7.59-7.56(d, J = 8.43 Hz, 1H), 7.38-7.35(d, J = 8.43 Hz, 1H), 6.13(s, 1H), 4.50-4.39(d, J = 8.54 Hz, 2H), 4.14-4.05(m, 1H), 2.34(s, 3H). 1.21-1.15(dd, J = 6.8, 11.6 Hz, 6H). |
| 87 | 3-benzoyl-5,8-difluoro-2-((4-(pentafluoro-16-sulfanyl)benzyl)sulfinyl)quinolin-4(1H)-one | 549.48 | 549 | $^1$H NMR (300 MHz, CDCl$_3$)δ7.74-7.27(m, 10H), 7.00-6.92 (m, 1H), 4.80-4.76(d, J = 12.66 Hz, 1H), 4.53-4.49(d, J = 12.6 Hz, 1H). |
| 88 | 3-benzoyl-5,8-dichloro-2-(((5-methylisoxazol-3-yl)methyl)sulfinyl)quinolin-4(1H)-one | 461.31 | 461 | $^1$H NMR (300 MHz, CDCl$_3$)δ7.77-7.75(d, J = 6.75 Hz, 2H), 7.74-7.70 (d, J = 8.28 Hz, 1H), 7.59-7.3 l(m, 5H), 6.18(s, 1H), 4.68(s, 2H), 3.10(s, 3H). |
| 89 | methyl 5-(((3-acetyl-5,8-dichloro-4-oxo-1,4-dihydroquinolin-2-yl)sulfinyl)methyl)furan-2-carboxylate | 442.26 | 442 | $^1$H NMR (300 MHz, CDCl$_3$)δ10.24 (s, 1H), 7.56 (d, J = 8.5 Hz, 1H), 7.38 (d, J = 8.5 Hz, 1H), 7.05 (d, J = 3.4 Hz, 1H), 6.59 (d, J = 3.4 Hz, 1H), 4.65 (d, J = 13.9 Hz, 1H), 4.44 (d, J = 13.9 Hz, 1H), 3.60 (s, 3H), 2.85 (s, 3H). |
| 90 | 2-(((3-acetyl-5, 8-dichloro-4-oxo-1,4-dihydroquinolin-2-yl)sulfinyl)methyl)isoindoline-1,3-dione | 463.29 | 463 | $^1$H NMR (300 MHz, CDCl$_3$)δ10.52 (s, 1H), 8.00-7.74 (m, 4H), 7.62 (d, J = 8.4 Hz, 1H), 7.43 (d, J = 8.5 Hz, 1H), 5.74 (d, J = 12.6 Hz, 1H), 4.86 (d, J = 12.6 Hz, 1H), 2.87 (s, 3H). |

TABLE 4-continued

| Compound Number | Formula Name | MW (Molecular Weight) | LC/MS data | $^1$H NMR |
|---|---|---|---|---|
| 91 | methyl 4-(((3-acetyl-5, 8-dichloro-4-oxo-1,4-dihydroquinolin-2-yl)sulfinyl)methyl)benzoate | 452.30 | 452 | $^1$H NMR (300 MHz, CDCl$_3$)δ10.23 (s, 1H), 7.87 (d, J = 8.2 Hz, 2H), 7.52 (d, J = 8.4 Hz, 1H), 7.36 (d, J = 8.4 Hz, 1H), 7.23 (d, J = 8.2 Hz, 2H), 4.44 (q, J = 12.5 Hz, 2H), 3.89 (d, J = 5.4 Hz, 3H), 2.85 (s, 3H). |
| 92 | 3-acetyl-5-methoxy-2-((4-(pentafluoro-16-sulfanyl)benzyl)thio)quinolin-4(1H)-one | 465.45 | 465 | $^1$H NMR (300 MHz, CDCl$_3$)δ8.18 (d, J = 9.0 Hz, 1H), 7.71 (d, J = 8.7 Hz, 2H), 7.60 (d, J = 8.4 Hz, 2H), 7.14 (d, J = 2.4 Hz, 1H), 7.08 (dd, J = 9.0, 2.5 Hz, 1H), 4.70 (s, 2H), 4.00 (s, 3H), 2.92 (s, 3H). |
| 93 | 3-acetyl-5-methoxy-2-((4-(pentafluoro-16-sulfanyl)benzyl)sulfinyl)quinolin-4(1H)-one | 481.45 | 481 | $^1$H NMR (300 MHz, CDCl$_3$)δ9.63 (s, 1H), 8.28 (d, J = 9.0 Hz, 1H), 7.57 (d, J = 8.6 Hz, 2H), 7.23 (s, 1H), 7.04 (dd, J = 9.0, 2.2 Hz, 1H), 6.54 (d, J = 2.2 Hz, 1H), 4.39 (dd, J = 36.0, 12.5 Hz, 2H), 3.87 (d, J = 10.5 Hz, 3H), 2.87 (s, 3H). |
| 94 | 3-acetyl-5-methoxy-2-(((5-methylisoxazol-3-yl)methyl)sulfinyl)quinolin-4(1H)-one | 360.38 | 360 | $^1$H NMR (300 MHz, CDCl$_3$)δ10.43 (s, 1H), 8.34 (d, J = 9.0 Hz, 1H), 7.08 (d, J = 8.9 Hz, 1H), 6.93 (s, 1H), 6.08 (s, 1H), 4.45 (dd, J = 60.6, 13.3 Hz, 2H), 3.91 (s, 3H), 2.87 (s, 3H), 2.32 (s, 3H). |
| 95 | 8-bromo-5-chloro-3-isobutyryl-2-(((5-methylisoxazol-3-yl)methyl)sulfinyl)quinolin-4(1H)-one | 471.75 | 471 | $^1$H NMR (300 MHz, CDCl$_3$)δ10.49(br s, 1H), 7.75-7.72 (d, J = 8.43 Hz, 1H), 7.34-7.3 l(d, J = 8.37 Hz, 1H), 6.13(s, 1H), 4.47(s, 2H), 4.16-4.07(m, 1H), 2.35(s, 3H), 1.23-1.17(dd, J = 6.7, 12.0 Hz, 6H). |
| 96 | 8-bromo-5-chloro-3-(cyclopropanecarbonyl)-2-(((5-methylisoxazol-3-yl)methyl)sulfinyl)quinolin-4(1H)-one | 469.73 | 469 | $^1$H NMR (300 MHz, CDCl$_3$)δ10.44(br s, 1H), 7.75-7.72 (d, J = 8.43 Hz, 1H), 7.34-7.3 l(d, J = 8.4 Hz, 1H), 6.11(s, 1H), 4.48-4.37(q, J = 10.5 Hz, 2H), 3.70-3.62(m, 1H), 2.35(s, 3H), 1.28-1.05(m, 4H). |
| 97 | 5,8-dichloro-3-(cyclopropanecarbonyl)-2-(((5-methylisoxazol-3-yl)methyl)sulfinyl)quinolin-4(1H)-one | 425.28 | 425 | $^1$H NMR (300 MHz, CDCl$_3$)δ10.42(br s, 1H), 7.61-7.58 (d, J = 8.43 Hz, 1H), 7.41-7.38(d, J = 8.43 Hz, 1H), 6.12(s, 1H), 4.49-4.37(q, J = 1 1.7 Hz, 2H), 3.71-3.62(m, 1H), 2.36(s, 3H), 1.29-1.06(m, 4H). |
| 98 | 5-(((3-acetyl-8-bromo-5-chloro-4-oxo-1,4-dihydroquinolin-2-yl)sulfinyl)methyl)thiophene-2-carbonitrile | 469.75 | 469 | $^1$H NMR (300 MHz, CDCl$_3$)δ10.31(br s, 1H), 7.79-7.77 (d, J = 8.43 Hz, 1H), 7.42-7.36(m, 2H), 6.91-6.86(d, J = 3.84 Hz, 1H), 4.77-4.72(d, J = 13.74 , 1H), 4.63-4.59(d, J = 13.71, 1H), 2.86(s, 3H). |
| 99 | 2-(((6-(1H-pyrazol-1-yl)pyridin-3-yl)methyl)sulfinyl)-3-acetyl-8-bromo-5-chloroquinolin-4(1H)-one | 505.77 | 505 | $^1$H NMR (300 MHz, DMSO-d$_6$)δ10.00(br s, 1H), 8.46-8.45 (s, 1H), 8.1 l(s, 1H), 7.89-7.86(d, J = 8.46 Hz, 1H), 7.80(s, 1H), 7.79-7.71(m, 2H), 7.41-7.38(d, J = 8.37 Hz, 1H), 6.55(s, 1H), 4.79-4.75(d, J = 12.99 Hz, 1H), 4.43-4.38(d, J = 13.08 Hz, 1H), 2.70(s, 3H). |
| 100 | 3-acetyl-2-(((6-aminopyridin-3-yl)methyl)sulfinyl)-8-bromo-5-chloroquinolin-4(1H)-one | 454.72 | 454 | $^1$H NMR (300 MHz, DMSO-d$_6$)δ8.22-7.65 (m, 4H), 7.09-7.06(m, 1H), 4.36-4.32(m, 1H), 4.14-4.11(m, 1H), 2.88(s, 3H). |
| 101 | 8-bromo-5-chloro-3-(cyclopropanecarbonyl)-2-((4-((trifluoromethyl)thio)benzyl)sulfinyl)quinolin-4(1H)-one | 564.82 | 564 | $^1$H NMR (300 MHz, DMSO-d$_6$)δ10.11(br s, 1H), 8.08-8.06 (d, J = 8.43 Hz, 1H), 7.55-7.52(d, J = 7.71 Hz, 2H), 7.45-7.43(d, J = 8.37 Hz, 1H), 7.20-7.17(d, J = 7.71 Hz, 2H), 4.65-4.61(d, J = 12.66 Hz, 1H), 4.42-4.37(d, J = 12.87 Hz, 1H), 3.55-3.47(m, 1H), 1.28-1.02(m, 4H). |
| 102 | 3-acetyl-8-bromo-5-chloro-2-(((2-methyl-6-(trifluoromethyl)pyridin-3-yl)methyl)sulfinyl)quinolin-4(1H)-one | 521.73 | 521 | $^1$H NMR (300 MHz, DMSO-d$_6$)δ10.32(br s, 1H), 8.02-7.99(d, J = 8.46 Hz, 1H), 7.68-7.65(d, J = 7.98 Hz, 1H), 7.55-7.52(d, J = 7.89 Hz, 1H), 7.45-7.42(d, J = 8.49 Hz, 1H), 4.95-4.91(d, J = 13.41 Hz, 1H), 4.51-4.46(d, J = 13.08 Hz, 2H), 2.68(s, 3H), 2.61(s, 3H). |

TABLE 4-continued

| Compound Number | Formula Name | MW (Molecular Weight) | LC/MS data | $^1$H NMR |
|---|---|---|---|---|
| 103 | N-(4-(((3-acetyl-8-bromo-5-chloro-4-oxo-1,4-dihydroquinolin-2-yl)sulfinyl)methyl)phenyl)methanesulfonamide | 531.82 | 531 | $^1$H NMR (300 MHz, DMSO-d$_6$)δ10.25(br s, 1H), 8.01 (m, 1H), 7.67-7.64(m, 1H), 7.41-6.98(m, 6H), 4.79-4.50(m, 2H), 4.30-4.22(m, 2H), 2.81(s, 3H), 2.68(s, 3H). |
| 104 | 3-acetyl-8-bromo-5-chloro-2-(((6-chloropyridin-3-yl)methyl)sulfinyl)quinolin-4(1H)-one | 474.15 | 474 | $^1$H NMR (300 MHz, CDCl$_3$)δ10.20 (s, 1H), 8.10 (s, 1H), 7.76 (d, J = 8.4 Hz, 1H), 7.51 (d, J = 7.8 Hz, 1H), 7.36 (d, J = 8.4 Hz, 1H), 7.24 (d, J = 8.1 Hz, 1H), 4.41 (dd, J = 26.8, 13.0 Hz, 2H), 2.86 (s, 3H). |
| 105 | 3-acetyl-8-bromo-5-chloro-2-(((6-((2-methoxyethyl)amino)pyridin-3-yl)methyl)sulfinyl)quinolin-4(1H)-one | 512.80 | 512 | $^1$H NMR(300 MHz, CDCl$_3$) δ 12.59 (s, 1H), 7.75 (d, J = 8.2 Hz, 1H), 7.63 (d, J = 7.6 Hz, 1H), 7.04 (d, J = 8.2 Hz, 2H), 6.11 (d, J = 7.6 Hz, 1H), 4.61-4.53 (m, 1H), 3.90-3.84 (m, 1H), 3.71-3.65 (m, 2H), 3.64-3.55 (m, 2H), 3.41 (s, 3H), 3.33 (s, 3H). |
| 106 | 3-acetyl-8-bromo-5-chloro-2-(((4-methyl-1,2,5-oxadiazol-3-yl)methyl)sulfinyl)quinolin-4(1H)-one | 444.68 | 444 | $^1$H NMR (300 MHz, DMSO-d$_6$)δ 7.76-7.73(d, J = 8.5 Hz, 1H), 7.08-7.06(d, J = 8.5 Hz, 1H), 4.52-4.48(d, J = 12.0 Hz, 1H), 4.28-4.23 (d, J = 12.0 Hz, 1H), 2.50(s, 3H), 2.44(s, 3H). |
| 107 | 2-(((1H-pyrrolo[2,3-b]pyridin-5-yl)methyl)sulfinyl)-3-acetyl-8-bromo-5-chloroquinolin-4(1H)-one | 478.75 | 478 | $^1$H NMR (300 MHz, DMSO-d$_6$)δ11.62(br s, 1H), 8.00-7.32 (m, 5H), 6.38(s, 1H), 4.62-4.58(m, 1H), 4.20-4.10(m, 1H), 2.60(s, 3H). |

Evaluation of Compounds of the Present Disclosure

Evaluation of Inhibitory Effect of Compounds on DNA Binding of c-Myc/Max

1. Protein Assay

1) Preparation of Recombinant c-Myc and Max Proteins

Recombinant proteins were prepared as described in the following references: K. C. Jung et al., Fatty Acids, Inhibitors for the DNA Binding of c-Myc/Max Dimer, Suppress Proliferation and Induce Apoptosis of Differentiated HL-60 Human Leukemia Cell, Leukemia, 2006, 20(1), 122-7 or Kyung-Chae Jeong et al., Small-Molecule Inhibitors of c-Myc Transcriptional Factor Suppress Proliferation and Induce Apoptosis of Promyelocytic Leukemia Cell via Cell Cycle Arrest, Mol. BioSyst., 2010, 6, 1503-1509.

2) Electrophoretic Mobility Shift Assay (EMSA)

The inhibitory activity of each candidate compound on DNA binding of recombinant c-Myc/Max was measured using an electrophoretic mobility shift assay (EMSA). The ratio of protein-DNA complexes in each sample was evaluated by measuring band intensity. The oligonucleotides (E-box) corresponding to the consensus binding site of Myc/Max were dimerized through an annealing process. The protein mixture was incubated at room temperature for 5 minutes, and a DMSO solution containing each candidate compound was added thereto. The mixture was further incubated for 5 minutes, and the biotinylated DNA was added. To achieve a state of equilibrium, the final mixture was incubated at room temperature for 10 minutes. The protein-DNA complexes were separated from unbound free DNA by pre-electrophoresis using 8% polyacrylamide gel and 1×TBE buffer. After pre-electrophoresis, electrophoresis was performed at 120 V for 1 hour in 1×TBE buffer. Each band was visualized using HRP-conjugated streptavidin and an ECL solution, and band intensity was measured using image analysis software.

2. Cell Based Assay

Commercially available bladder cancer cell lines were treated with trypsin-EDTA and seeded in each well of a 96 well plate, followed by incubation for 24 hours. After incubation, candidate compounds were added to each well at a final concentration of 0 to 2 μM. The compound-treated cells were further incubated for 72 hours. Cell viability was measured using an ATP detection method (CellTiter-Glo® Luminescent Cell Viability Assay, Promega).

IC$_{50}$ values calculated from an in vitro assay and a proliferation assay using compounds according to the present disclosure are summarized in Table 5 below.

TABLE 5

| Compound Number | protein assay | cell based assay ||||
|---|---|---|---|---|---|
| | | cell line 1 MBT-2 | cell line 2 KU19-19 | cell line 3 253J | cell line 4 UM-UC-3 |
| 1 | <1 μM | 1.19 μM | 1.94 μM | 1.35 μM | 1.51 μM |
| 2 | <1 μM | >2 μM | >2 μM | >2 μM | >2 μM |
| 3 | <1 μM | >2 μM | >2 μM | >2 μM | >2 μM |
| 4 | <1 μM | 0.96 μM | 1.05 μM | 1.00 μM | 1.33 μM |
| 5 | <1 μM | >2 μM | >2 μM | >2 μM | >2 μM |
| 6 | <1 μM | 1.44 μM | >2 μM | 1.22 μM | 1.46 μM |
| 7 | <1 μM | >2 μM | >2 μM | >2 μM | >2 μM |
| 8 | <1 μM | >2 μM | >2 μM | >2 μM | >2 μM |
| 9 | <1 μM | 1.20 μM | 1.97 μM | 1.10 μM | 1.18 μM |
| 10 | <1 μM | >2 μM | >2 μM | >2 μM | >2 μM |
| 11 | <1 μM | >2 μM | >2 μM | 1.41 μM | 1.49 μM |
| 12 | <1 μM | >2 μM | >2 μM | >2 μM | >2 μM |
| 13 | <1 μM | >2 μM | >2 μM | >2 μM | >2 μM |
| 14 | <1 μM | >2 μM | >2 μM | >2 μM | >2 μM |
| 15 | <1 μM | >2 μM | 1.91 μM | >2 μM | >2 μM |
| 16 | <1 μM | >2 μM | >2 μM | >2 μM | >2 μM |
| 17 | <1 μM | >2 μM | >2 μM | >2 μM | >2 μM |
| 18 | <1 μM | >2 μM | >2 μM | >2 μM | >2 μM |
| 19 | <1 μM | >2 μM | >2 μM | >2 μM | >2 μM |
| 20 | <1 μM | >2 μM | >2 μM | >2 μM | >2 μM |
| 21 | <1 μM | >2 μM | >2 μM | >2 μM | >2 μM |
| 22 | <1 μM | >2 μM | >2 μM | >2 μM | >2 μM |

TABLE 5-continued

| | | cell based assay | | | |
|---|---|---|---|---|---|
| Compound Number | protein assay | cell line 1 MBT-2 | cell line 2 KU19-19 | cell line 3 253J | cell line 4 UM-UC-3 |
| 23 | <1 μM | >2 μM | >2 μM | >2 μM | >2 μM |
| 24 | <1 μM | >2 μM | >2 μM | >2 μM | >2 μM |
| 25 | <1 μM | >2 μM | >2 μM | >2 μM | >2 μM |
| 26 | <1 μM | >2 μM | >2 μM | >2 μM | >2 μM |
| 27 | <1 μM | >2 μM | >2 μM | >2 μM | >2 μM |
| 28 | <1 μM | 0.79 μM | 1.46 μM | 0.74 μM | 0.79 μM |
| 29 | <1 μM | 1.20 μM | 1.68 μM | 0.96 μM | 1.13 μM |
| 30 | <1 μM | >2 μM | >2 μM | >2 μM | >2 μM |
| 31 | <1 μM | 1.28 μM | 1.45 μM | 0.89 μM | 1.02 μM |
| 32 | <1 μM | >2 μM | >2 μM | >2 μM | >2 μM |
| 33 | <1 μM | 0.90 μM | 1.42 μM | 1.39 μM | 1.11 μM |
| 34 | <1 μM | >2 μM | >2 μM | >2 μM | >2 μM |
| 35 | <1 μM | >2 μM | >2 μM | >2 μM | >2 μM |
| 36 | <1 μM | 1.28 μM | >2 μM | >2 μM | >2 μM |
| 37 | <1 μM | >2 μM | >2 μM | >2 μM | >2 μM |
| 38 | <1 μM | >2 μM | >2 μM | >2 μM | >2 μM |
| 39 | <1 μM | >2 μM | >2 μM | >2 μM | >2 μM |
| 40 | <1 μM | >2 μM | >2 μM | >2 μM | >2 μM |
| 41 | <1 μM | >2 μM | >2 μM | >2 μM | >2 μM |
| 42 | <1 μM | >2 μM | >2 μM | >2 μM | 1.89 μM |
| 43 | <1 μM | >2 μM | >2 μM | >2 μM | >2 μM |
| 44 | <1 μM | 1.15 μM | 1.27 μM | 1.24 μM | 0.97 μM |
| 45 | <1 μM | >2 μM | >2 μM | >2 μM | >2 μM |
| 46 | <1 μM | 1.84 μM | 1.80 μM | 1.96 μM | 1.22 μM |
| 47 | <1 μM | >2 μM | >2 μM | >2 μM | >2 μM |
| 48 | <1 μM | >2 μM | >2 μM | >2 μM | 1.82 μM |
| 49 | <1 μM | >2 μM | >2 μM | >2 μM | >2 μM |
| 50 | <1 μM | 1.58 μM | 1.69 μM | 1.43 μM | 1.26 μM |
| 51 | <1 μM | 0.76 μM | 1.26 μM | 1.13 μM | 0.63 μM |
| 52 | <1 μM | >2 μM | >2 μM | >2 μM | >2 μM |
| 53 | <1 μM | >2 μM | >2 μM | >2 μM | >2 μM |
| 54 | <1 μM | >2 μM | >2 μM | >2 μM | >2 μM |
| 55 | <1 μM | >2 μM | 1.38 μM | 1.33 μM | 1.58 μM |
| 56 | <1 μM | 1.18 μM | 0.94 μM | 1.11 μM | 1.25 μM |
| 57 | <1 μM | >2 μM | 1.83 μM | 1.92 μM | >2 μM |
| 58 | <1 μM | 0.86 μM | 0.92 μM | 0.92 μM | 1.22 μM |
| 59 | <1 μM | 1.30 μM | 1.23 μM | 1.14 μM | 1.37 μM |
| 60 | <1 μM | >2 μM | 1.56 μM | 1.71 μM | >2 μM |
| 61 | <1 μM | >2 μM | >2 μM | >2 μM | >2 μM |
| 62 | <1 μM | >2 μM | >2 μM | >2 μM | >2 μM |
| 63 | <1 μM | >2 μM | >2 μM | >2 μM | >2 μM |
| 64 | <1 μM | 0.84 μM | 1.41 μM | 0.95 μM | 1.06 μM |
| 65 | <1 μM | >2 μM | >2 μM | >2 μM | >2 μM |
| 66 | <1 μM | >2 μM | >2 μM | >2 μM | >2 μM |
| 67 | <1 μM | >2 μM | >2 μM | >2 μM | >2 μM |
| 68 | <1 μM | 1.07 μM | 1.25 μM | 0.97 μM | 1.11 μM |
| 69 | <1 μM | 1.26 μM | 1.50 μM | 1.08 μM | 1.20 μM |
| 70 | <1 μM | 1.33 μM | 1.75 μM | 1.04 μM | 1.26 μM |
| 71 | <1 μM | 1.47 μM | 1.60 μM | 1.11 μM | 1.61 μM |
| 72 | <1 μM | 1.01 μM | 1.37 μM | 0.83 μM | 0.82 μM |
| 73 | <1 μM | 1.00 μM | 2.00 μM | 1.34 μM | 1.62 μM |
| 74 | <1 μM | 1.15 μM | 1.64 μM | 0.81 μM | 1.54 μM |
| 75 | <1 μM | 1.05 μM | 1.21 μM | 0.86 μM | 1.01 μM |
| 76 | <1 μM | 1.86 μM | 1.86 μM | 1.24 μM | 1.39 μM |
| 77 | <1 μM | 1.45 μM | 1.38 μM | 0.90 μM | 1.18 μM |
| 78 | <1 μM | 1.53 μM | >2 μM | 1.29 μM | 1.39 μM |
| 79 | <1 μM | >2 μM | >2 μM | >2 μM | >2 μM |
| 80 | <1 μM | >2 μM | >2 μM | >2 μM | >2 μM |
| 81 | <1 μM | >2 μM | >2 μM | >2 μM | >2 μM |
| 82 | <1 μM | >2 μM | >2 μM | >2 μM | >2 μM |
| 83 | <1 μM | 1.35 μM | 1.60 μM | 1.42 μM | 1.31 μM |
| 84 | <1 μM | 0.67 μM | 1.50 μM | 0.87 μM | 0.76 μM |
| 85 | <1 μM | >2 μM | >2 μM | >2 μM | >2 μM |
| 86 | <1 μM | 0.81 μM | 1.41 μM | 1.06 μM | 1.26 μM |
| 87 | <1 μM | >2 μM | >2 μM | >2 μM | >2 μM |
| 88 | <1 μM | >2 μM | >2 μM | >2 μM | >2 μM |
| 89 | <1 μM | 1.27 μM | >2 μM | 1.84 μM | 1.47 μM |
| 90 | <1 μM | >2 μM | >2 μM | >2 μM | >2 μM |
| 91 | <1 μM | 1.37 μM | >2 μM | >2 μM | 1.56 μM |
| 92 | <1 μM | >2 μM | >2 μM | >2 μM | >2 μM |
| 93 | <1 μM | >2 μM | >2 μM | >2 μM | >2 μM |
| 94 | <1 μM | 1.53 μM | >2 μM | >2 μM | >2 μM |
| 95 | <1 μM | 0.80 μM | 1.29 μM | 0.77 μM | 1.06 μM |
| 96 | <1 μM | 1.06 μM | >2 μM | 1.49 μM | 1.63 μM |
| 97 | <1 μM | 0.81 μM | 1.62 μM | 1.20 μM | 1.27 μM |
| 98 | <1 μM | 0.84 μM | 1.90 μM | 1.38 μM | 1.52 μM |
| 99 | <1 μM | 0.47 μM | 1.12 μM | 0.80 μM | 0.77 μM |
| 100 | <1 μM | >2 μM | >2 μM | >2 μM | >2 μM |
| 101 | <1 μM | >2 μM | >2 μM | 1.82 μM | 1.93 μM |
| 102 | <1 μM | 0.77 μM | 1.58 μM | 0.83 μM | 1.07 μM |
| 103 | <1 μM | >2 μM | >2 μM | >2 μM | >2 μM |
| 104 | <1 μM | 0.71 μM | 1.50 μM | 0.87 μM | 1.13 μM |
| 105 | <1 μM | >2 μM | >2 μM | >2 μM | >2 μM |
| 106 | <1 μM | >2 μM | >2 μM | >2 μM | >2 μM |
| 107 | <1 μM | >2 μM | >2 μM | >2 μM | >2 μM |

As shown in Table 5, the compounds according to the present disclosure were highly effective in inhibiting c-Myc/Max/DNA complex formation, and were particularly effective in suppressing bladder cancer cell lines.

Evaluation of Selectivity of Compounds of the Present Disclosure

The selectivity of the compounds of the present disclosure to cancer cells was evaluated in the same manner as described in "2. Cell based assay". As a comparative example, KSI-3716 compound of Formula 4, which is a known compound, was used. Measurement results are summarized in Table 6 below.

TABLE 6

| Compound | Cytotoxicity (μM) | | | | |
|---|---|---|---|---|---|
| Compd. | MBT-2 | KU19-19 | UM-UC-3 | 253J | RT4 |
| KSI-3716 | 1.0 | 0.4 | 0.9 | 1.2 | 1.5 |
| Compound 4 | 1.0 | 1.1 | 1.5 | 1.1 | >10 |
| Compound 33 | 0.9 | 1.4 | 1.6 | 1.6 | >10 |

253J: human urinary tract transitional cell carcinoma

UM-UC-3: human urinary bladder transitional cell carcinoma

RT4: human urinary bladder transitional cell papilloma

As shown in Table 6, compound KSI-3716 causes non-selective cell death in both benign (RT4) and malignant (253J and UM-UC-3) bladder cancer cell lines, but the compounds of the present disclosure kill only malignant cancer cells with high selectivity.

The present disclosure provides novel compounds that can have various pharmacological activities by inhibiting c-Myc/Max/DNA complex formation. The compounds according to the present disclosure or pharmaceutically acceptable salts thereof are excellent in safety and has high selectivity in terms of inhibition of c-Myc/Max/DNA complex formation. Accordingly, various excellent effects can be exhibited.

All documents mentioned herein are incorporated herein by reference. When introducing elements of the present disclosure or the preferred embodiments thereof, the articles "a", "an", "the" and "said" are intended to mean that there are one or more of the elements. The terms "comprising," "including," and "having" are intended to be inclusive and mean that there may be additional elements other than the listed elements. Although the present disclosure is described with respect to particular aspects, it should not be construed as limiting the details of these aspects.

The invention claimed is:

1. A compound of Formula 2a or 2b, or a pharmaceutically acceptable salt thereof:

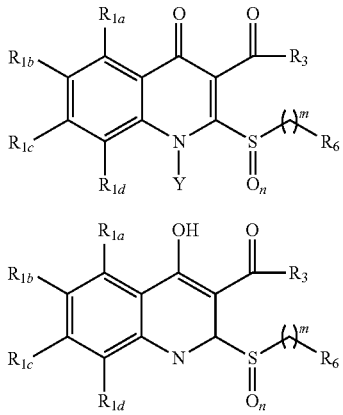

wherein, $R_{1a}$ to $R_{1d}$ are each independently selected from the group consisting of hydrogen, a halogen, $C_{1-6}$alkyl, $C_{1-6}$haloalkyl, $C_{1-6}$hydroxyalkyl, $C_{1-6}$alkoxy, $C_{1-6}$haloalkoxy, $C_{2-10}$alkenyl, $C_{2-10}$haloalkenyl, $C_{2-10}$alkynyl, $C_{2-10}$haloalkynyl, a hydroxyl group, nitro, cyano, $C_{1-6}$alkoxycarbonyl, amino, $C_{1-6}$alkylamino, di($C_{1-6}$alkyl)amino, amino $C_{1-6}$alkyl, $C_{1-6}$alkylamino$C_{1-6}$alkyl, $C_{1-6}$alkanoyl, $C_{3-7}$cycloalkyl, an aryl, a heterocycle, or a heteroaryl, wherein $R_{1a}$ to $R_{1d}$ are each independently unsubstituted or optionally substituted, and one or more of $R_{1a}$ to $R_{1d}$ is a halogen;

$R_3$ is $C_{1-4}$alkyl, isoalkyl, cycloalkyl, phenyl, or $C_{1-4}$ haloalkyl;

n is an integer of 0 to 2;

Y is selected from the group consisting of hydrogen, an alkyl, a haloalkyl, —C(O)alkyl, —C(O)aryl, a sulfonylalkyl, a sulfonylaryl, an aryl, and an alkylaryl, wherein the alkyl is $C_{1-10}$ alkyl and the aryl is an unsubstituted or substituted aryl;

m is 1 or 2; and $R_6$ is phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, 1,2,5-oxadiazole, pyrrolo[2,3-b]pyridine, or benzothiophene, which is unsubstituted, or optionally substituted with one or more of hydrogen, $C_{1-6}$alkyl, $C_{1-6}$haloalkyl, $C_{1-6}$alkoxy, and a halogen, or is optionally substituted with one or more of hydrogen, phenyl, oxazole, pyrazole, pyrrole, imidazole, thiazole, thiophene, pyridine, pyrimidine, furan, indole, benzopyrazole, benzothiazole, benzooxazole, isoxazole, benzoimidazole, and benzothiophene, or is optionally substituted with unsubstituted phenyl.

2. The compound selected from the group consisting of:
3-acetyl-8-bromo-5-chloro-2-(methylsulfinyl)quinolin-4(1H)-one,
3-acetyl-8-bromo-5-chloro-2-(methylthio)quinolin-4(1H)-one,
3-acetyl-2-(benzylthio)-8-bromo-5-chloroquinolin-4(1H)-one,
3-acetyl-2-(benzylsulfinyl)-8-bromo-5-chloroquinolin-4(1H)-one,
3-acetyl-8-bromo-5-chloro-1-methyl-2-(methylthio)quinolin-4(1H)-one,
3-acetyl-5,8-dichloro-2-(methylsulfinyl)quinolin-4(1H)-one,
3-acetyl-6-fluoro-1-methyl-2-(methylthio)quinolin-4(1H)-one,
1-(6-fluoro-4-hydroxy-2-(methylthio)quinolin-3-yl)ethan-1-one,
3-acetyl-8-bromo-1-(4-bromobenzoyl)-5-chloro-2-(methylsulfinyl)quinolin-4(1H)-one,
3-acetyl-8-bromo-5-chloro-2-((4-chlorobenzyl)thio)quinolin-4(1H)-one,
3-acetyl-8-bromo-5-chloro-2-((4-chlorobenzyl)sulfinyl)quinolin-4(1H)-one,
3-acetyl-8-bromo-5-chloro-2-(phenylthio)quinolin-4(1H)-one,
3-acetyl-8-bromo-5-chloro-2-(phenylsulfinyl)quinolin-4(1H)-one,
3-acetyl-8-bromo-5-chloro-2-((2-methoxyphenyl)thio)quinolin-4(1H)-one,
3-acetyl-8-bromo-5-chloro-2-((2-methoxyphenyl)sulfinyl)quinolin-4(1H)-one,
3-acetyl-8-bromo-2-((4-bromophenyl)thio)-5-chloroquinolin-4(1H)-one,
3-acetyl-8-bromo-2-((4-bromophenyl)sulfinyl)-5-chloroquinolin-4(1H)-one,
1,1'-(8-bromo-5-chloro-2-(methylthio)-4-oxoquinoline-1,3(4H)-diyl)bis(ethan-1-one),
1,1'-(8-bromo-5-chloro-2-(methylsulfinyl)-4-oxoquinoline-1,3(4H)-diyl)bis(ethan-1-one),
3-acetyl-2-(benzylsulfinyl)-8-bromo-1-(4-bromobenzoyl)-5-chloroquinolin-4(1H)-one,
3-acetyl-8-bromo-1-(4-bromobenzoyl)-5-chloro-2-(methylsulfonyl)quinolin-4(1H)-one,
3-acetyl-8-bromo-5-chloro-1-(3-chloro-4-fluorobenzyl)-2-(methylsulfinyl)quinolin-4(1H)-one,
3-acetyl-2-(benzylthio)-8-bromo-1-(4-bromobenzoyl)-5-chloroquinolin-4(1H)-one,
3-acetyl-8-bromo-5-chloro-2-(isopropylthio)quinolin-4(1H)-one,
3-acetyl-8-bromo-5-chloro-2-(isopropylsulfinyl)quinolin-4(1H)-one,
3-acetyl-8-bromo-5-chloro-2-((1-phenylethyl)sulfinyl)quinolin-4(1H)-one,
3-(((3-acetyl-8-bromo-5-chloro-4-oxo-1,4-dihydroquinolin-2-yl)thio)methyl)benzonitrile,
3-(((3-acetyl-8-bromo-5-chloro-4-oxo-1,4-dihydroquinolin-2-yl)sulfinyl)methyl)benzonitrile,
3-acetyl-8-bromo-5-chloro-2-((2,4-difluorobenzyl)sulfinyl)quinolin-4(1H)-one,
3-acetyl-8-bromo-5-chloro-2-((3-chloro-4-fluorobenzyl)thio)quinolin-4(1H)-one,
3-acetyl-8-bromo-5-chloro-2-((3-chloro-4-fluorobenzyl)sulfinyl)quinolin-4(1H)-one,
3-acetyl-8-bromo-5-chloro-2-((4-nitrobenzyl)thio)quinolin-4(1H)-one,
3-acetyl-8-bromo-5-chloro-2-((4-nitrobenzyl)sulfinyl)quinolin-4(1H)-one,
3-acetyl-2-(benzylsulfonyl)-8-bromo-5-chloroquinolin-4(1H)-one,
3-acetyl-8-bromo-5-chloro-1-(methylsulfonyl)-2-(methylthio)quinolin-4(1H)-one,
3-acetyl-8-bromo-5-chloro-2-(methylsulfinyl)-1-((trifluoromethyl)sulfonyl)quinolin-4(1H)-one,
3-acetyl-8-bromo-5-chloro-1-((4-chlorophenyl)sulfonyl)-2-(methylthio)quinolin-4(1H)-one, 3-acetyl-8-bromo-5-chloro-2-(methylthio)-1-((4-nitrophenyl)sulfonyl)quinolin-4(1H)-one,
3-acetyl-8-bromo-5-chloro-1-(ethylsulfonyl)-2-(methylsulfinyl)quinolin-4(1H)-one,
3-acetyl-8-bromo-1-((4-(tert-butyl)phenyl)sulfonyl)-5-chloro-2-(methylthio)quinolin-4(1H)-one,
3-acetyl-8-bromo-1-((4-(tert-butyl)phenyl)sulfonyl)-5-chloro-2-(methylsulfonyl)quinolin-4(1H)-one,
3-acetyl-8-bromo-1-((4-(tert-butyl)phenyl)sulfonyl)-5-chloro-2-(methylsulfinyl)quinolin-4(1H)-one,
3-acetyl-8-bromo-5-chloro-2-((2,5-dichlorobenzyl)thio)quinolin-4(1H)-one,
3-acetyl-8-bromo-5-chloro-2-((2,5-dichlorobenzyl)sulfinyl)quinolin-4(1H)-one,
3-acetyl-8-bromo-5-chloro-2-((3,5-difluorobenzyl)thio)quinolin-4(1H)-one,
3-acetyl-8-bromo-5-chloro-2-((3,5-difluorobenzyl)sulfinyl)quinolin-4(1H)-one,
3-acetyl-8-bromo-5-chloro-2-((3-iodobenzyl)thio)quinolin-4(1H)-one,
3-acetyl-8-bromo-5-chloro-2-((3-iodobenzyl)sulfinyl)quinolin-4(1H)-one,
3-acetyl-8-bromo-5-chloro-2-((3-fluorobenzyl)thio)quinolin-4(1H)-one,
3-acetyl-8-bromo-5-chloro-2-((3-fluorobenzyl)sulfinyl)quinolin-4(1H)-one,
3-acetyl-8-bromo-5-chloro-2-(((5-methylisoxazol-3-yl)methyl)sulfinyl)quinolin-4(1H)-one,
1-(2-(benzylthio)-8-bromo-5-chloro-4-hydroxyquinolin-3-yl)ethan-1-one,
1-(2-(benzylsulfinyl)-8-bromo-5-chloro-4-hydroxyquinolin-3-yl)ethan-1-one,
1-(2-(benzylsulfonyl)-8-bromo-5-chloro-4-hydroxyquinolin-3-yl)ethan-1-one,
3-acetyl-8-bromo-5-chloro-2-((3-methoxybenzyl)sulfinyl)quinolin-4(1H)-one,
3-acetyl-8-bromo-5-chloro-2-((4-((trifluoromethyl)thio)benzyl)sulfinyl)quinolin-4(1H)-one,
3-acetyl-5,8-dichloro-2-((4-nitrobenzyl)sulfinyl)quinolin-4(1H)-one,
2-(((3-acetyl-8-bromo-5-chloro-4-oxo-1,4-dihydroquinolin-2-yl)sulfinyl)methyl)benzonitrile,
3-acetyl-8-bromo-5-chloro-2-((3,5-dimethoxybenzyl)sulfinyl)quinolin-4(1H)-one,
3-acetyl-8-bromo-2-((4-(tert-butyl)benzyl)sulfinyl)-5-chloroquinolin-4(1H)-one,
3-acetyl-8-bromo-5-chloro-2-((methoxymethyl)thio)quinolin-4(1H)-one,
3-acetyl-8-bromo-5-chloro-2-mercaptoquinolin-4(1H)-one,
3-acetyl-2-((4-benzoylbenzyl)sulfinyl)-8-bromo-5-chloroquinolin-4(1H)-one,
3-acetyl-8-bromo-5-chloro-2-((4-((trifluoromethyl)sulfinyl)benzyl)sulfinyl)quinolin-4(1H)-one,
2-((3-acetyl-8-bromo-5-chloro-4-oxo-1,4-dihydroquinolin-2-yl)sulfinyl)acetonitrile,
2-((3-acetyl-8-bromo-5-chloro-4-oxo-1,4-dihydroquinolin-2-yl)thio)acetonitrile,
(Z)-3-((3-acetyl-8-bromo-5-chloro-4-oxo-1,4-dihydroquinolin-2-yl)thio)acrylic acid,
3-acetyl-8-bromo-5-chloro-2-((4-(pentafluoro-16-sulfanyl)benzyl)sulfinyl)quinolin-4(1H)-one,
3-acetyl-8-bromo-5-chloro-2-((2-fluoro-4-(pentafluoro-16-sulfanyl)benzyl)sulfinyl)quinolin-4(1H)-one,
3-acetyl-8-bromo-5-chloro-2-((4-(trifluoromethyl)benzyl)sulfinyl)quinolin-4(1H)-one,
3-acetyl-8-bromo-5-chloro-2-((4-(trifluoromethoxy)benzyl)sulfinyl)quinolin-4(1H)-one,
3-acetyl-8-bromo-5-chloro-2-(((5-(trifluoromethyl)furan-2-yl)methyl)sulfinyl)quinolin-4(1H)-one,
4-(((3-acetyl-8-bromo-5-chloro-4-oxo-1,4-dihydroquinolin-2-yl)sulfinyl)methyl)benzonitrile,
3-acetyl-8-bromo-5-chloro-2-((2-chloro-6-fluorobenzyl)sulfinyl)quinolin-4(1H)-one,
3-acetyl-8-bromo-5-chloro-2-((2-m ethoxy-4-(pentafluoro-16-sulfanyl)benzyl)sulfinyl)quinolin-4(1H)-one,
3-acetyl-8-bromo-5-chloro-2-((3-fluoro-5-(pentafluoro-16-sulfanyl)benzyl)sulfinyl)quinolin-4(1H)-one,
3-acetyl-8-bromo-5-chloro-2-((3-(pentafluoro-16-sulfanyl)benzyl)sulfinyl)quinolin-4(1H)-one,
3-acetyl-8-bromo-5-chloro-2-(((perfluorophenyl)methyl)sulfinyl)quinolin-4(1H)-one,
3-acetyl-5,8-dichloro-2-((4-((trifluoromethyl)thio)benzyl)sulfinyl)quinolin-4(1H)-one,
3-acetyl-5,8-difluoro-2-((4-(pentafluoro-16-sulfanyl)benzyl)sulfinyl)quinolin-4(1H)-one,
3-acetyl-5,8-difluoro-2-(((5-(trifluoromethyl)furan-2-yl)methyl)sulfinyl)quinolin-4(1H)-one,
3-acetyl-5,8-difluoro-2-(((5-methylisoxazol-3-yl)methyl)sulfinyl)quinolin-4(1H)-one,
3-acetyl-5,8-dichloro-2-((4-iodobenzyl)sulfinyl)quinolin-4(1H)-one,
3-acetyl-8-bromo-5-chloro-2-((pyridin-3-ylmethyl)sulfinyl)quinolin-4(1H)-one,
5,8-difluoro-3-isobutyryl-2-((4-((trifluoromethyl)thio)benzyl)sulfinyl)quinolin-4(1H)-one,
5,8-dichloro-3-isobutyryl-2-(((5-methylisoxazol-3-yl)methyl)sulfinyl)quinolin-4(1H)-one,
3-benzoyl-5,8-difluoro-2-((4-(pentafluoro-16-sulfanyl)benzyl)sulfinyl)quinolin-4(1H)-one,
3-benzoyl-5,8-dichloro-2-(((5-methylisoxazol-3-yl)methyl)sulfinyl)quinolin-4(1H)-one,
methyl 5-(((3-acetyl-5,8-dichloro-4-oxo-1,4-dihydroquinolin-2-yl)sulfinyl)methyl)furan-2-carboxylate,
2-(((3-acetyl-5,8-dichloro-4-oxo-1,4-dihydroquinolin-2-yl)sulfinyl)methyl)isoindoline-1,3-dione,
methyl 4-(((3-acetyl-5,8-dichloro-4-oxo-1,4-dihydroquinolin-2-yl)sulfinyl)methyl)benzoate,
3-acetyl-5-methoxy-2-((4-(pentafluoro-16-sulfanyl)benzyl)thio)quinolin-4(1H)-one,
3-acetyl-5-methoxy-2-((4-(pentafluoro-16-sulfanyl)benzyl)sulfinyl)quinolin-4(1H)-one,
3-acetyl-5-m ethoxy-2-(((5-methyl isoxazol-3-yl)methyl)sulfinyl)quinolin-4(1H)-one,
8-bromo-5-chloro-3-isobutyryl-2-(((5-methylisoxazol-3-yl)methyl)sulfinyl)quinolin-4(1H)-one,
8-bromo-5-chloro-3-(cyclopropanecarbonyl)-2-(((5-methylisoxazol-3-yl)methyl)sulfinyl)quinolin-4(1H)-one,
5,8-dichloro-3-(cyclopropanecarbonyl)-2-(((5-methylisoxazol-3-yl)methyl)sulfinyl)quinolin-4(1H)-one,
5-(((3-acetyl-8-bromo-5-chloro-4-oxo-1,4-dihydroquinolin-2-yl)sulfinyl)methyl)thiophene-2-carbonitrile,
2-(((6-(1H-pyrazol-1-yl)pyridin-3-yl)methyl)sulfinyl)-3-acetyl-8-bromo-5-chloroquinolin-4(1H)-one,
3-acetyl-2-(((6-aminopyridin-3-yl)methyl)sulfinyl)-8-bromo-5-chloroquinolin-4(1H)-one,
8-bromo-5-chloro-3-(cyclopropanecarbonyl)-2-((4-((trifluoromethyl)thio)benzyl)sulfinyl)quinolin-4(1H)-one,
3-acetyl-8-bromo-5-chloro-2-(((2-methyl-6-(trifluoromethyl)pyridin-3-yl)methyl)sulfinyl)quinolin-4(1H)-one, N-(4-(((3-acetyl-8-bromo-5-chloro-4-oxo-1,4-dihydroquinolin-2-yl)sulfinyl)methyl)phenyl)methanesulfonamide,
3-acetyl-8-bromo-5-chloro-2-(((6-chloropyridin-3-yl)methyl)sulfinyl)quinolin-4(1H)-one,
3-acetyl-8-bromo-5-chloro-2-(((6-((2-methoxyethyl)amino)pyridin-3-yl)methyl)sulfinyl)quinolin-4(1H)-one,
3-acetyl-8-bromo-5-chloro-2-(((4-methyl-1,2,5-oxadiazol-3-yl)methyl)sulfinyl)quinolin-4(1H)-one, and
2-(((1H-pyrrolo[2,3-b]pyridin-5-yl)methyl)sulfinyl)-3-acetyl-8-bromo-5-chloroquinolin-4(1H)-one,
or a pharmaceutically acceptable salt thereof.

3. A composition comprising a compound of claim 1 and a pharmaceutically acceptable carrier.

\* \* \* \* \*